United States Patent [19]
Nicolaou et al.

[11] Patent Number: 5,384,412
[45] Date of Patent: Jan. 24, 1995

[54] SACCHARIDE INTERMEDIATES IN THE FORMATION OF THE CALICHEAMICIN AND ESPERAMICIN OLIGOSACCHARIDES

[75] Inventors: Kyriacos C. Nicolaou, La Jolla, Calif.; Robert D. Groneberg, Oaks, Pa.; Erwin P. Schreiner, Vienna, Austria; Wilhelm Stahl, Frankfurt am Main, Germany

[73] Assignee: The Scripps Research Institute, La Jolla, Calif.

[21] Appl. No.: 972,246

[22] Filed: Nov. 5, 1992

Related U.S. Application Data

[63] Continuation-in-part of Ser. No. 695,251, May 3, 1991, abandoned, which is a continuation-in-part of Ser. No. 520,245, May 7, 1990, abandoned.

[51] Int. Cl.$^6$ .................. C07D 233/00; C07D 315/00
[52] U.S. Cl. .................................. 549/214; 548/110; 548/406; 548/312.4; 549/415; 536/123.1
[58] Field of Search ............... 548/110, 406; 549/214, 549/415

[56] References Cited

FOREIGN PATENT DOCUMENTS 91-17158 11/1991 WIPO ................................ 549/214

OTHER PUBLICATIONS

Ferrier et al, J. Chem. Soc. D., vol. of 1970, pp. 1385–1387.
Nicolaou et al. II, J. Amer. Chem. Soc., vol. 112, pp. 4085–4086 (1990).
Nicolaou et al. III, J. Amer. Chem. Soc, vol. 112, pp. 8193–8195 (1990).
Nicolaou et al. IV, J. Chem. Soc., Chem. Commun., vol. of 1990, pp. 1275–1277.

*Primary Examiner*—Floyd D. Higel
*Attorney, Agent, or Firm*—Welsh & Katz, Ltd.

[57] ABSTRACT

Intermediates useful in preparing the calicheamicin and esperamicin oligosaccharides, and particularly the sulfur- and O-substituted hydroxylamine-containing B ring of both oligosaccharides, are disclosed as are methods of making and using the same, including the preparation of chimeric antibiotics using the same.

16 Claims, 31 Drawing Sheets

Calicheamicin γ₁ᴵ

Scheme 1

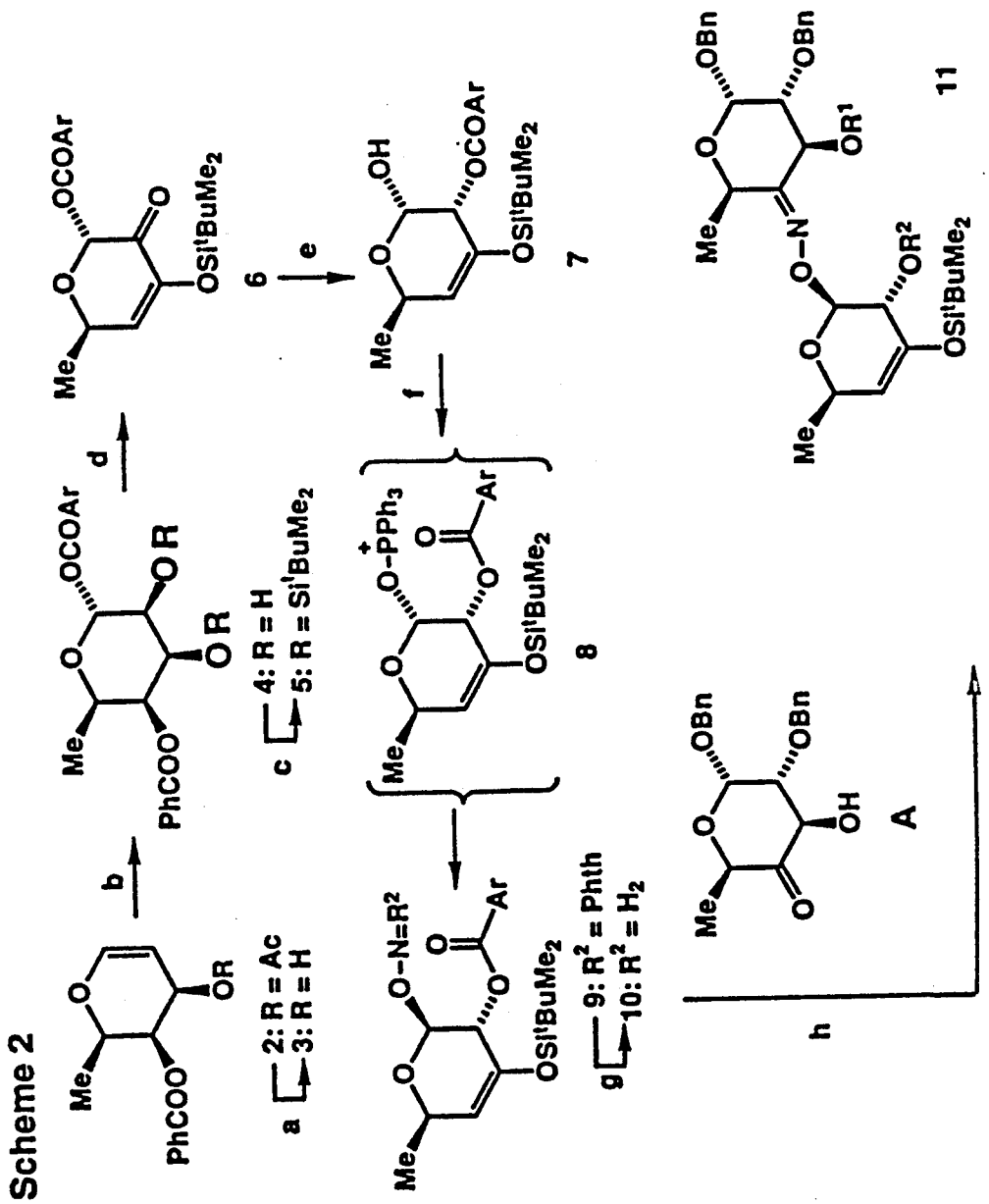
FIGURE 4-A

FIGURE 4-B
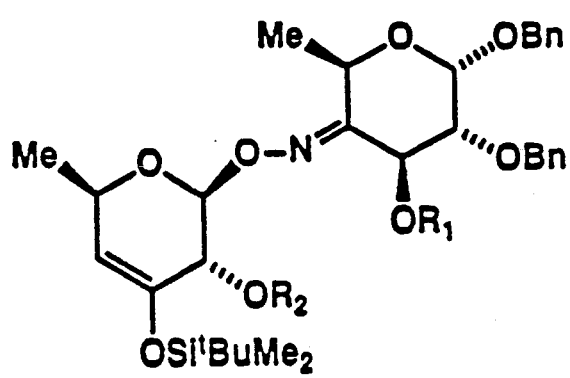
- l ⎡ 11: R¹ = H, R² = COC₆H₄-m-Cl
- j ⎣→ 12: R¹ = Si^tBuMe₂, R² = COC₆H₄-m-Cl
- k  → 13: R¹ = Si^tBuMe₂, R² = H
-    → 14: R¹ = Si^tBuMe₂, R² = -C(=S)-N(imidazole)
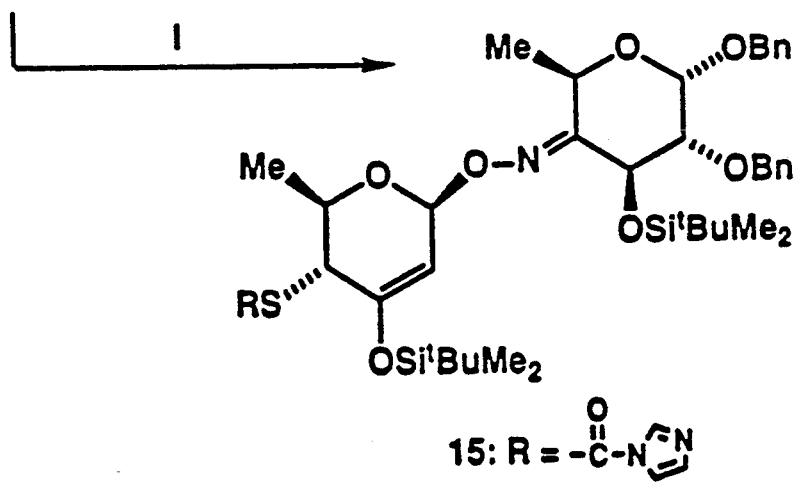
15: R = -C(=O)-N(imidazole)

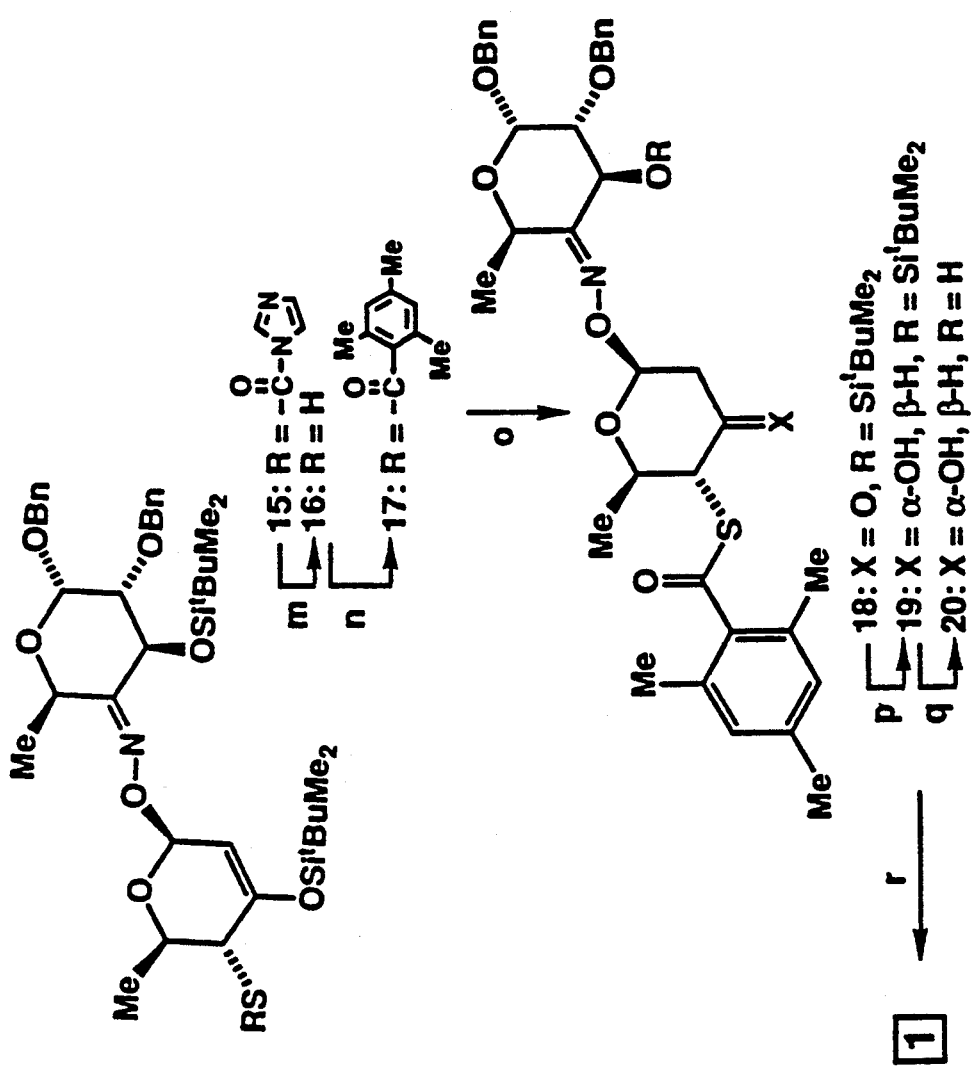
FIGURE 4-C

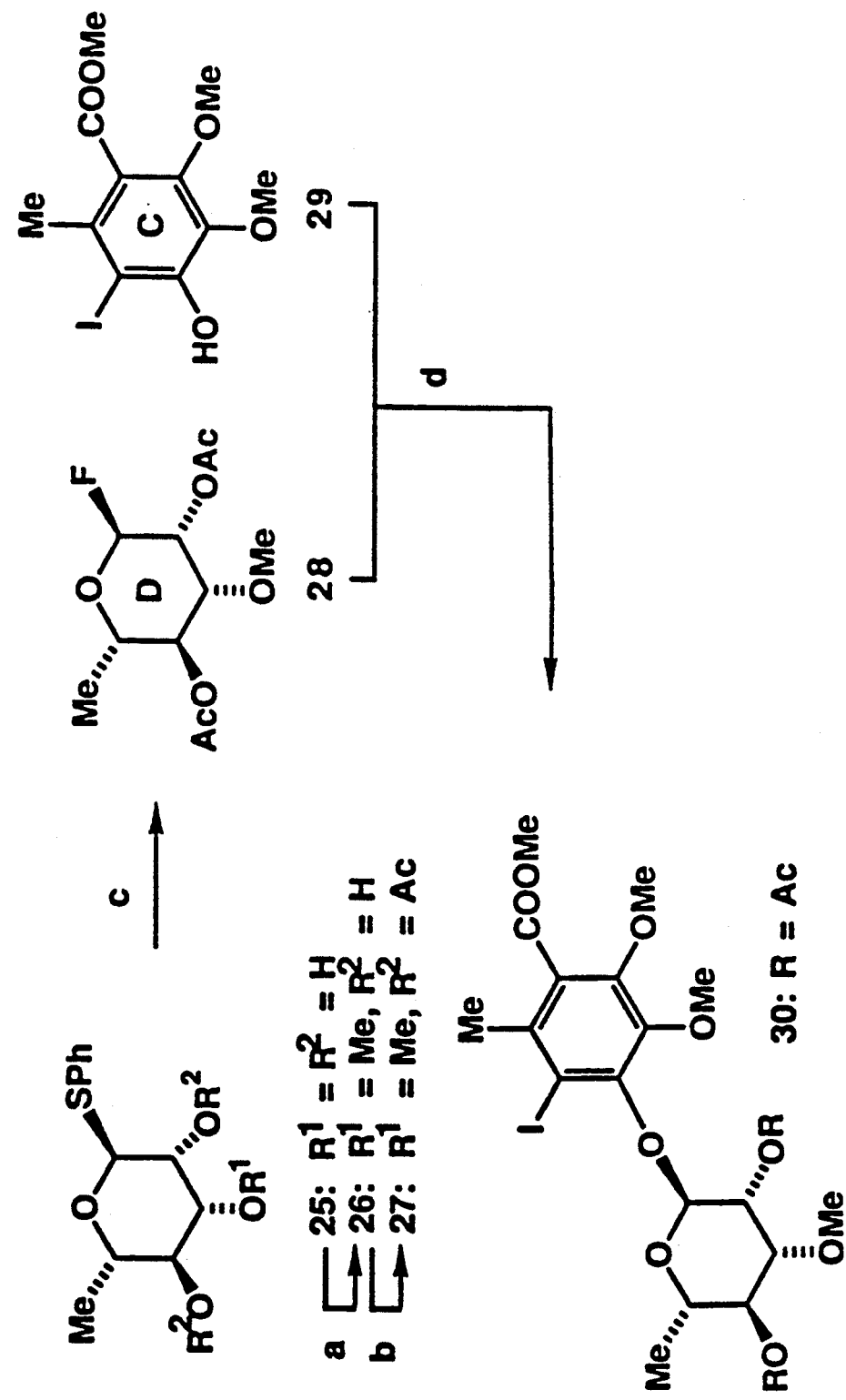
FIGURE 6-A

FIGURE 6-B
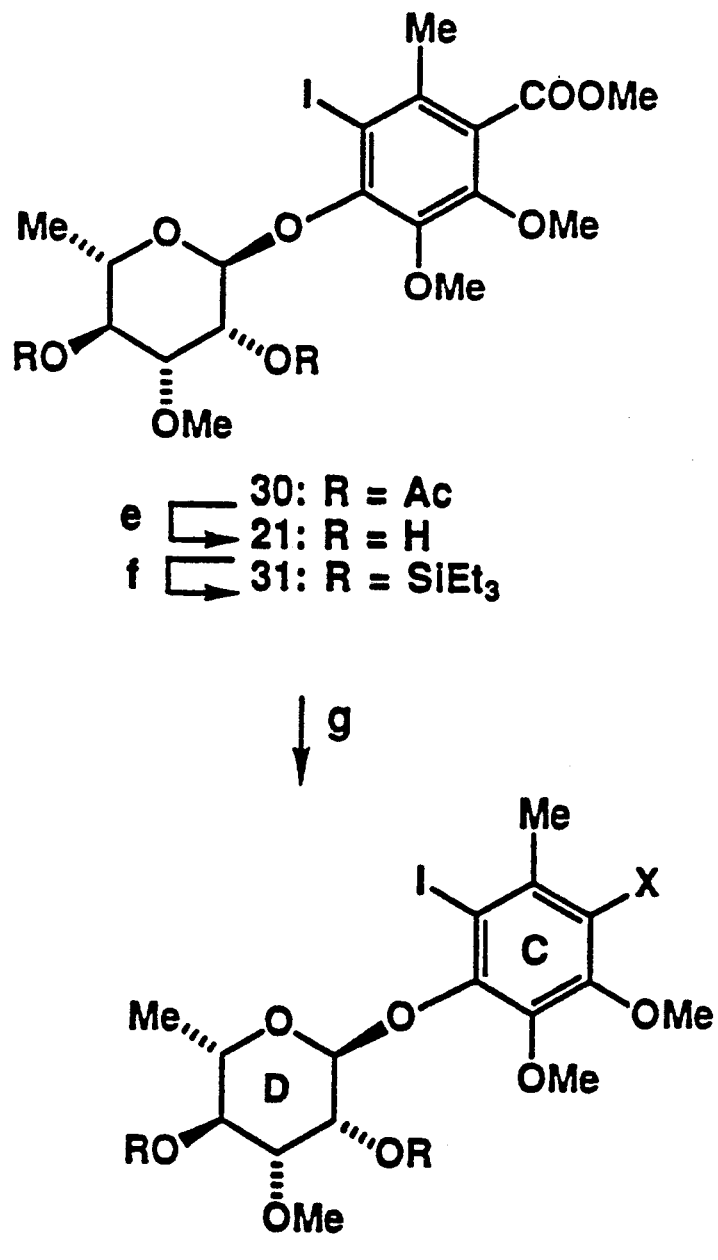

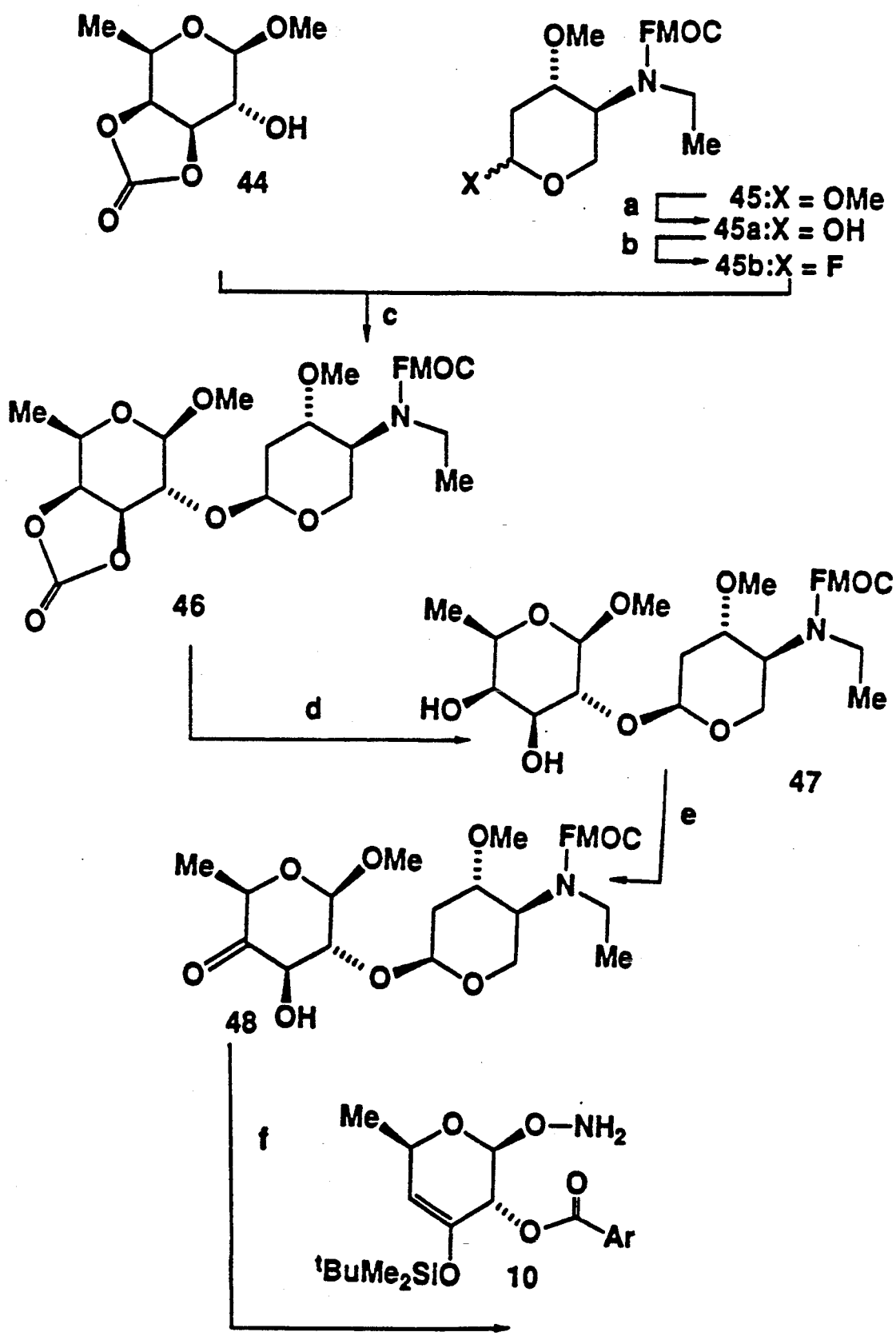
FIGURE 8-A
Scheme 5

FIGURE 8-B
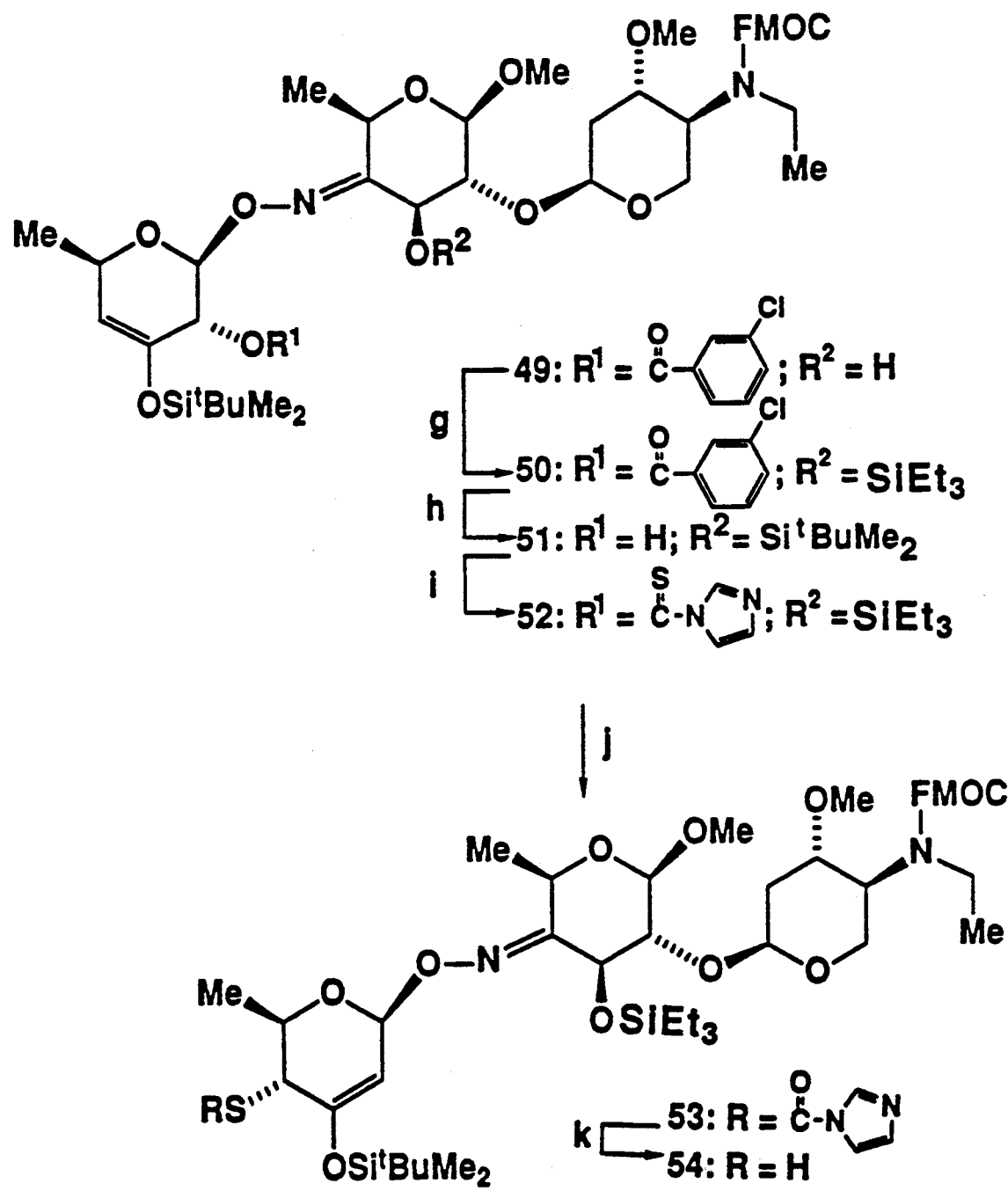

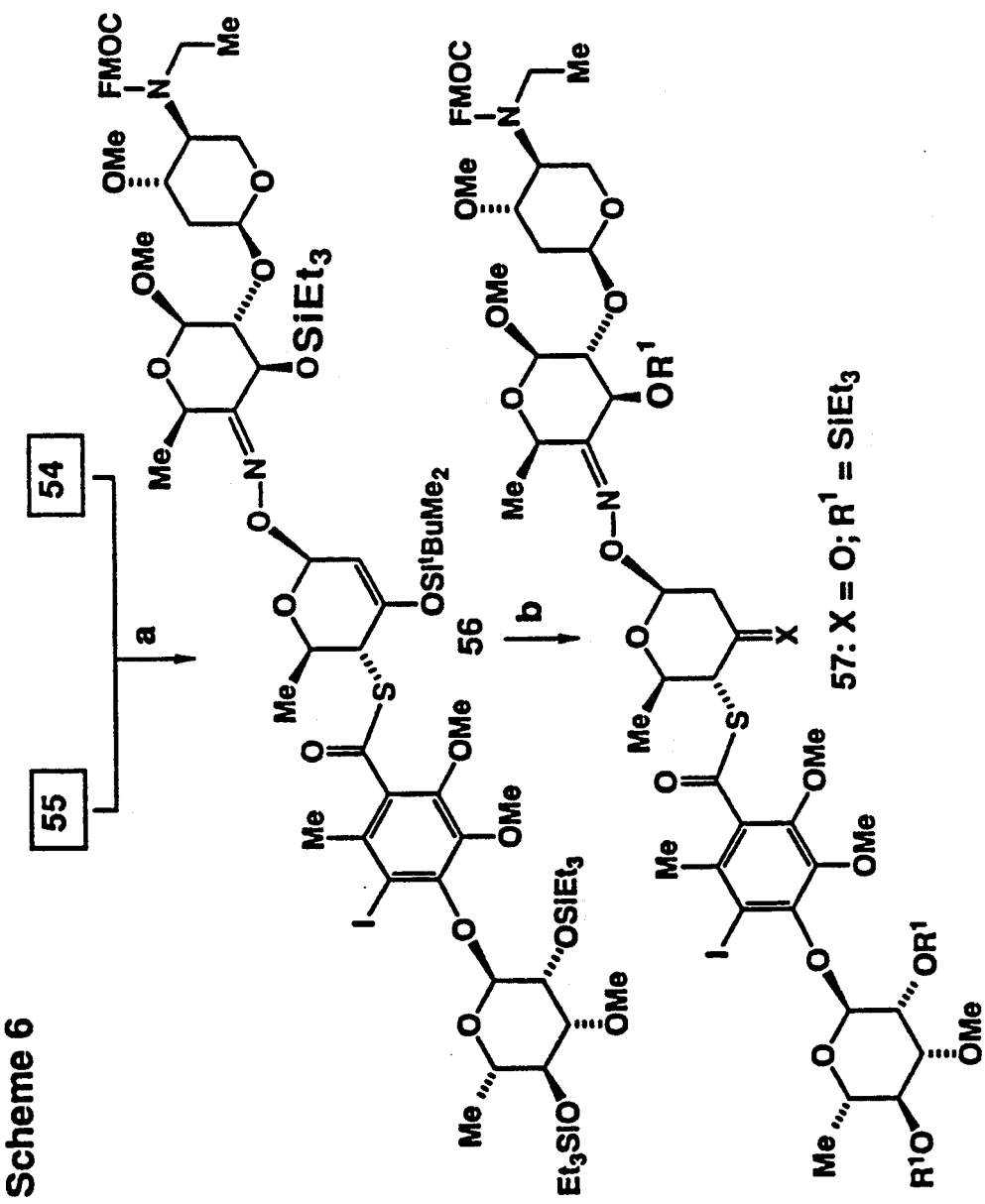
FIGURE 9-A
Scheme 6

FIGURE 9-B
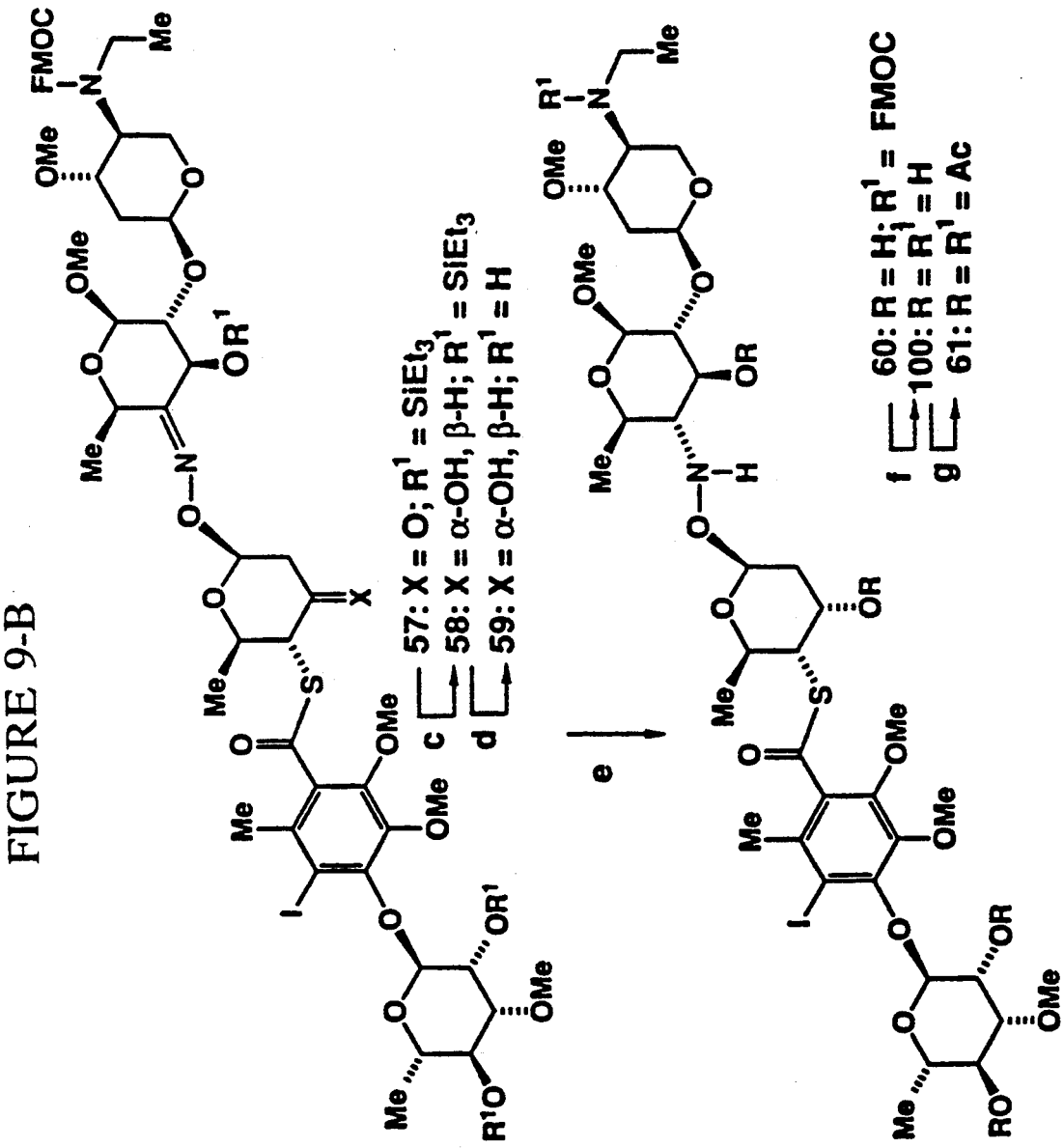

FIGURE 10-A
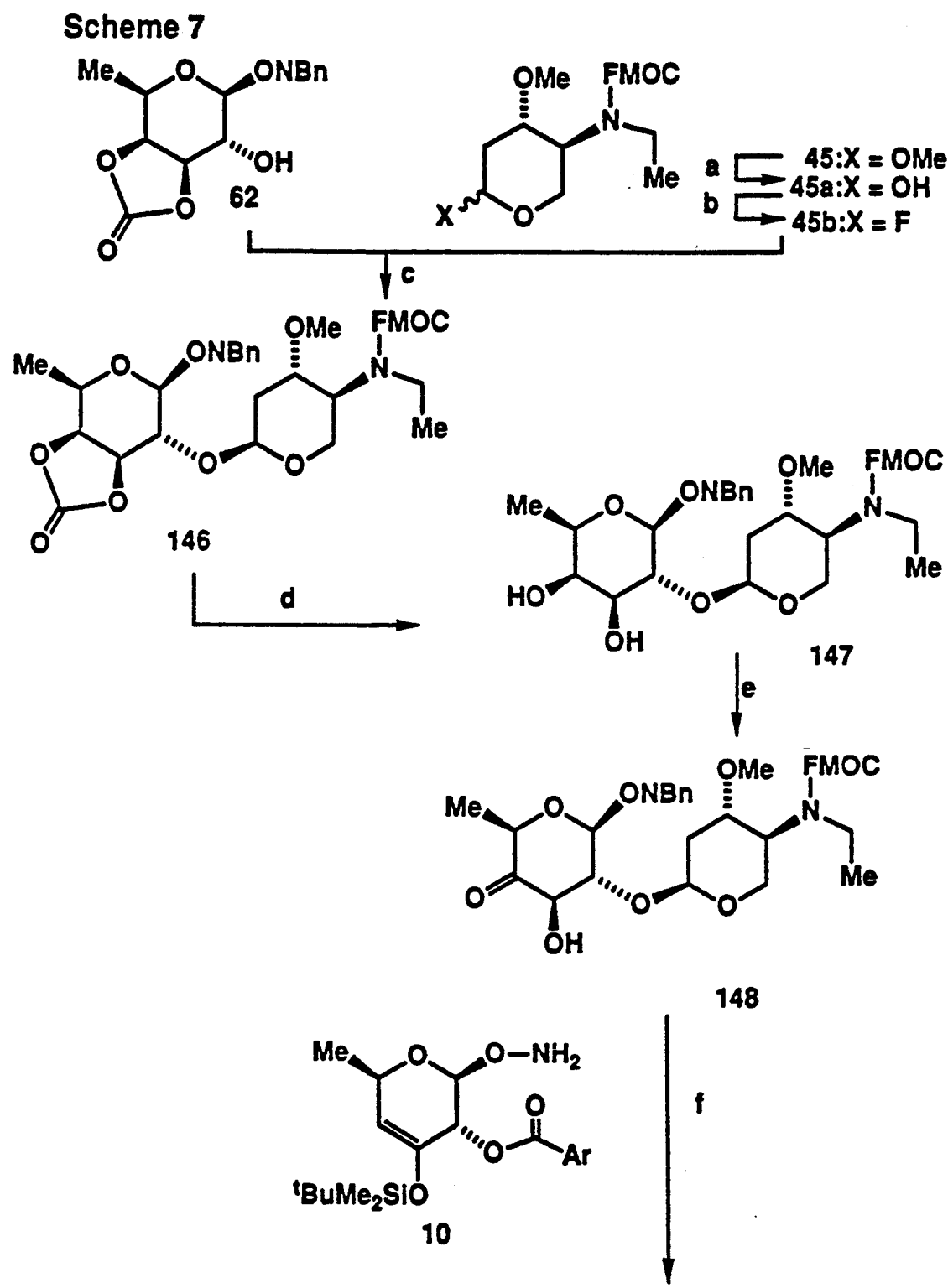

FIGURE 10-B
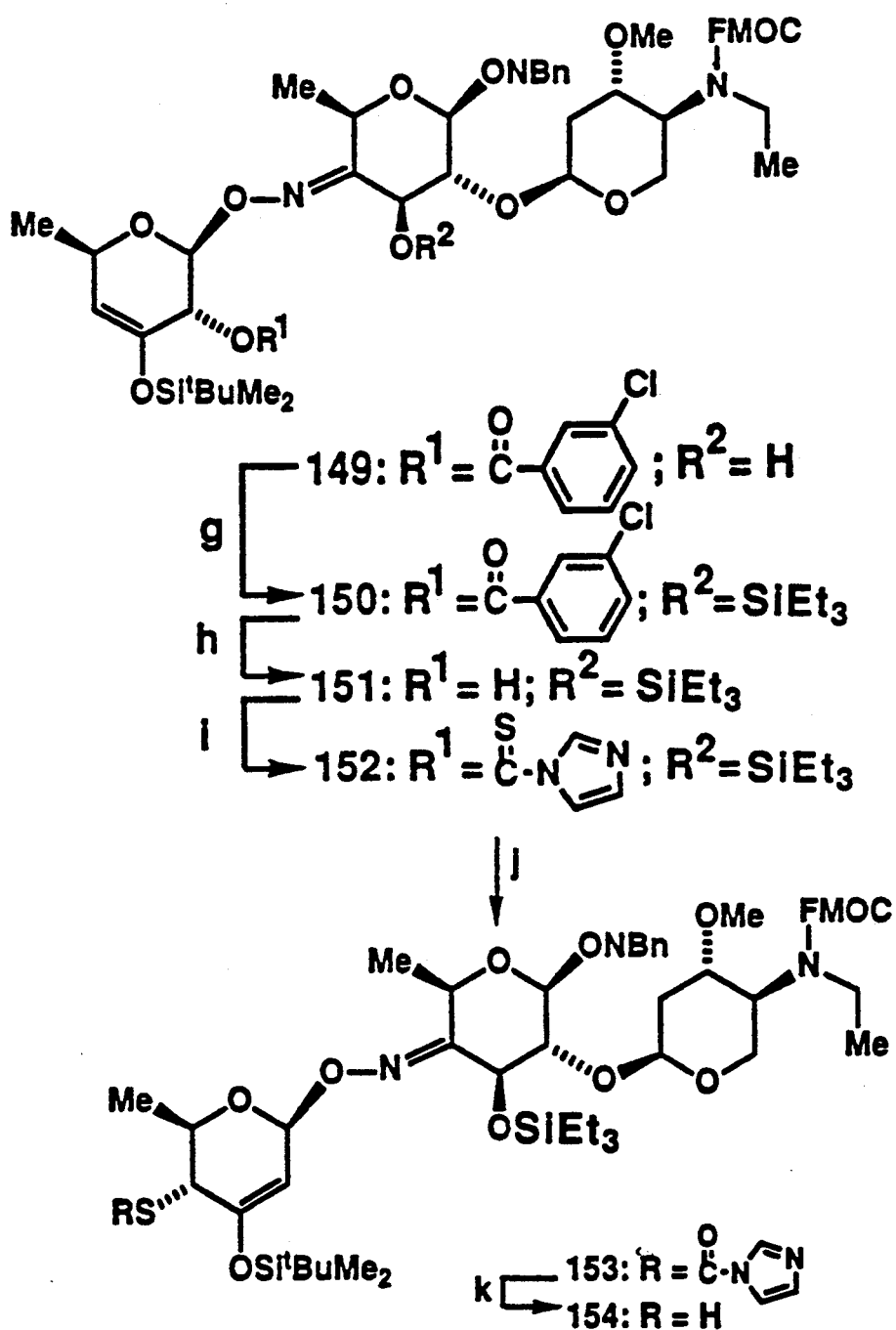

Scheme 8

FIGURE 12-A
Scheme 9
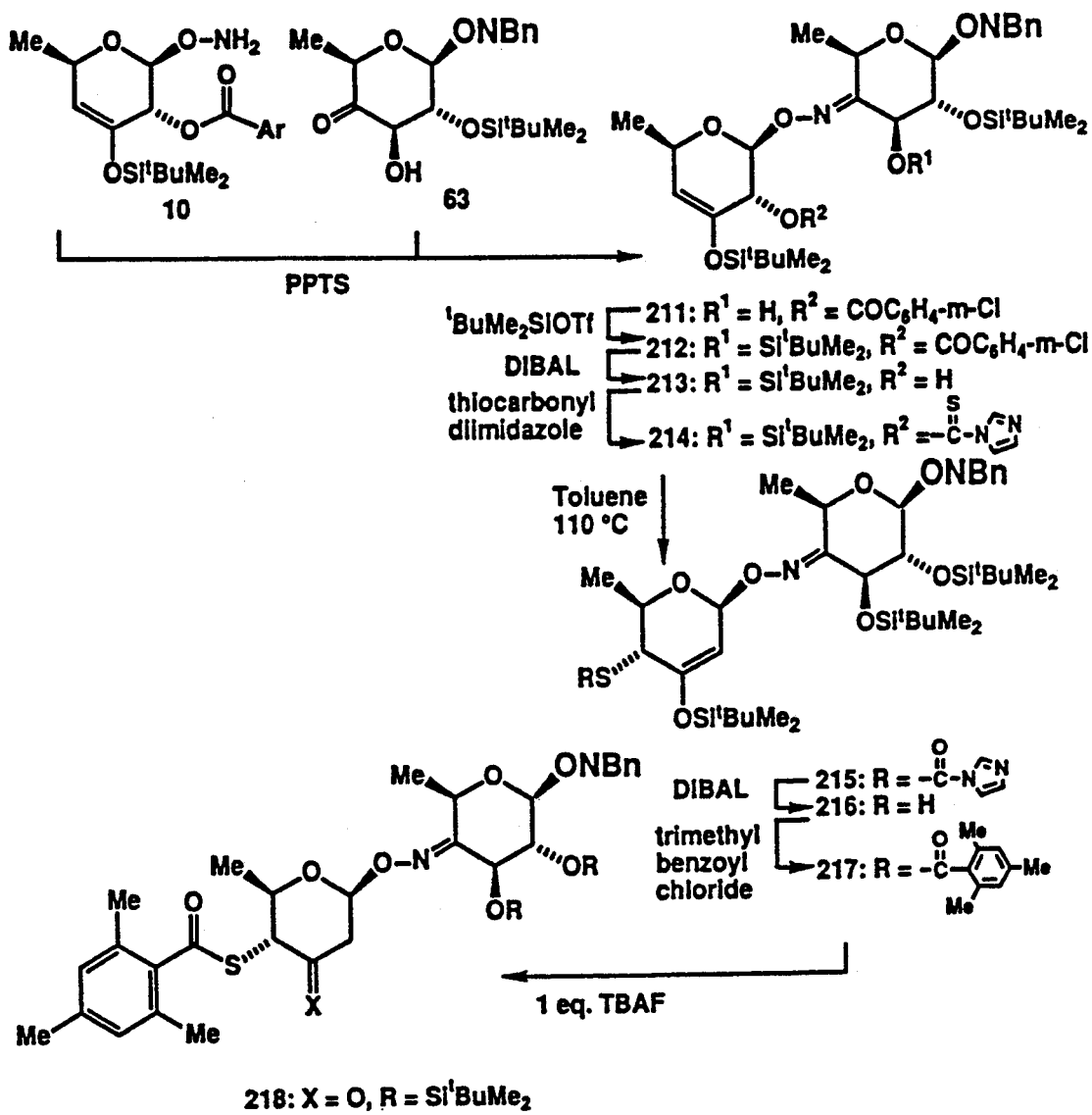

FIGURE 12-B
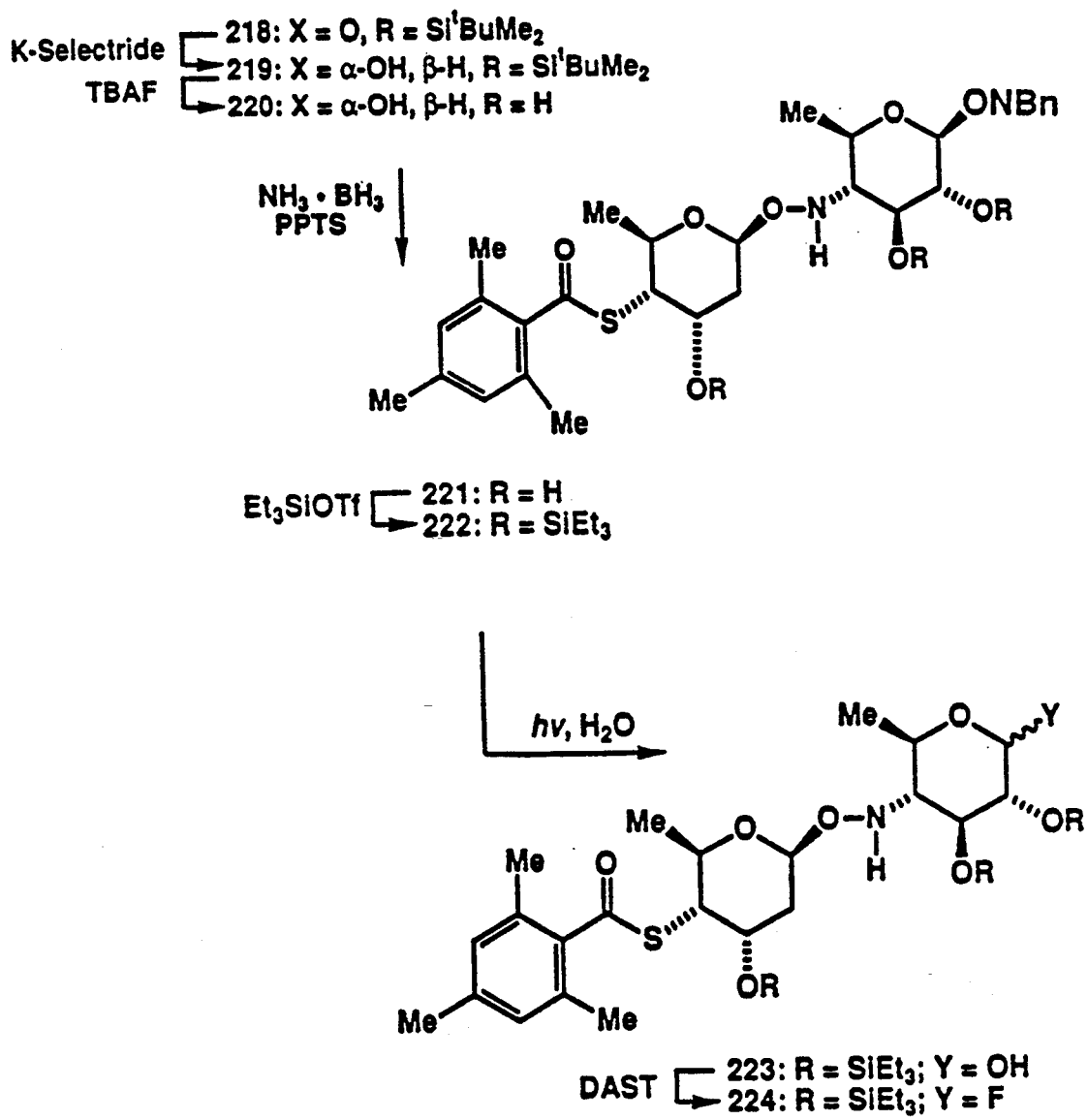

FIGURE 12-C
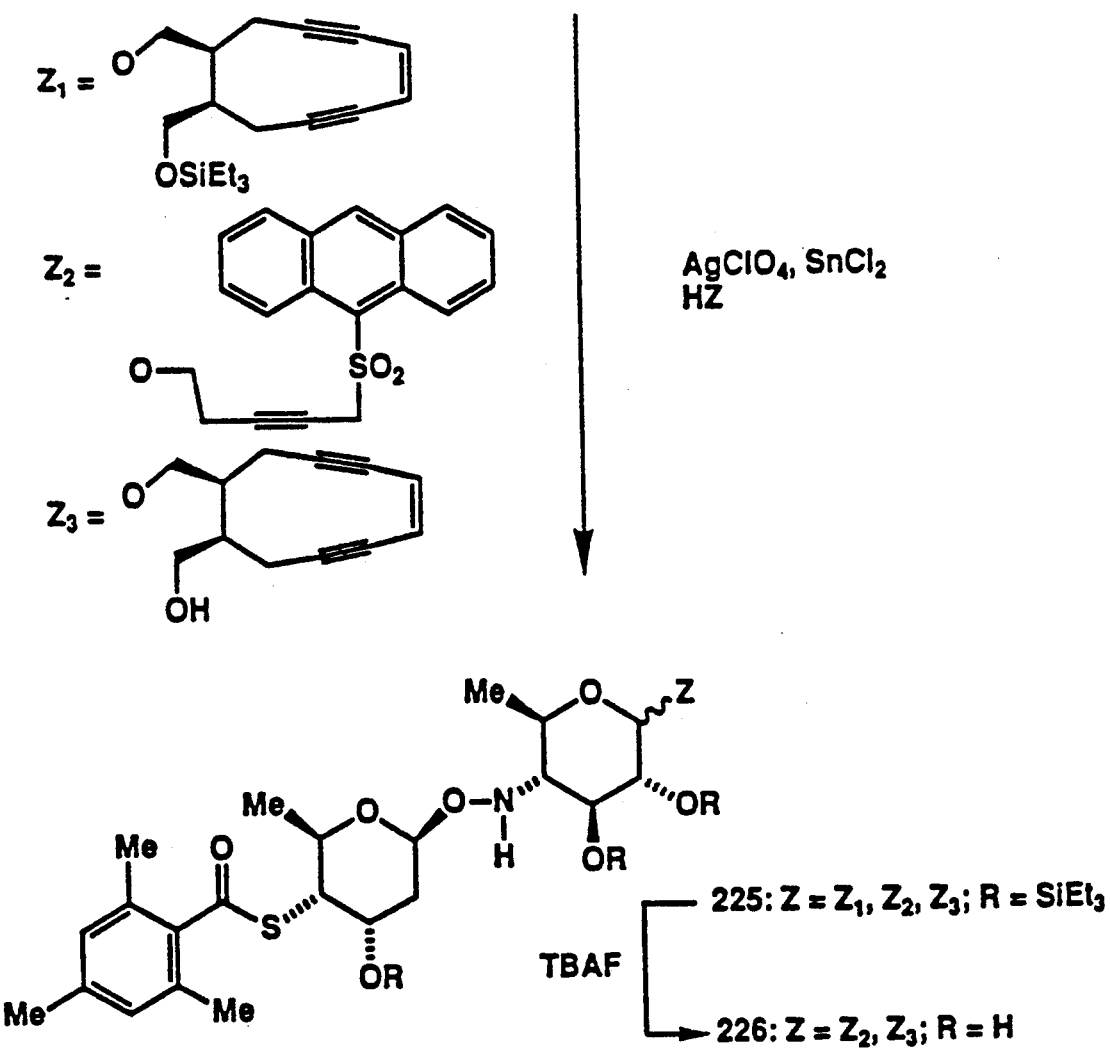

FIGURE 13-A
Scheme 10
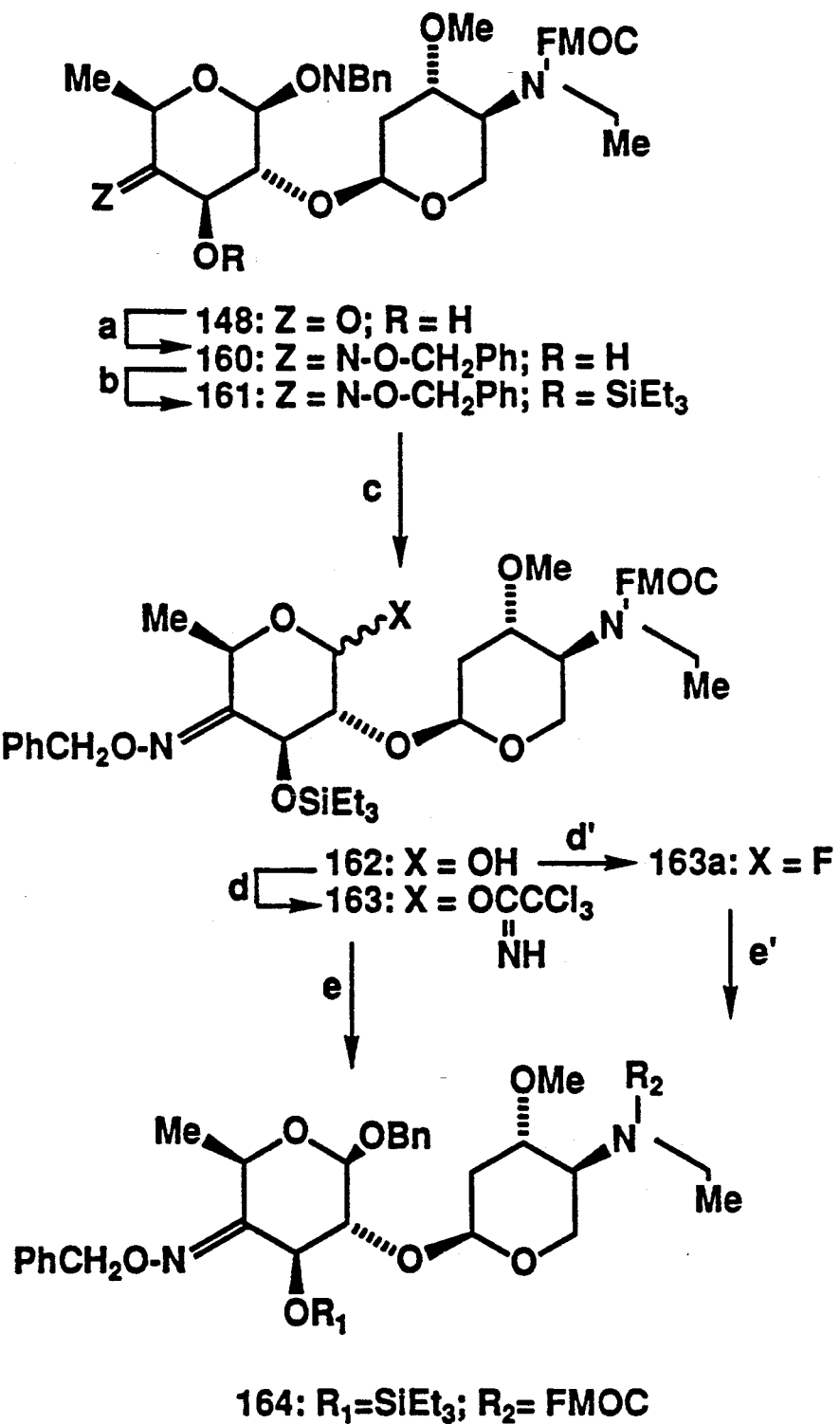

FIGURE 13-B
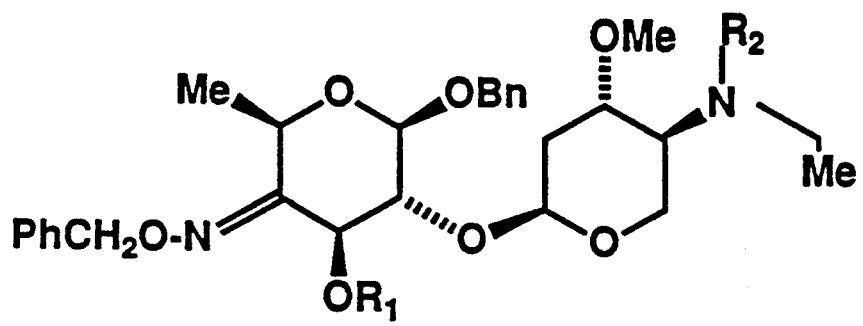
f ⌈ 164: $R_1$ = SiEt$_3$; $R_2$ = FMOC
  ├ 165: $R_1$ = H; $R_2$ = FMOC
g └→ 166: $R_1$ = $R_2$ = H
h ↓
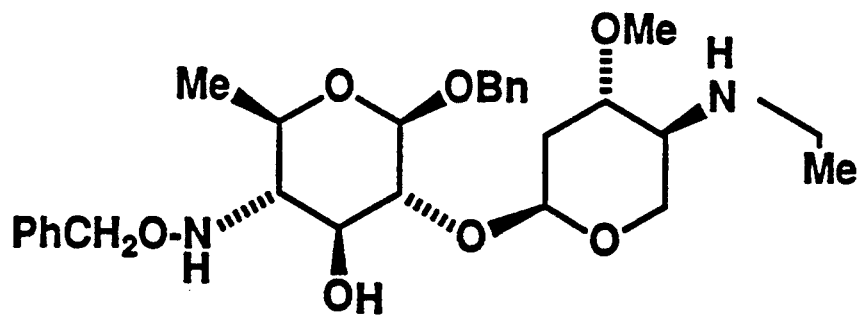
167

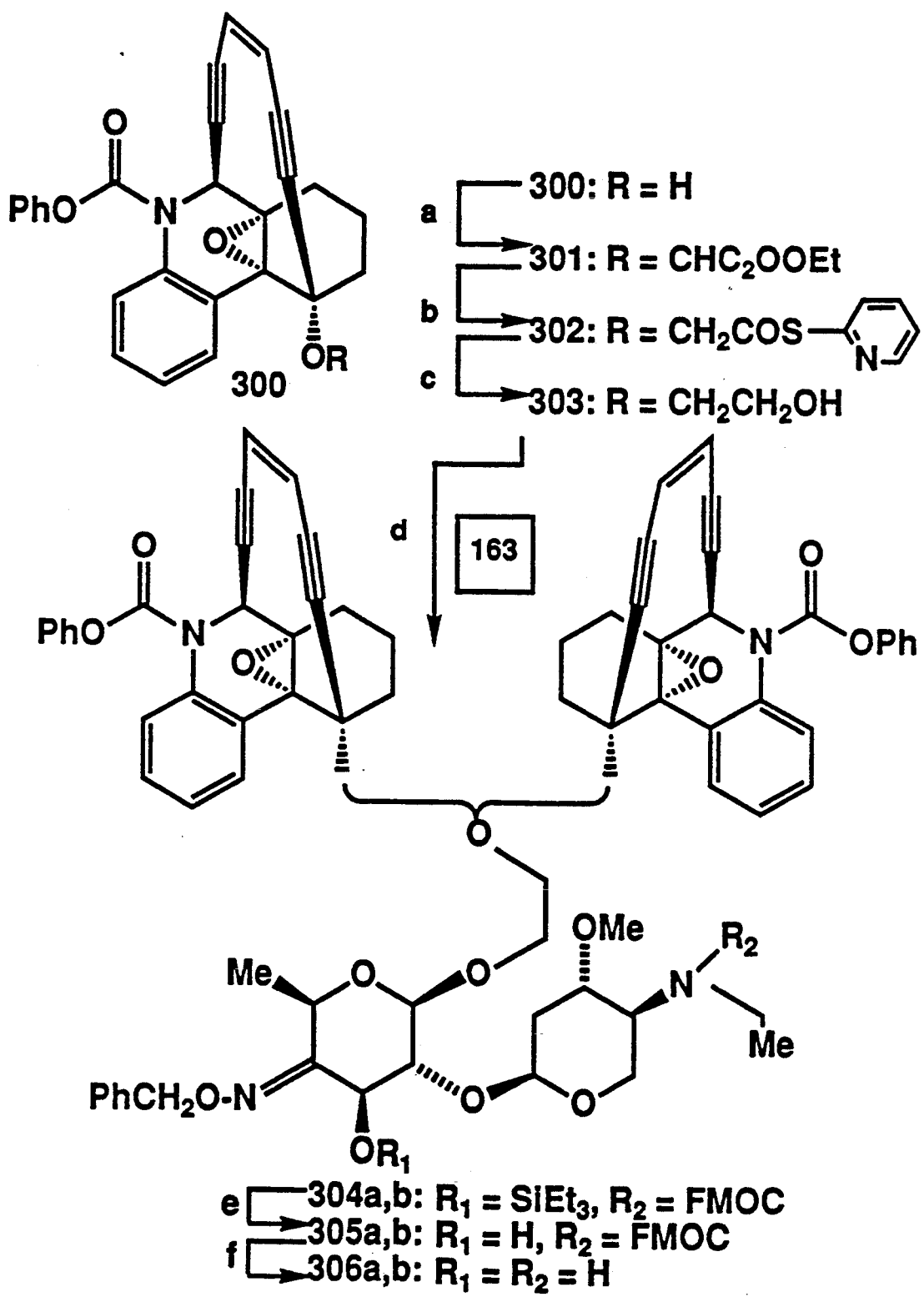
Scheme 11 — FIGURE 14-A

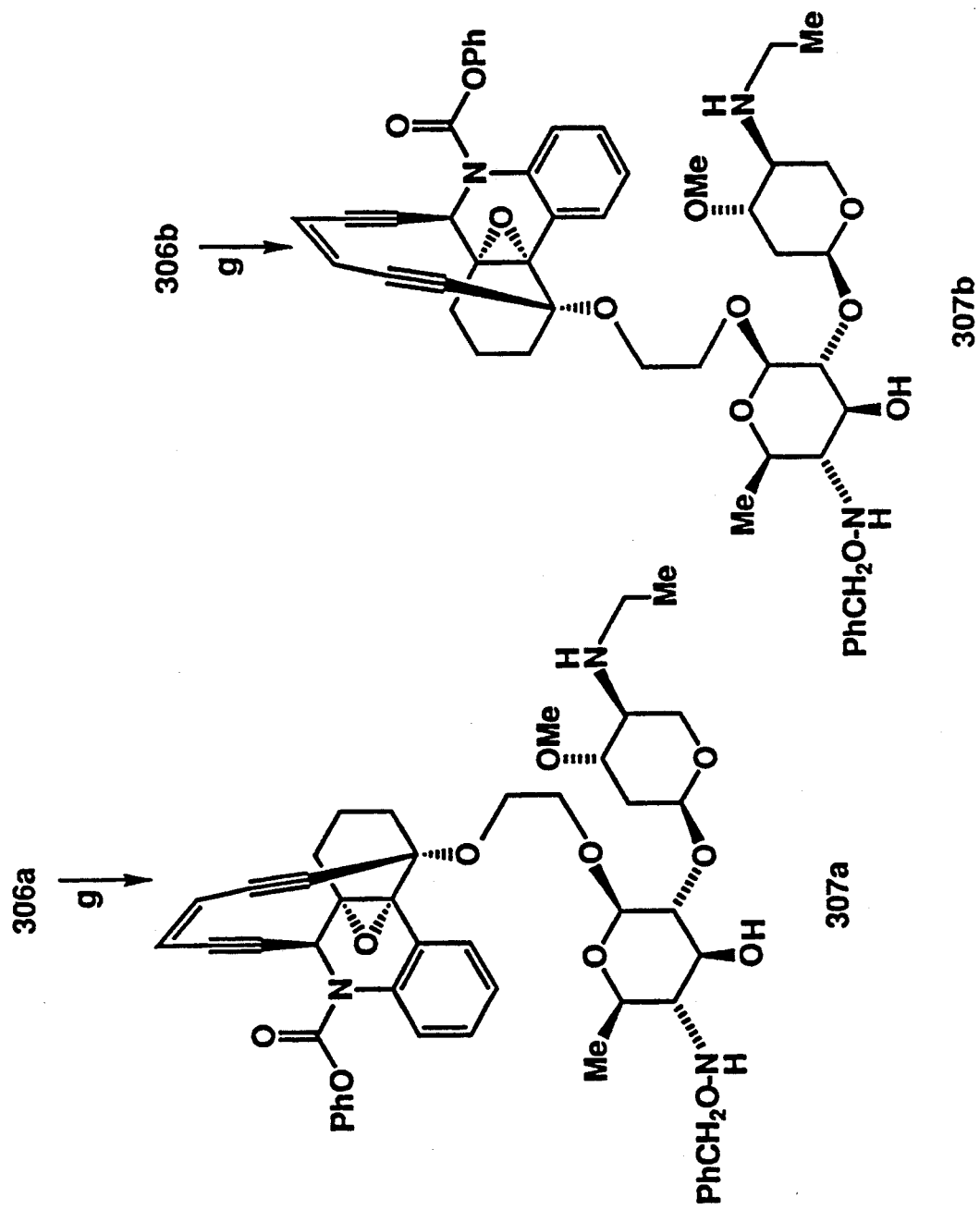
FIGURE 14-B

FIGURE 15-A
Scheme 12
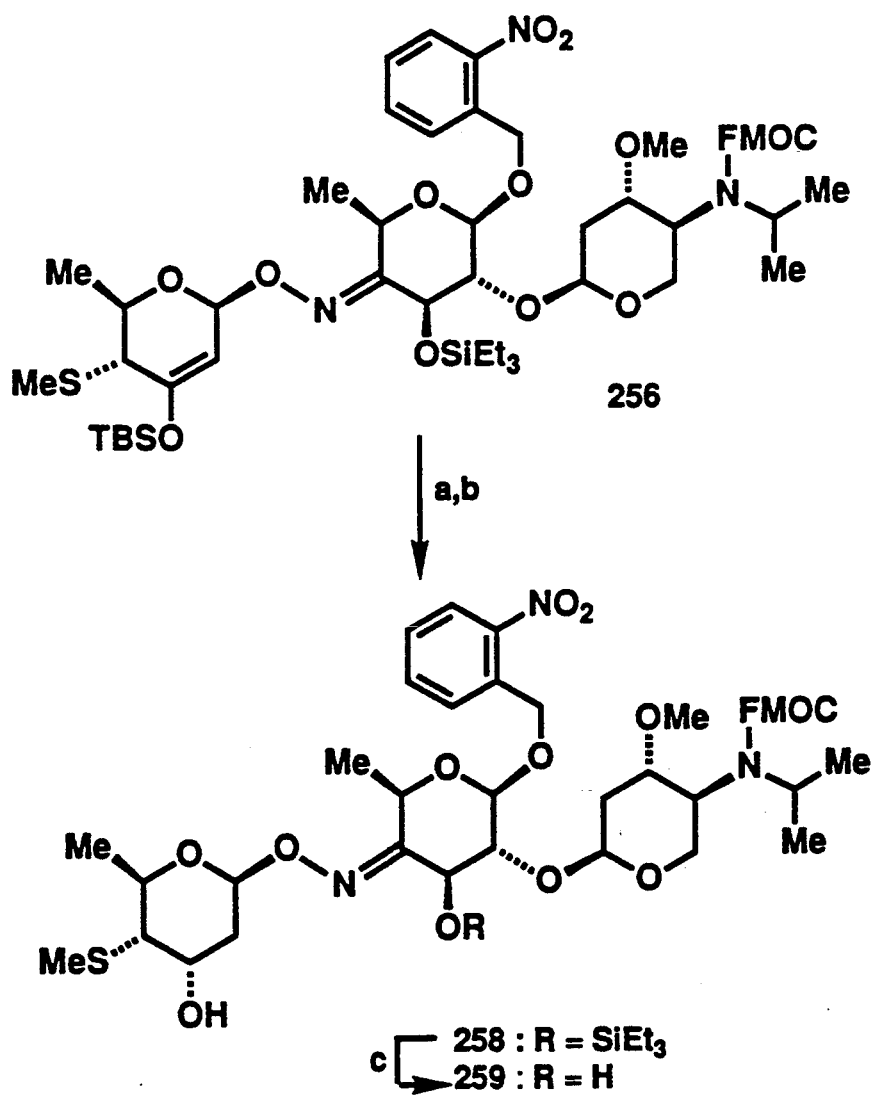

FIGURE 15-B
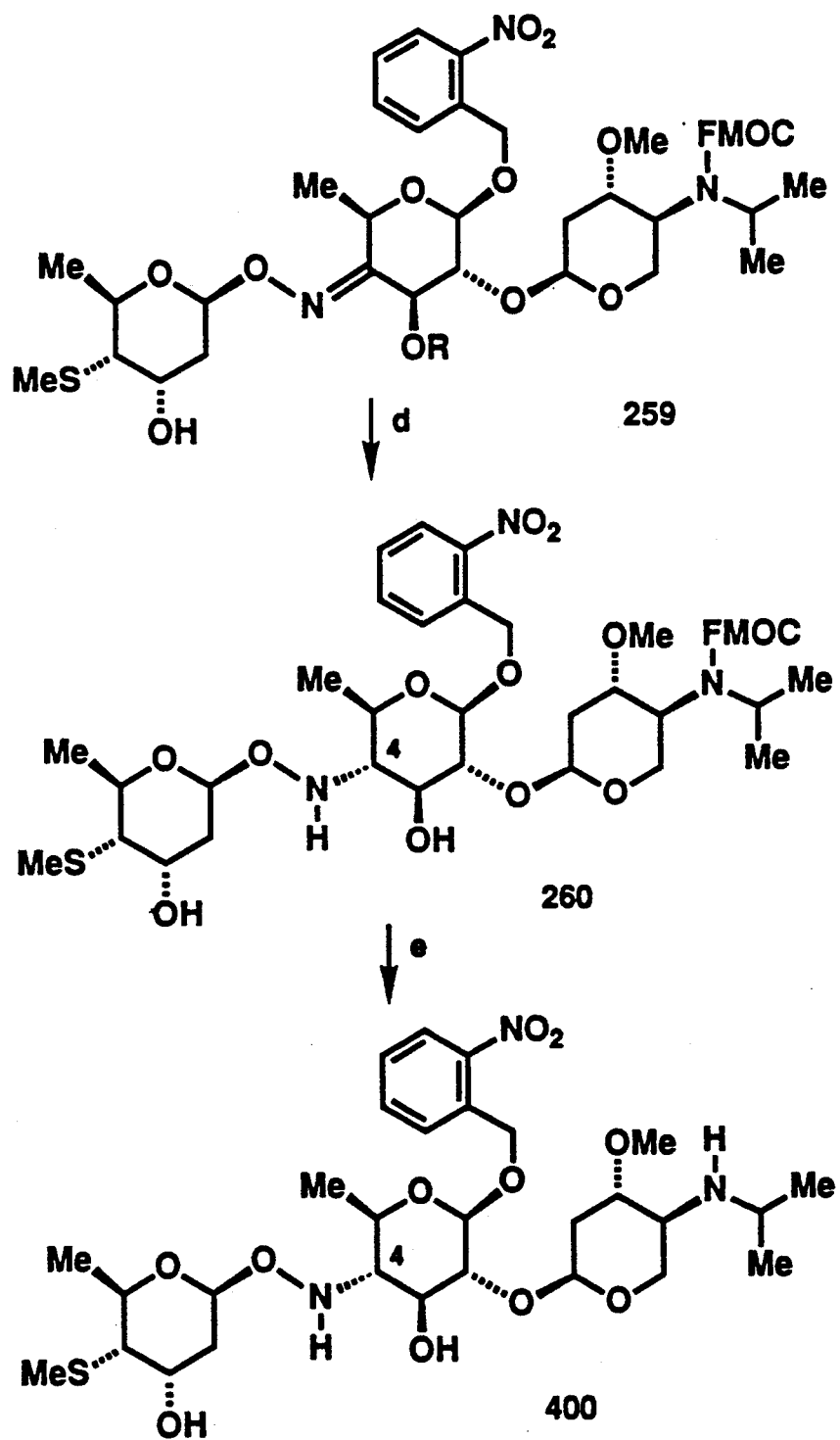

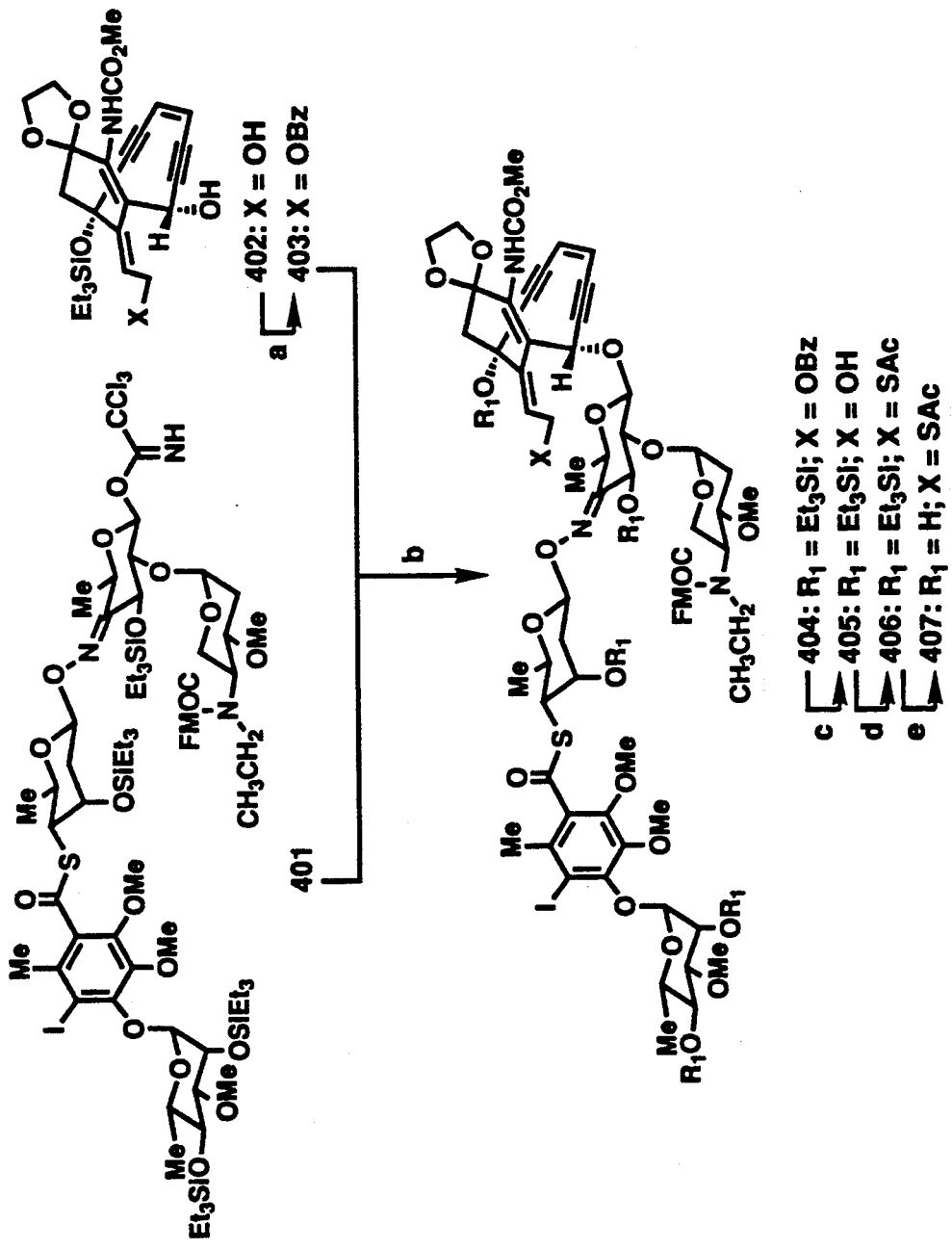
FIGURE 16-A
Scheme 13

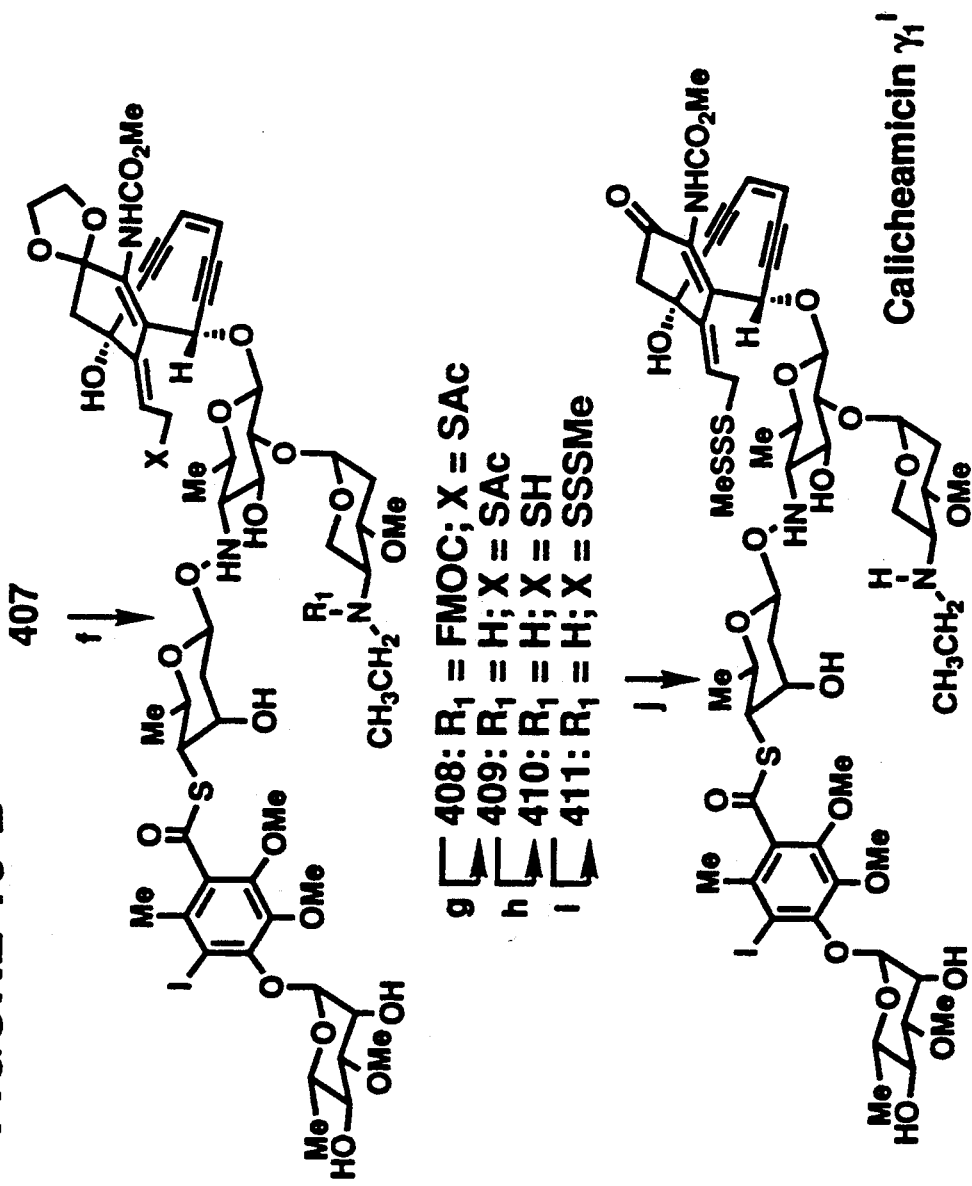
FIGURE 16-B

Scheme 14

Scheme 16

SACCHARIDE INTERMEDIATES IN THE FORMATION OF THE CALICHEAMICIN AND ESPERAMICIN OLIGOSACCHARIDES

GOVERNMENTAL SUPPORT

This invention was made with support from the Government of the United States of America, and the Government of the United States of America has certain rights in the invention.

CROSS-REFERENCE TO RELATED APPLICATION

This is a continuation-in-part of application Ser. No. 07/695,251, filed May 3, 1991, now abandoned which is a continuation-in-part of application Ser. No. 07/520,245, filed May 7, 1990, whose disclosures are incorporated by reference, now abandoned.

DESCRIPTION

TECHNICAL FIELD

The present invention relates generally to the antibiotics calicheamicin and esperamicin, and more particularly to intermediates useful in the preparation of the calicheamicin and esperamicin oligosaccharide portions.

BACKGROUND ART

The calicheamicin [Lee et al., *J. Am. Chem. Soc.*, 109:3466 (1987)] and esperamicin [Golik et al., *J. Am. Chem. Soc.*, 109:3462 (1987)] families of antibiotics contain a complex bicyclic enediyne allylic trisulfide core structure linked through glycosyl bonds to an oligosaccharide chain. The oligosaccharide portions of each of those molecules contain a number of substituted sugar derivatives, and each of those oligosaccharide portions contains a tetrahydropyran ring that is substituted on the ring both with a sulfur atom and with the oxygen atom of a hydroxylamine group.

The chemical structure of calicheamicin $\gamma_1^I$, which contains a more complex oligosaccharide group than an esperamicin, is illustrated in FIG. 1 herein. The saccharide unit lettered "B" is the before discussed sulfur- and O-hydroxylamine-substituted tetrahydropyran derivative.

The saccharide rings of an esperamicin corresponding to rings "A" and "E" of FIG. 1 are substituted similarly to those depicted, except that the esperamicin ring corresponding to ring E includes an N-isopropyl rather than N-ethyl group. The corresponding "B" ring of an esperamicin contains an S-methyl rather than the S-(saccharide-substituted)-derivatized benzoyl group (C and D rings) shown in FIG. 1. The structures of esperamicin and some of its derivatives are illustrated in U.S. Pat. No. 4,837,206, whose disclosures are incorporated by reference.

The enediyne-containing (aglycone or core) and carbohydrate portions of calicheamicin and esperamicin appear to carry out different roles in the biological activity of those molecules. Thus, the core portion appears to cleave DNA [Zein et al., Science, 240:1198 (1988)], whereas the oligosaccharide portion of calicheamicin appears to guide the drug to a double stranded DNA minor groove in which the drug anchors itself on the 5' side of a TCCT sequence, and the core cleaves the DNA. Esperamicins are less sequence specific. [Zein et al., *Science*, 244:697 (1989)].

Studies of the effect on DNA cleavage of derivatization or removal of one or more of the D and E rings of calicheamicin (FIG. 1) indicate the following: removal of the E ring (amino sugar) provided a drug with the same DNA cleaving specificity as the parent, but having a DNA-cleaving efficiency 2 to 3 orders of magnitude less; acylation of the E ring amine maintained specificity but lowered efficiency; removal of the D ring (terminal rhamnose) maintained specificity, but lowered efficiency 50–100 times; and removal of the D and E rings (terminal rhamnose and amino sugar) resulted in inhibition of cutting. [Zein et al., *Science*, 244:697 (1989)].

Esperamicin lacks the C and D rings and includes a further complex saccharide structure linked to an additional core hydroxyl group. U.K. Patent Application 2,179,649A reports that acid hydrolysis of esperamicins led to cleavage of that second complex saccharide structure and a resulting esperamicin derivative referred to as BBM-1675C that was about as effective as the starting esperamicin BBM-1675A$_1$ (esperamicin A$_1$), and more so than esperamicin BBM-1675A$_2$ (esperamicin A$_2$) as an antitumor and antimicrobial agent. From the discussion in this U.K. application, the oligosaccharide portion of BBM-1675C contains rings analogous to the A, B and E rings of calicheamicin shown in FIG. 1.

U.K. Patent Application 2,179,649A also disclosed that further hydrolysis of esperamicin BBM-1675C led to another esperamicin derivative named BBM-1675D that was also said to be about as effective as esperamicin BBM-1675A$_1$, as an antitumor and antimicrobial agent. The data presented indicate that esperamicin BBM-1675D possessed only two saccharide rings; i.e. those corresponding to the A and E rings of FIG. 1 herein.

Thus, the art has recognized the importance of the oligosaccharide portions of the calicheamicin and esperamicin antibiotics, and has recognized that the saccharide rings in the calicheamicin group can affect the activity of the drug. The results disclosed in Zein et al., *Science*, 244:697 (1989) and those in U.K. Patent Application 2,179,649A indicate a possible conflict as to the effect of the individual saccharide portions on efficacy, although different assay methods were used.

It would be important therefore to be able to prepare an oligosaccharide portion of a calicheamicin or the corresponding portion of an esperamicin and derivatives thereof so that the specificities of those materials can be further studied and fine-tuned. It would also be of importance to link a calicheamicin or esperamicin oligosaccharide or a derivative or analog thereof to another known DNA cleaving chemical to create a synthetic, chimeric antibiotic.

The present invention describes the synthesis of key intermediates useful in the preparation of a calicheamicin or esperamicin oligosaccharide portion, an oligosaccharide portion derivative or analog, as well as the synthesis of chimeric antibiotics containing such an oligosaccharide.

BRIEF SUMMARY OF THE INVENTION

The present invention contemplates intermediate compounds useful in the preparation of the oligosaccharide portions of calicheamicin and esperamicin, as well as analogs and derivatives thereof and a method of preparing the same.

One contemplated intermediate compound corresponds in structure to that of the formula below,

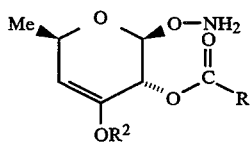

wherein R is a moiety selected from the group consisting of hydrogen, $C_1$–$C_5$ alkyl, phenyl and m-chlorophenyl; and $R^2$ is a moiety selected from the group consisting of tri-$C_1$–$C_6$ alkylsilyl, di-$C_1$–$C_6$ alkylphenylsilyl, and $C_1$–$C_6$ alkyldiphenylsilyl.

In preferred practice, R is a substituted phenyl moiety such as m-chlorophenyl, and $R^2$ is a tri-$C_1$–$C_6$ alkylsilyl group such as t-butyldimethylsilyl or triethylsilyl. This preference for $R^2$ holds for all of the compounds in which such a group is present.

Another contemplated compound corresponds in structure to that shown in the formula below,

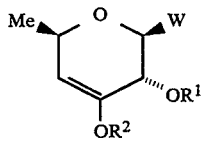

where $R^1$ is hydrogen or COR, and R is a moiety selected from the group consisting of hydrogen, $C_1$–$C_5$ alkyl, phenyl and m-chlorophenyl;

$R^2$ is a moiety selected from the group consisting of tri-$C_1$–$C_6$ alkylsilyl, di-$C_1$–$C_6$ alkylphenylsilyl, and $C_1$–$C_6$ alkyldiphenylsilyl; and —W is (i) an N-hydroxy cyclic imido group, —ON=$R^4$ in which $R^4$ has 4 to about 8 carbon atoms or (ii) an O,N-di-substituted oxime group, —ON=$R^5$, whose $R^5$ carbon-containing portion is derived from a group consisting of a $C_1$–$C_6$ alkyl ketone or aldehyde, and a tetrahydropyranone derivative with the proviso that $R^1$ is COR when —W is —ON=$R^4$.

In one preferred embodiment, —W is —ON=$R^4$, and —ON=$R^4$ together constitute the residuum of an N-hydroxy cyclic imido group having 4 to about 8 carbon atoms as are present in an N-hydroxysuccinimido or N-hydroxyphthalimido moiety, and $R^1$ is COR.

In another preferred embodiment, —W is —ON=$R^5$, and —ON=$R^5$ together constitute an O,N-di-substituted oxime whose carbon-containing $R^5$ portion is derived from a group consisting of a $C_1$–$C_6$ ketone or aldehyde and a tetrahydropyranone derivative. $R^5$ is most preferably derived from a tetrahydropyran-4-one that can also contain a tetrahydropyran substituent.

A compound whose structure corresponds to that of the formula shown below constitutes yet another contemplated compound of this invention.

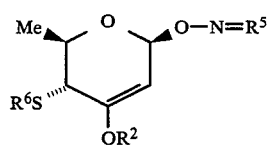

wherein $R^2$ is a moiety selected from the group consisting of tri-$C_1$–$C_6$ alkylsilyl, di-$C_1$–$C_6$ alkylphenylsilyl, and $C_1$–$C_6$ alkyldiphenylsilyl;

—ON=$R^5$ is an O,N-disubstituted oxime group in which $R^5$ is derived from a group consisting of a $C_1$–$C_6$ alkyl ketone or aldehyde, and a tetrahydropyranone derivative; and $R^6$ is selected from the group consisting of hydrogen, $C_1$–$C_6$ alkyl, benzoyl, m-chlorobenzoyl, $C_1$–$C_6$ alkyl oxycarbonyl and N-carbonyl imidazyl.

$R^6$ is most preferably hydrogen or m-chlorobenzoyl, and $R^2$ and $R^5$ are preferably as discussed above.

Also contemplated is a compound whose structure corresponds to that shown below in Formula VII.

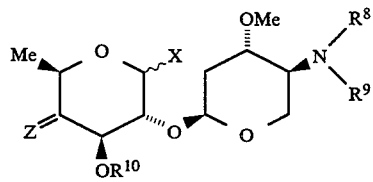

wherein $R^8$ is hydrogen or a selectively removable nitrogen atom protecting group such as FMOC, t-BOC, CBZ or NVOC as is used for protecting α-amino groups during peptide synthesis reactions;

$R^9$ is $C_1$–$C_6$ alkyl, with methyl, ethyl and iso-propyl being particularly preferred;

$R^{10}$ is hydrogen or a previously defined $R^2$ group;

Z is O or an oximino group that is the reaction product of the compound where Z=O with hydroxylamine or with an O-substituted hydroxylamine having up to 7 carbon atoms in the substituent such as O-benzylhydroxylamine or O-methylhydroxylamine; and X is selected from the group consisting of o-nitrobenzyloxy, benzyloxy, halo such as chloro, bromo or preferably fluoro, hydroxyl, and trichloroacetimido [OC(NH)CCl$_3$].

A disaccharide compound of Formula VII is useful as an intermediate and in forming a chimeric antibiotic with an aglycone as is shown in FIG. 14. Exemplary compounds whose structures correspond to Formula VII include Compounds 148, and 160–167.

A compound whose structure corresponds to that of Formula VIII, shown below, constitutes another embodiment of this invention.

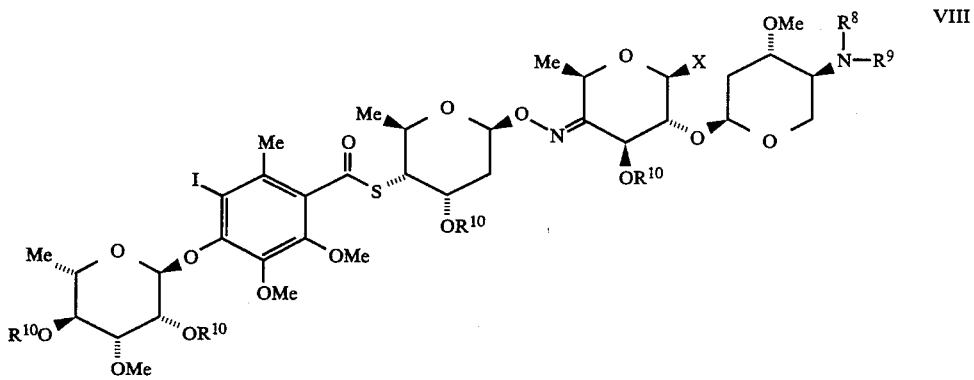

In the above formula, X is a leaving group, as can be selected from the group consisting of o-nitrobenzoxy, benzoxy, halo such as chloro, bromo, or preferably fluoro, and trichloractimido, and $R^8$, $R^9$ and $R^{10}$ ($R^{8-10}$) are as previously described, with $R^8$ preferably being FMOC. A compound of Formula VIII is particularly useful as an intermediate in preparing calicheamicin $\gamma_1^I$ and chimeras with DNA-cleaving compounds as are discussed hereinafter.

A chimer of Formula IX is also contemplated, wherein Z is a reacted DNA-cleaving compound discussed or shown herein, and $R^{8-10}$ are as discussed above, and in which $R^8$ is preferably FMOC.

A molecule that corresponds in structure to Formula XI, below, is also contemplated herein, wherein $R^{12}$ is $-OR^2$, o-nitrobenzyloxy, benzyloxy, halo such as chloro, bromo or more preferably fluoro or trichloroacetimido.

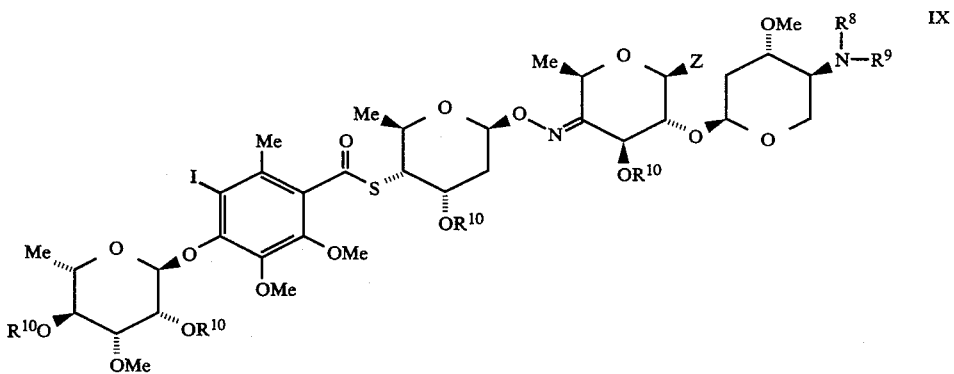

A compound of Formula X is also a contemplated chimer of the invention, where Z is a reacted DNA-cleaving compound other than calicheamicinone when $R^9$ is ethyl, and $R^9$ is defined above. The wavy line to the nitrogen of the hydroxylamine indicates that both of the α- and β-epimers are contemplated.

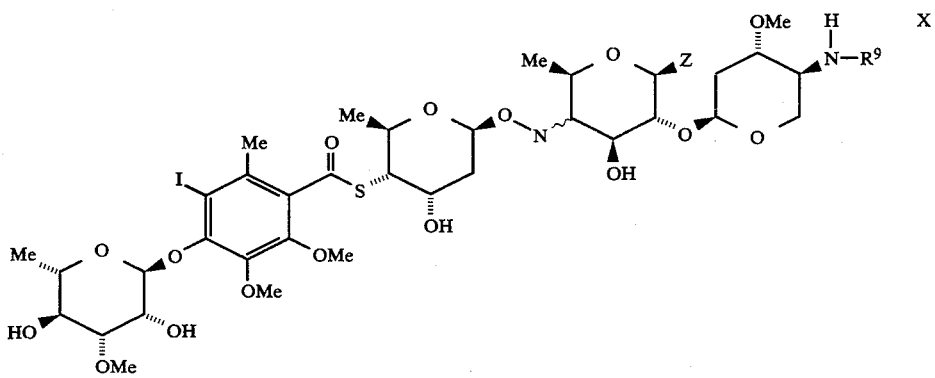

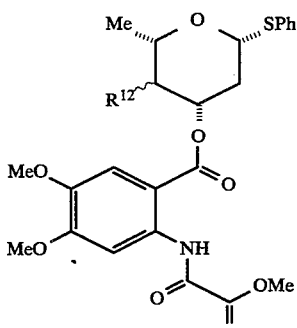

A molecule of Formula XI corresponds to the smaller esperamicin saccharide and is useful in preparing chimers as discussed elsewhere herein.

A method of forming (preparing) a compound whose structure corresponds to that of Formula A is also contemplated.

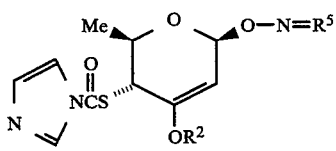

wherein $R^2$ is a moiety selected from the group consisting of tri-$C_1$–$C_6$ alkylsilyl, di-$C_1$–$C_6$ alkylphenylsilyl, and $C_1$–$C_6$ alkyldiphenylsilyl; and —ON=$R^5$ is an O,N-disubstituted oxime group in which $R^5$ is derived from a group consisting of a $C_1$–$C_6$ alkyl ketone or aldehyde and a tetrahydropyranone derivative;
comprising the steps of
a) heating the compound whose structure corresponds to that of Formula B

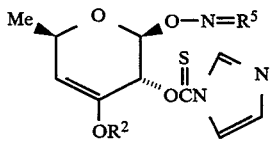

wherein $R^2$ and $R^5$ are defined above, in a liquid medium for a time period and at a temperature sufficient for that compound to rearrange to form a compound whose structure corresponds to that of Formula A.

The N-carbonylimidazyl group of a compound whose structure corresponds to that of Formula A is preferably replaced with hydrogen. It is also preferred that the compound of Formula A and the compound having hydrogen in place of N-carbonylimidazyl be recovered.

BRIEF DESCRIPTION OF THE DRAWINGS

In the drawings forming a portion of this disclosure.

In this figure and those that follow, the stereochemical configuration of saccharide ring substituents is shown as darkened wedge-shaped lines for bonds projecting upwardly from a ring ($\beta$-bonds) whereas dashes are utilized for bonds that project downwardly from a ring ($\alpha$-bonds). Ring-bonded hydrogens and hydrogen atoms without stereochemical significance are not shown. Me is methyl and Ph is phenyl in this figure and all others where those symbols are utilized. Abbreviations for previously undefined groups will be added in each description that follows, whereas previously defined abbreviations will not be redefined.

Figure 3:
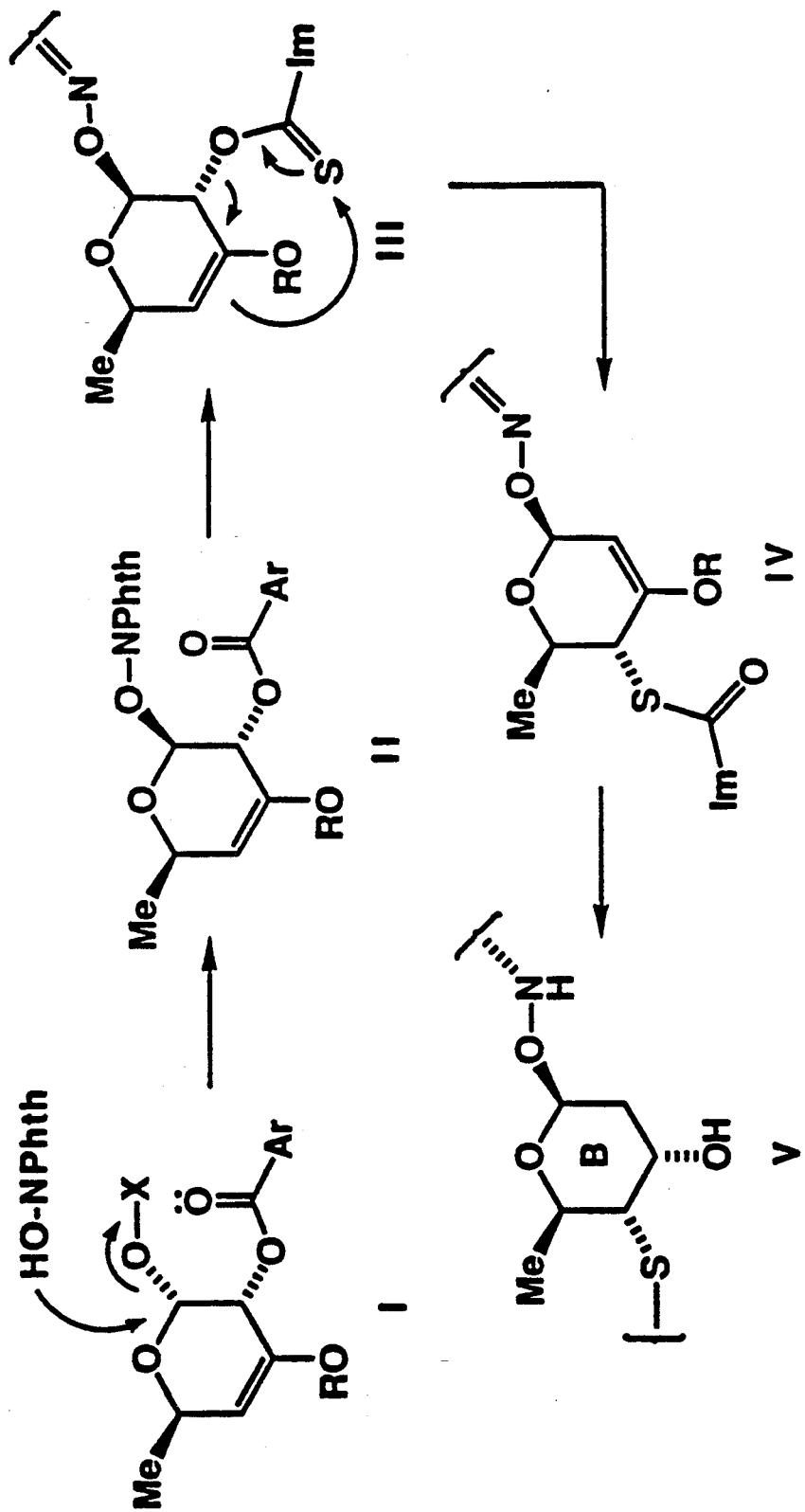

FIG. 3 illustrates reaction Scheme 1 and shows the general synthesis utilized herein for the preparation of the sulfur- and O-N-disubstituted hydroxylamine-containing B ring of a calicheamicin oligosaccharide. Curved arrows indicate the direction of bond formation and breakage. A bracket is utilized 10 to indicate that another group is doubly or singly bonded to the nitrogen atom. HO-NPhth is N-hydroxyl phthalimide, R is a generalized blocking group, Ar is an aromatic group such as m-chlorophenyl, and Im is imidazyl.

Figure 2:
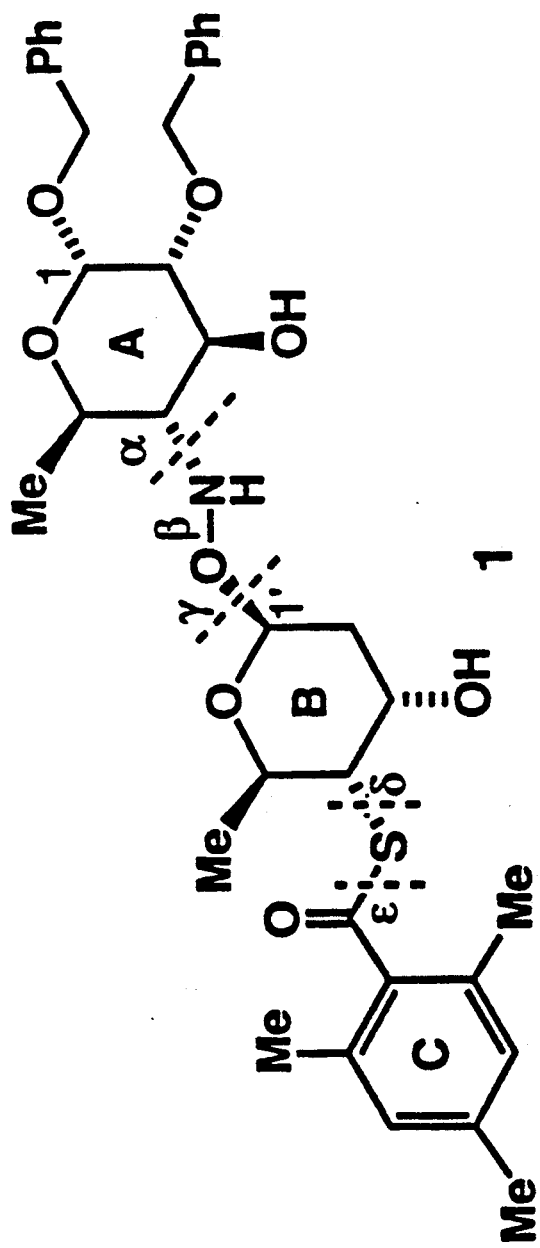
FIG. 2 illustrates the chemical structure for oligosaccharide Compound 1. The positions of glycosidic linkages in the two saccharide units are noted with numerals "1" and "1'". Key bonds linking the three rings are noted with dashed lines through the bonds and the Greek letters $\alpha$–$\epsilon$. The letters A, B and C indicate rings analogous to those present in calicheamicin.

FIG. 4 shown in three sheets, FIGS. 4-A, 4-B and 4-C, illustrates reaction Scheme 2 utilized in the preparation of Compound 1 of FIG. 2. Reaction steps a–r are discussed in the results and examples. In this scheme, Ac is acetyl, Ar is m-chlorophenyl, Si$^t$BuMe$_2$ is t-butyldimethylsilyl, Phth is phthalyl, PPh$_3$ is triphenylphosphine, and Bn is benzyl. The identity of each R, $R^1$, $R^2$ and X group is given for each numbered compound.

Figure 1:
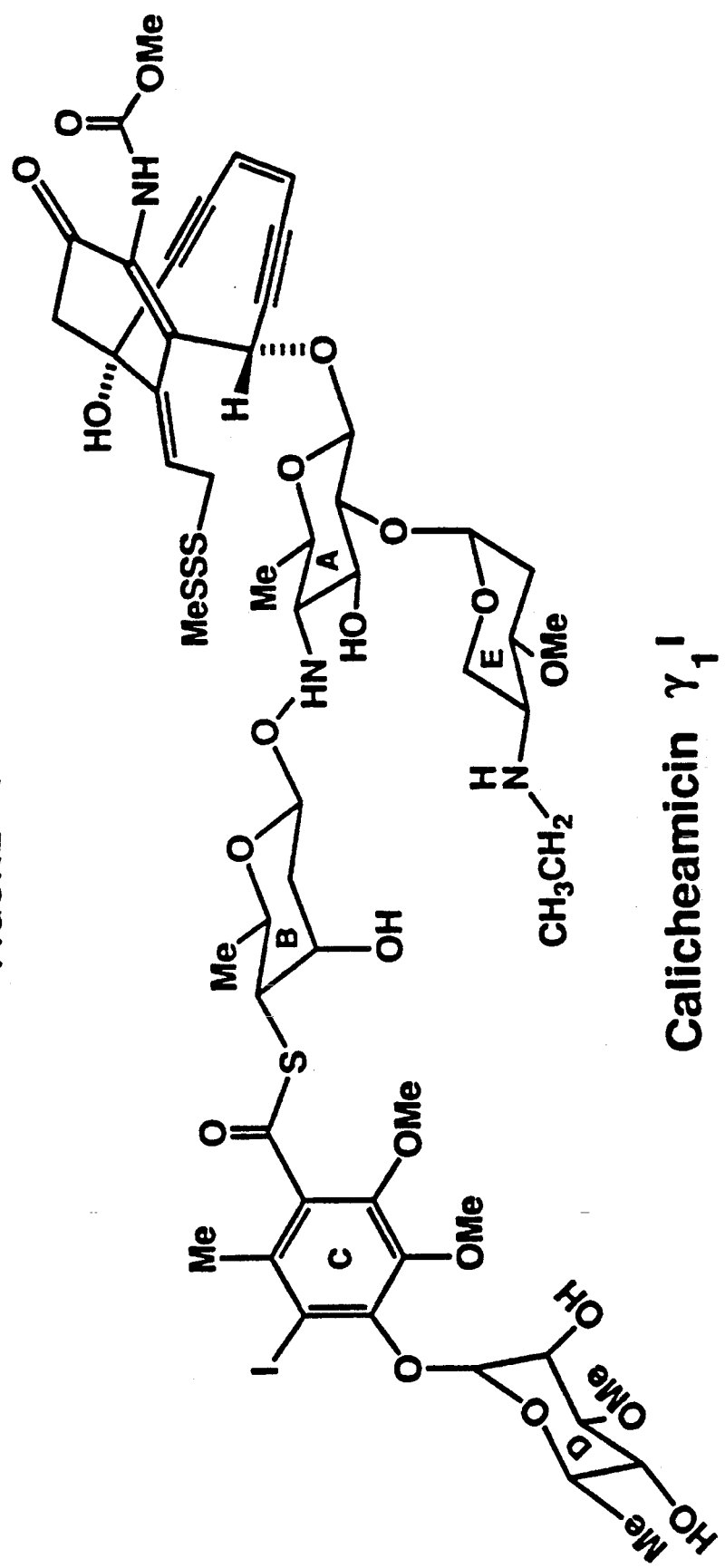
FIG. 1 illustrates the structural formula for calicheamicin $\gamma_1^I$ in which Me is methyl. Bonding of the junction between the oligosaccharide and aglycone portions is illustrated as being $\beta$. Hydrogen atoms bonded to ring carbon atoms other than at the glycosidic bond are not shown. The letters A–E designate rings in the oligosaccharide.
Figure 5:
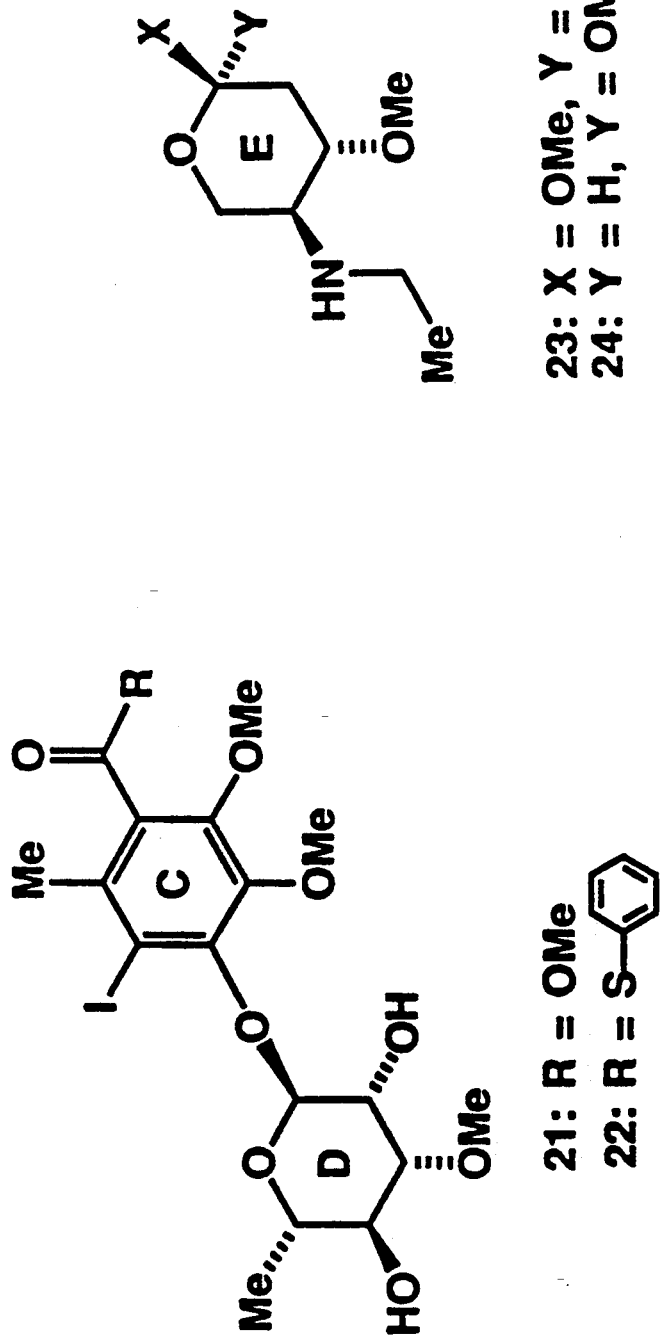

FIG. 5 illustrates structural formulas for Compounds 21, 22, 23 and 24 in which the identity of each R, X and Y group is as shown. The letters C, D and E indicate a correspondence of a depicted ring to the C, D and E rings of calicheamicin as shown in FIG. 1.

FIG. 6 shown in two sheets, FIGS. 6-A and 6-B, illustrates reaction Scheme 3 for the synthesis of Compounds 21 and 22 whose structures are shown in FIG. 5. In this scheme, C and D are used as before to designate correspondence of a ring to a calicheamicin oligosaccharide ring, and SiEt$_3$ is triethylsilyl. Reaction steps a–j are discussed for each numbered compound in the examples. Each group R, $R^1$, $R^2$ and X is defined as shown for each numbered compound.

Figure 7:
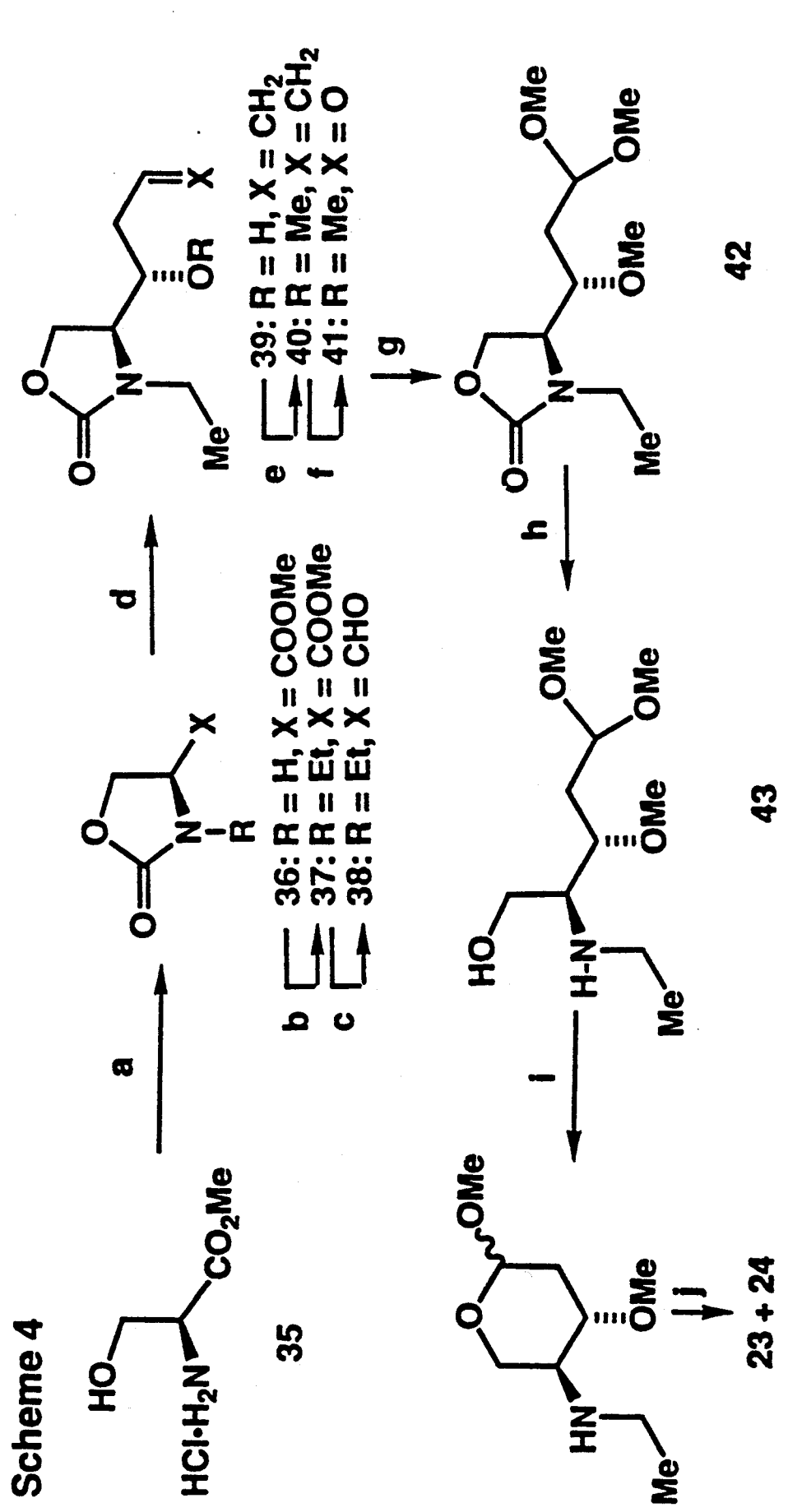

FIG. 7 illustrates reaction Scheme 4 for the synthesis of Compounds 23 and 24 whose structures are shown in FIG. 5. Reaction steps a–j are discussed for each numbered compound in the examples. The wavy line is utilized to depict the presence of both anomers.

FIG. 8, shown in two parts as FIGS. 8-A and 8-B, illustrates reaction Scheme 5 for the preparation of Compound 54, a 3-ring precursor to the 5-ring calicheamicin oligosaccharide, as well as being an analog of the esperamicin oligosaccharide. FMOC is 9-fluorenylmethyloxycarbonyl. Reaction steps a–k are discussed for each numbered compound in the examples. Each R, $R^1$, $R^2$ and X group is defined as shown for each numbered compound.

FIG. 9, shown in two sheets as FIGS. 9-A and 9-B, illustrates reaction Scheme 6 for the preparation of the calicheamicin oligosaccharide Compound 100 from Compound 55 (the acid chloride form of Compound 33 shown in FIG. 6) and Compound 54 shown in FIG. 8. Each R, $R^1$, $R^2$ and X group is defined as shown for each numbered compound. Reaction steps a-g are discussed for each numbered compound in the examples.

FIG. 10, shown in two parts as FIGS. 10-A and 10-B, illustrates reaction Scheme 7 for the preparation of an analog to Compound 54 that contains a photolabile o-nitrobenzyl (ONBn) group at the anomeric carbon atom from which a glycosidic bond to an aglycone can be formed after photolysis and suitable activation. This synthesis parallels the synthesis of Compound 54 shown in FIG. 8, with analogous numbered compounds having the same last two digits as their analogs in FIG. 8, and analogous reaction steps being lettered a-k. Each R, $R^1$ and $R^2$ is defined as shown for each numbered compound.

Figure 11:
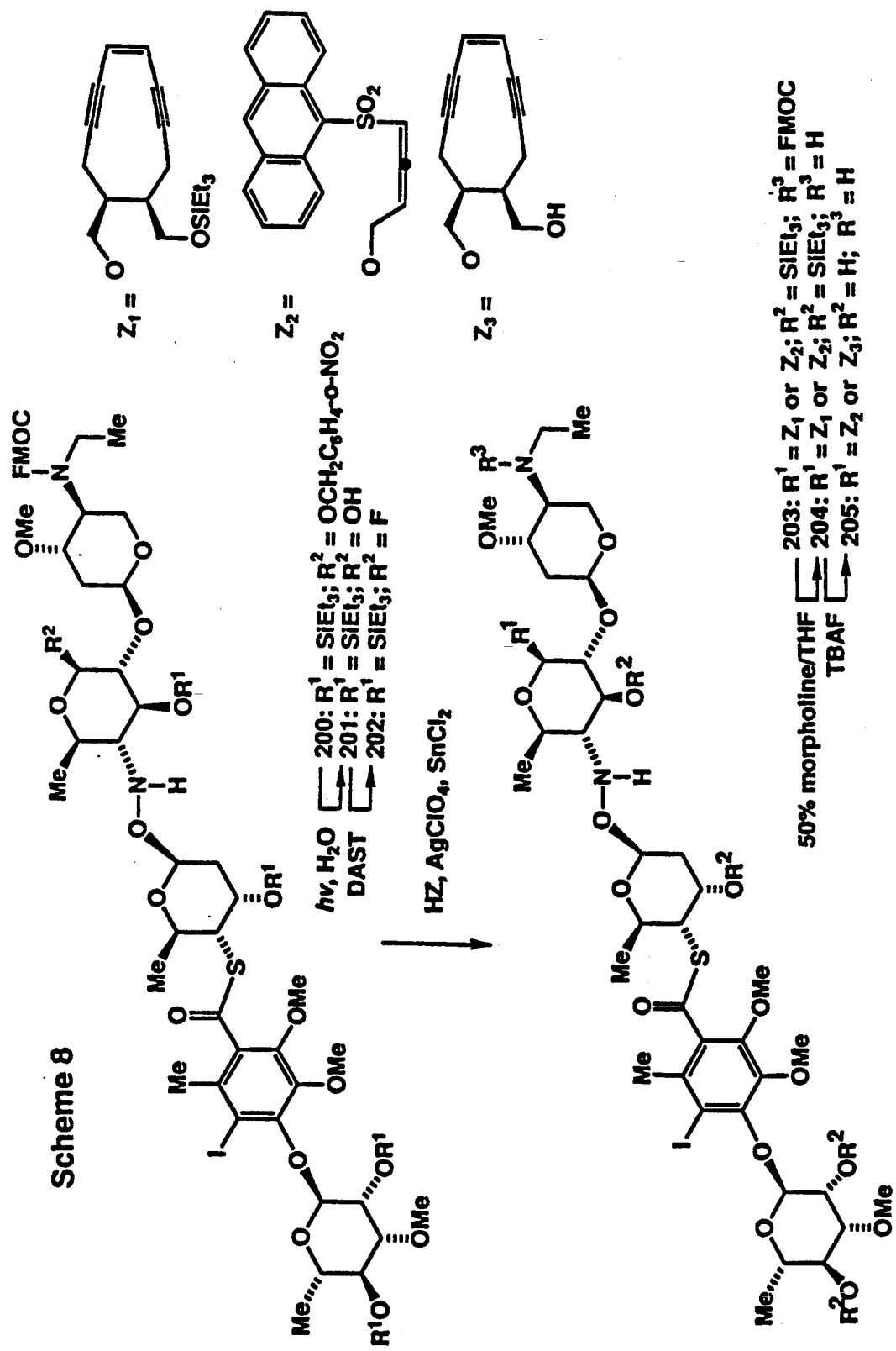

FIG. 11 illustrates reaction Scheme 8 for the preparation of a chimeric antibiotic using Compound 200, a 5-ring oligosaccharide analog of Compound 100 shown in FIG. 9, and DNA cleaving aglycone HZ. In this figure, hv is used to indicate an ultraviolet irradiation step, DAST is diethylaminosulfur trifluoride, THF is tetrahydrofuran, and TBAF is tetrabutylammonium fluoride. Each $R^1$, $R^2$, $R^3$, $Z_1$, $Z_2$ and $Z_3$ group is defined as shown for each numbered compound, whereas HZ is used to represent the alcohol form of aglycone portion $Z_1$, $Z_2$ or $Z_3$.

FIG. 12, shown in three parts as FIGS. 12-A, 12-B and 12-C, illustrates reaction Scheme 9 for the formation of a chimeric antibiotic Compound 226. Compounds 211 through 222 are analogs of Compounds 11 through 22 of FIGS. 4 and 5, with the last two digits of a number in this figure being the same as the two digit numbers in FIGS. 4 and 5 through Compound 220. Compounds 211 through 222 are also prepared in a manner analogous to Compounds 11 through 20. In this figure, PPTS is pyridinium p-toluene sulfonate, $^t$BuMeSiOTf is t-butyldimethylsilyl trifluoromethanesulfonate (triflate), DIBAL is diisobutylaluminum hydride, eq. is equivalent, and $Et_3SiOTF$ is triethylsilyl triflate. R, $R^1$, $R^2$, X, Y, $Z_1$, $Z_2$ and $Z_3$) groups are as shown for each numbered compound, with HZ representing the generalized alcohol form of aglycone portions $Z_1$, $Z_2$ and $Z_3$.

FIG. 13, shown in two sheets as FIGS. 13-A and 13-B, illustrates reaction Scheme 10 containing further reactions of Compound 148 to form Compound 167, a derivative of the calicheamicin A and E oligosaccharide rings. Substituents R, $R_1$, $R_2$, Z and X are identified for each compound. Other abbreviations are as defined before.

FIG. 14, shown in two sheets as FIGS. 14-A and 14-B, illustrates reaction Scheme 11 in which a dynemicin A analog DNA cleaving material, Compound 300, was reacted with Compound 163 to form diastereomeric chimeric antibiotic Compounds 307a and 307b. Substituents R, $R_1$ and $R_2$ are identified for each compound. The abbreviation Ph is for phenyl and $PhCH_2$ is benzyl.

FIG. 15, shown in two sheets as FIGS. 15-A and 15-B, illustrates reaction Scheme 12 in which a protected esperamicin precursor trisaccharide oxime containing a photolabile o-nitrobenzyl glycoside, Compound 256, was reacted to form a deprotected corresponding α-disubstituted 1-o-nitrobenzyl esperamicin trisaccharide, Compound 400. Abbreviations in this figure are as before.

FIG. 16, shown in two sheets as FIGS. 16-A and 16-B, illustrates reaction Scheme 13 for the formation of calicheamicin $\gamma_1^I$ from a protected oligosaccharide, Compound 401, and protected calicheamicinone precursor, Compound 402. Abbreviations in the figure are as before.

Figure 17:
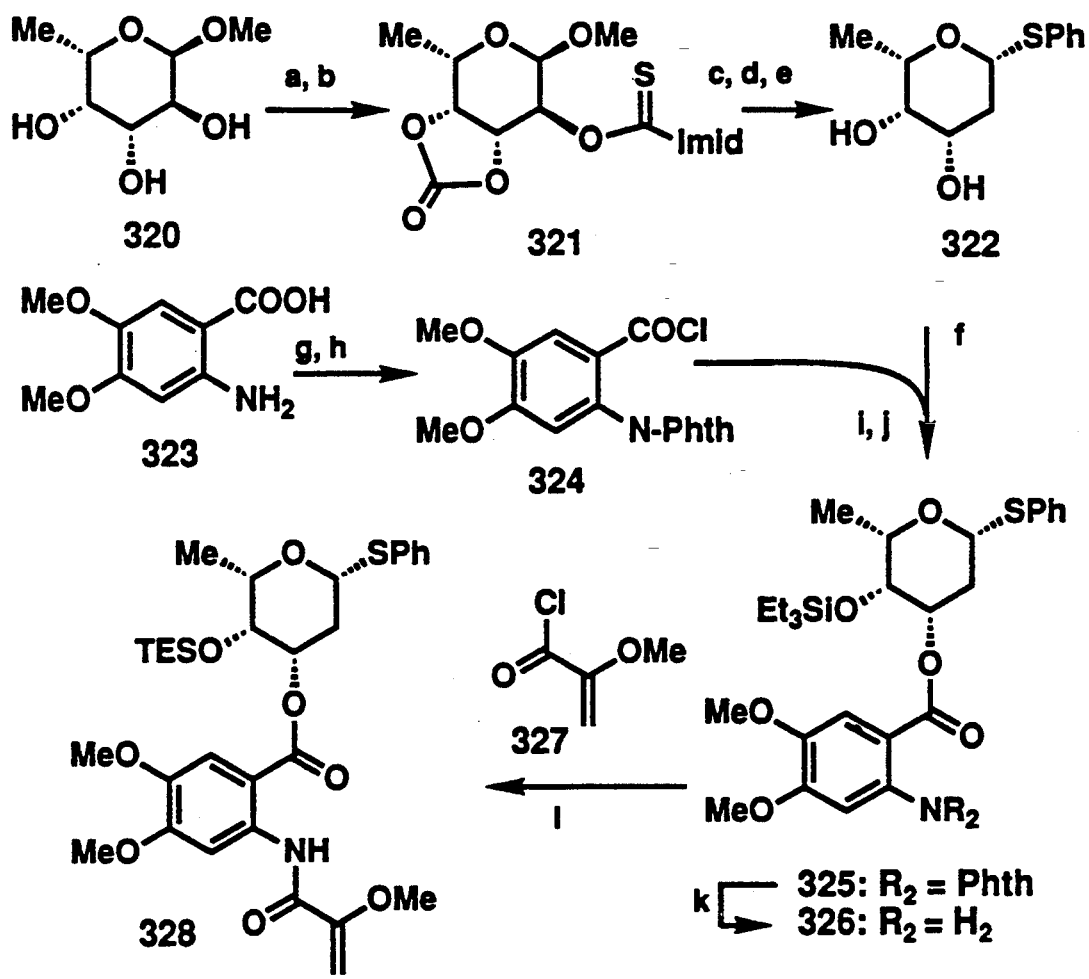

FIG. 17 illustrates reaction Scheme 14 for the synthesis of the smaller esperamicin saccharide, in protected TES (triethylsilyl) form. Abbreviations in this figure are as before, and imid is imidazyl.

Figure 18:
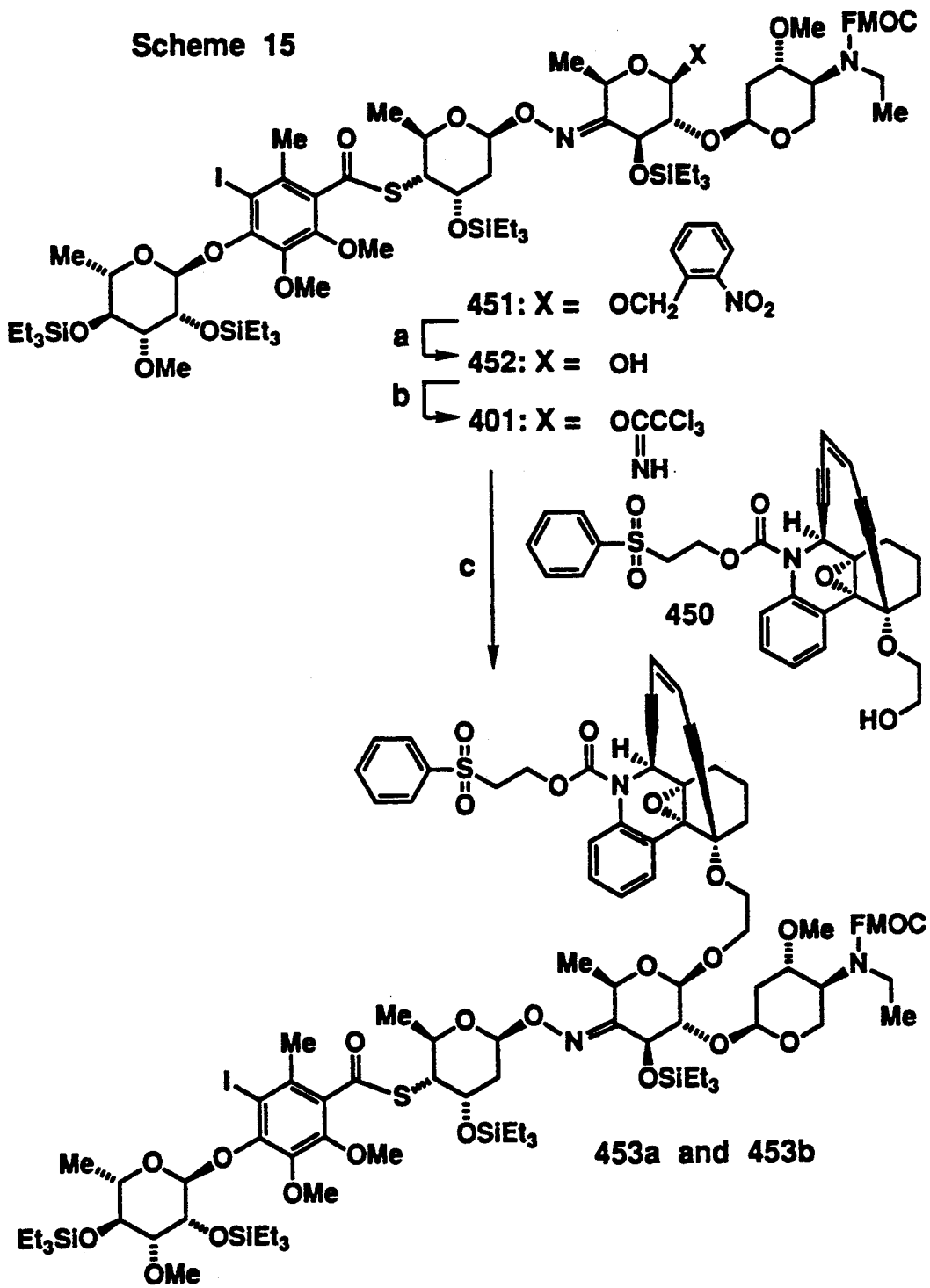

FIG. 18 illustrates reaction Scheme 15 for the synthesis of a protected chimer of the invention, Compounds 453a and 453b, from Compound 401, and DNA-cleaving agent 450. Abbreviations in this figure are as before.

Figure 19:
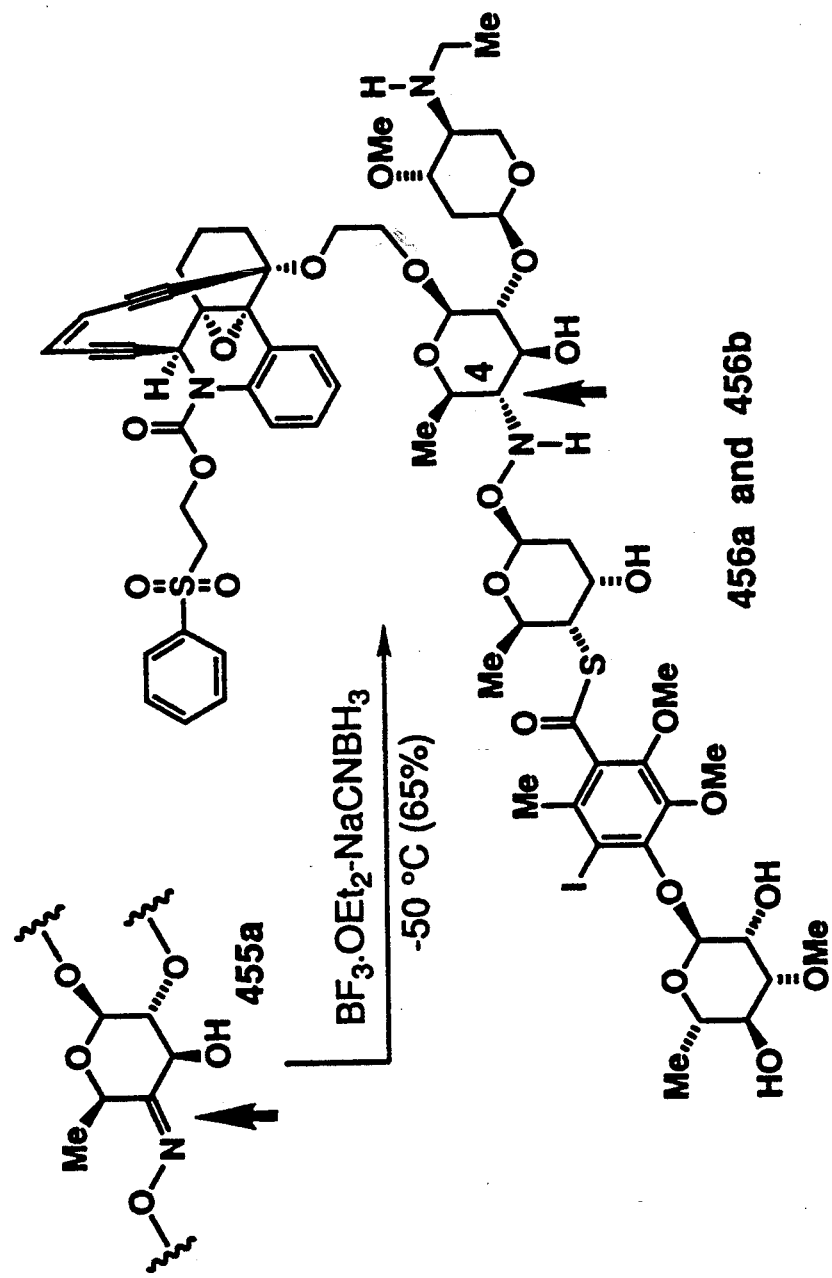

FIG. 19 illustrates Scheme 16 for the reduction of deprotected oxime chimer, Compound 455a, produced from protected chimer Compound 453a to form chimers 456a and 456b having the calicheamicin oligosaccharide epimers of C-4 of the A ring, only the natural α-epimer being shown. Only the oxime-containing portion of Compound 455a is shown and that bond is indicated by the arrow, as is the corresponding, reduced hydroxylamine bond in Compounds 456a and 456b. Wavy lines at bond termini indicate the presence of the remainder of the molecule.

The present invention has several benefits and advantages.

A salient benefit is that the thio- and O-hydroxylamine-substituted saccharide B ring present in calicheamicin and esperamicin has been prepared in a high yield synthesis.

Another benefit of this invention is that the B ring is prepared appropriately linked to the calicheamicin or esperamicin A and E ring disaccharide or analog.

A still further benefit is that a dynemicin A analog has been linked to the calicheamicin A and E ring disaccharide as a chimeric antibiotic.

A particular advantage of the invention is that synthesis of the complete calicheamicin oligosaccharide portion can be effected via the disclosed A, C, D, E and particularly B ring syntheses.

Yet another advantage of the invention is that the disclosed intermediates and methods can be used to prepare chimeric antibiotics.

Still further benefits and advantages of the invention will be apparent to the skilled worker from the disclosure that follows.

DETAILED DESCRIPTION OF THE INVENTION

As already noted, the present invention relates to the oligosaccharide portion of a calicheamicin or esperamicin, as well as to analogs and derivatives thereof. More particularly, the present invention relates to specific compound intermediates, analogs and derivatives thereof useful in preparing such oligosaccharides and methods of their preparation and use. 10 The compounds of particular interest herein are those utilized in the preparation of the sulfur- and oxygen-containing B ring, as well as the A and E ring disaccharide of the calicheamicin oligosaccharide, illustrated in FIG. 1. Esperamicin contains a similarly structured and substituted ring.

The chemical formulas shown herein are utilized to show both specific compounds and, where appropriate, generic classes of compounds. The compounds defined by those generic classes are referred to herein as analogs of each other or of a particularly enumerated or named compound.

Thus, for example, where $R^2$ is a $C_1$–$C_6$ trialkylsilyl group, two compounds are analogs of each other that are otherwise of the same structure and configuration and contain a triethylsilyl group in one and a t-butyldimethylsilyl group at the same position in the other. In a more concrete example, Compound 1 of FIG. 2 and Compound 221 of FIG. 12 are analogs.

Some compounds discussed herein contain a particular structure and substituents and others contain substantially the same structure and the same or analogous substituents plus at least one additional substituent group. A compound that contains that at least one added group is considered a derivative of the first compound having fewer groups. For example, Compound 16 of FIG. 4 contains two saccharide ring units, whereas Compound 54 contains two similar saccharide ring units plus one more saccharide ring unit as a substituent of one of these two saccharide rings. Compound 54 is thus a derivative of Compound 16. A derivative that contains one or more analogous substituents is considered a derivative, rather than an analog.

In each of the chemical formulas shown herein hydrogen atoms bonded to ring carbon atoms and carbon atom-bonded hydrogens that are stereochemically unimportant are not shown for improved clarity. Bonds that extend above the plane of the paper ($\beta$-bonds) are depicted by darkened wedge-shaped lines, whereas bonds extending below the plane of the paper are shown as dashed lines. Methyl, ethyl and butyl groups are frequently shown by the abbreviated designations Me, Et and Bu, respectively, whereas a benzyl group is shown as Bn, benzoyl as Bz, phenyl as Ph and a phthaloyl group is shown as Phth. These usages are those commonly found in the chemical literature.

One compound of particular interest is that whose structure corresponds to the Formula I below

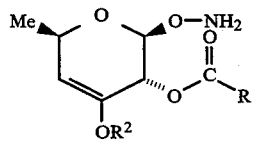

I wherein R is a moiety selected from the group consisting of hydrogen, $C_1$–$C_5$ alkyl, phenyl and m-chlorophenyl; and
$R^2$ is a moiety selected from the group consisting of tri-$C_1$–$C_6$ alkylsilyl, di-$C_1$–$C_6$ alkylphenylsilyl, and $C_1$–$C_6$ alkyldiphenylsilyl.

A particularly preferred compound of the above formula is Compound 10, shown in FIGS. 4, 8, 10 and 12. In that compound, R is a substituted phenyl group, more specifically m-chlorophenyl, and $R^2$ is a tri-$C_1$–$C_6$ alkylsilyl group, more specifically t-butyldimethylsilyl ($^t$BuMe$_2$Si). A triethylsilyl (Et$_3$Si) is also a particularly preferred $R^2$ substituent.

In reaction Scheme 2 shown in FIG. 4, the glycal, Compound 3, is oxidized with m-chloroperbenzoic acid (MCPBA), and the residuum of that per acid remains as an ester group (shown as OCOAr), which rearranges to form the 3-$\alpha$-ester of Compound 7 that is ultimately formed into the O-hydroxylamine, Compound 10. It is noted that any per carboxylic acid can be utilized for that sequence of steps, although MCPBA is preferred as it provides a superior yield, is stable to subsequent steps, and can be readily replaced for further steps.

In an alternative procedure, 1,2-anhydro-4,6-O-benzylidene-3-O-(t-butyldimethylsilyl)-$\beta$-D-altropyranose [Halcomb et al., *J. Am. Chem. Soc.*, 111:6661 (1989)] is reacted with a carboxylic acid to open the 1,2-epoxide and form the corresponding 2-$\beta$-hydroxy-1-$\alpha$-altropyranose ester in which the acid portion of the ester is a COR group as defined for Formula I. That ester is thereafter reacted (1) with NBS and AIBN; and (2) with Bu$_3$SnH and AIBN (as discussed in the preparation of Compound 2) to form an $\alpha$-1-o-acyl-3-trialkylsilylated-4-benzoyl-fucose. Swern oxidation [(COCl)$_2$, DMSO, Et$_3$N)] followed by in situ rearrangement (as is also discussed for the preparation of Compound 2) provides a compound of the above formula wherein R is as defined above.

Exemplary R groups include formyl, acetyl, propionyl, butyroyl, hexanoyl, benzoyl, m-chlorobenzoyl, and the like.

Preferred $R^2$ substituents are $C_1$–$C_6$ trialkylsilyl moieties which the alkyl groups can be the same or different. Particularly preferred $C_1$–$C_6$ trialkylsilyl moieties are triethylsilyl (SiEt$_3$) and t-butyldimethylsilyl ($^t$BuMe$_2$Si). Other useful silyl moieties include trimethylsilyl, triisopropylsilyl, t-butyldiphenylsilyl, iso-propyldimethylsilyl, 2-butyldimethylsilyl, t-hexyldimethylsilyl, phenyldimethylsilyl and diphenylmethylsilyl. Still further, useful, $R^2$ silyl groups as discussed above are well known to those skilled in the art. Silylating agents useful for preparing the $R^2$ silyl moieties are available from Petrarch Systems of Bristol, Pa., U.S.A., as well as from other suppliers.

As is seen from the schemes in FIGS. 4, 8, 10, 12, 13 and 14, a compound whose structure corresponds to that of Formula I is utilized to form an O,N-disubstituted oxime that links precursors to the A and B rings together. That disubstituted oxime is subsequently reduced to form the O,N-disubstituted hydroxylamino group that can link the A and B rings in the oligosaccharide.

Another particularly preferred compound of the invention corresponds in structure to that shown in Formula II below

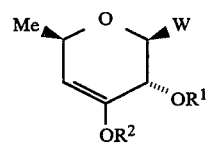

II wherein $R^2$ is as before discussed;
$R^1$ is hydrogen or COR, where R is as before described; i.e., hydrogen, $C_1$–$C_5$ alkyl, phenyl or m-chlorophenyl; and
—W is the residuum (reaction product) of (i) an N-hydroxy cyclic imido group or (ii) an O,N-disubstituted oxime group. In the above formula, —W is —ON=$R^4$ or —ON=$R^5$ so that N=$R^4$ and N=$R^5$ represent two bonds between a nitrogen atom and $R^4$ or $R^5$, respectively.

When —W forms the residuum of an N-hydroxy cyclic imido group, —ON=$R^4$, $R^4$ contains 4 to about 8 carbon atoms Thus, —ON=$R^4$ together form the residuum of an N-hydroxysuccinimido, N-hydroxy(methylsuccinimido) or N-hydroxyphthalimido group. In addition, when —W is —ON=$R^4$, $R^1$ is COR.

A particularly preferred compound whose structure corresponds to that of Formula II is Compound 9 shown in FIG. 4, wherein —ON=R$^4$ forms the residuum of an N-hydroxyphthalimodoyl group, R$^1$ is m-chlorobenzoyl and R$^2$ is Si$^t$BuMe$_2$. As is seen from FIG. 4, Compound 9 and the other compounds of the above formula are precursors to Compound 10 and the other compounds whose structures are embraced by the Formula I.

When —W forms the residuum of an O,N-disubstituted oxime group, R$^5$ is a carbon-containing portion that is derived from a C$_1$–C$_6$ alkyl ketone or aldehyde; i.e., a C$_1$–C$_6$ alkylidene or a tetrahydropyranone derivative. Exemplary tetrahydropyranone derivatives include a calicheamicin or esperamicin A ring or A and E ring disaccharide, such as those illustrated herein. In this instance, R$^1$ is as before defined.

Preferred compounds of Formula II in which R$^3$ is R$^5$ are Compounds 11–13 of FIG. 4, Compound 49–51 of FIG. 8, Compounds 149–151 of FIG. 10 and Compounds 211–213 of FIG. 12. Each of those compounds includes an R$^5$ group derived from a substituted tetrahydropyranone derivative, and particularly a substituted tetrahydropyran-4-one derivative.

As can be seen from the above-numbered compounds of FIGS. 4, 8, 10 and 12, the tetrahydropyranone can have C$_1$–C$_6$ alkyl substituents, e.g. methyl, ethyl or hexyl, as well as hydroxyl, O-benzyl and O-silyl; i.e., an R$^2$ group, an o-nitrobenzyloxy (ONBn) and another tetrahydropyranose derivative as substituent groups. Preferably, the substituted tetrahydropyranone derivative is itself substituted with but a single further tetrahydropyranose substituent. Those depicted oligosaccharide compounds are precursors for larger oligosaccharides, as can be utilized in the preparation of chimeric antibiotics, discussed hereinafter. A compound whose structure corresponds to Formula II in which R$^5$ is a tetrahydropyran-4-one derivative that is itself substituted at the 2-position with a substituted tetrahydropyran is a precursor to the esperamicin trisaccharide.

R$^5$ can also be derived from a C$_1$–C$_6$ alkyl ketone or aidehyde; i.e., C$_1$–C$_6$ alkylidene. Exemplary of such materials are formaldehyde, acetaldehyde, butyraldehyde, hexylaldehyde, acetone, 2-butanone, 3-hexanone and cyclopentanone. The isopropylidene derivative, prepared from acetone, has been prepared, and a further derivative otherwise similar in structure to Compound 14 of FIG. 4 has been used as a model compound in the rearrangement of the thiocarbonylimidazyl derivative to a compound analogous in structure to Compound 15.

Yet another compound of interest herein has a structure that corresponds to that of Formula III, below

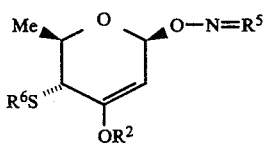

wherein R$^2$ and R$^5$ are as described before, and R$^6$ is selected from the group consisting of hydrogen, C$_1$–C$_6$ alkyl, benzoyl, m-chlorobenzoyl, C$_1$–C$_6$ alkyl oxycarbonyl and N-carbonyl imidazyl. R$^5$ here is preferably a tetrahydropyranone derivative as discussed before.

Particularly preferred compounds whose structures correspond to Formula III include Compounds 15–17 of FIG. 4, Compounds 53 and 54 of FIG. 8, Compound 56 of FIG. 9, Compounds 153 and 154 of FIG. 10 and Compounds 215, 216 and 217 of FIG. 12. Those compounds illustrate R$^6$ groups that include hydrogen, thiocarbonyl imidazyl and m-chlorobenzoyl.

As can be seen from the above exemplary substituted R$^6$ benzoyl groups, substituents on the benzoyl group can include C$_1$–C$_6$ alkoxy such as methoxy, ethoxy, iso-propoxy and cyclohexyloxy, C$_1$–C$_{6x}$alkyl such as methyl, ethyl, iso-propyl, sec-butyl and 2-hexyl, halo such as iodo, bromo, chloro and fluoro, and a glycosyl-linked substituted tetrahydropyranose derivative such as the D ring of calicheamicin.

R$^6$ can also be a C$_1$–C$_6$ alkyl group, in which case, the ultimately prepared oligosaccharide corresponds to the esperamicin oligosaccharide, a derivative or analog thereof. Exemplary C$_1$–C$_6$ alkyl groups are methyl, ethyl (as is present in calicheamicin $\gamma_1^I$), iso-propyl (as is present in the esperamicin oligosaccharide), butyl, sec-butyl, cyclohexyl, and 2-hexyl. These C$_1$–C$_6$ alkyl groups also exemplify the C$_1$–C$_6$ alkyl group portion of a C$_1$–C$_6$ alkyl oxycarbonyl group so that SR$^6$ is C$_1$–C$_6$ alkyl thiocarbonate.

An R$^6$ C$_1$–C$_6$ alkyl group can be prepared from the corresponding compound of Formula III where R$^6$ is hydrogen, the mercaptan, by alkylation with an above C$_1$–C$_6$ alkyl iodide or trifluorosulfonate (triflate, Tf) in the presence of a relatively mild, non-nucleophilic base such as K$_2$CO$_3$.

A method of preparation of a compound whose structure corresponds to that of Formula IV is also contemplated

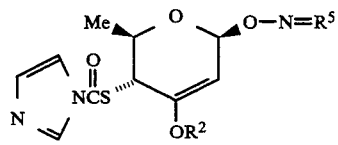

wherein R$^2$ and R$^5$ are as defined before, and R$^5$ is preferably a tetrahydropyranone derivative.

In accordance with this method, a compound whose structure corresponds to that of Formula V

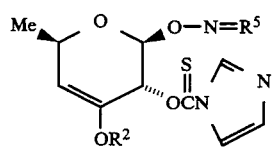

wherein R$^2$ and R$^5$ are as defined before is heated in a liquid composition for a time period and at a temperature sufficient for a compound whose structure corresponds to that of Formula IV to form. The imidazyl group shown in Formulas IV and V can also be a C$_1$–C$_6$ alkoxy group.

The liquid composition is typically an aprotic solvent. Exemplary of such solvents are toluene, xylene, acetonitrile, and ethylene glycol diethyl ether. 10 The maximum temperature to which the liquid composition is heated is, at atmospheric pressure, limited by the boiling point of the composition. However, a liquid composition need not be utilized at its reflux temperature. Generally, a temperature above room temperature (18–25 degrees C.) to about 140 degrees C. can be used, with a temperature of about 100 to about 120 degrees C. as is obtained with toluene at reflux being preferred.

As with most reactions, the above rearrangement proceeds more rapidly at higher than at lower temperatures. For laboratory 0.1–0.5 gram scale reactions, the rearrangement is substantially complete when carried out at about 110 degrees C. for 0.5–1 hour.

In preferred practice, the rearrangement product is recovered at the end of the reaction.

It is also preferred that the N-carbonylimidazyl or $C_1$–$C_6$ alkoxy carbonyl group of a compound whose structure corresponds to that of Formula IV be replaced with hydrogen. This step is carried out by reacting the rearranged thio N-carbonylimidazyl or thiocarbonate group with NaSMe at room temperature or a similar reagent to provide the corresponding mercaptan. The thus produced mercaptan is also preferably isolated and is generally reacted quickly with an alkylating or acylating agent.

In a particularly preferred embodiment of the above method, a compound whose structure corresponds to that of Formula V is prepared by reacting a compound whose structure corresponds to that of Formula VI, wherein $R^2$ and $R^5$ are as before defined,

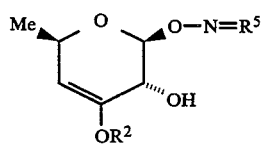

VI with thiocarbonyl diimidazole in a liquid composition as a reaction mixture using aprotic solvent such as acetonitrile. Where a thio carbonate as in Formula IV is formed, a $C_1$–$C_6$ alkyl thiochloroformate is reacted in the presence of a base such as pyridine. The reaction mixture is maintained for a time period sufficient for a compound corresponding in structure to that of Formula V to form, and that compound is preferably recovered.

The reaction is typically carried out at a temperature of about zero to about 30 degrees C., and preferably at about ambient room temperature, about 18–25 degrees C. When carried out at room temperature, the reaction is maintained for about 18 to about 24 hours to maximize yield. At lower temperatures, the reaction proceeds more slowly, whereas at higher temperatures, the rearrangement to a compound corresponding in structure to that of Formula IV competes and diminishes the yield.

A compound corresponding in structure to Formula IV can also be directly prepared by reacting a liquid composition containing a compound of Formula VI with thiocarbonyl diimidazole at a temperature above about 30 degrees C. to about 140 degrees C., and maintaining the reaction mixture so formed for a time period sufficient to form the desired material. Direct formation of a thiocarbonate is carried out similarly using a $C_1$–$C_6$ alkyl thiochloroformate and a base such as pyridine.

Another group of particularly preferred compounds has a structure that corresponds to that of Formula VII

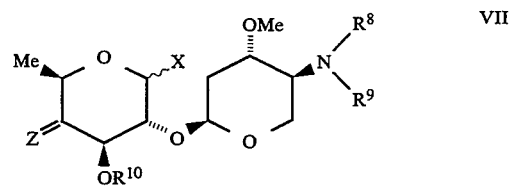

VII wherein $R^8$ is hydrogen or a selectively removable nitrogen atom protecting group such as FMOC (9-fluorenylmethyloxycarbonyl), t-BOC (t-butyloxycarbonyl), CBZ (carbobenzyloxy), or NVOC (nitroveratryloxycarbonyl) as is used for protecting α-amino groups during peptide synthesis reactions;

$R^9$ is $C_1$–$C_6$ alkyl, with methyl, ethyl and iso-propyl being particularly preferred;

$R^{10}$ is hydrogen or a previously defined $R^2$ group;

Z is O or a oximino group that is the reaction product of the compound where Z=O with hydroxylamine or an O-substituted hydroxylamine containing up to 7 carbon atoms such as O-benzylhydroxylamine or O-methylhydroxylamine; and X is selected from the group consisting of o-nitrobenzyloxy, benzyloxy, halo such as chloro, bromo or preferably fluoro, hydroxyl, and trichloroacetimidato [OC(NH)CCl$_3$].

A disaccharide compound of Formula VII is useful as an intermediate and in forming a chimeric antibiotic with an aglycone as is shown in FIGS. 10, 13 and 14. A compound of Formula VII can also be used with an aglycone illustrated in FIGS. 11 and 12 to form a chimer. Exemplary compounds whose structures correspond to Formula VII include Compounds 148, and 160–167.

Thus, exemplary chimers prepared from a compound of Formula VII are Compounds 307a and 307b that are shown in FIG. 14. Another compound of Formula VII is the esperamicin trisaccharide illustrated in FIG. 15 as an o-nitrobenzyloxy derivative. Compound 167 of FIG. 13 is another compound of Formula VII, as is Compound 154 of FIG. 10.

Still further compounds of the invention include the calicheamicin $\gamma_1^I$ oligosaccharide, or a precursor thereto. One such group of compounds corresponds in structure to Formula VIII, below, in which $R^{8-10}$ are previously defined, and X is a leaving group, as can be selected from the group consisting of o-nitrobenzyloxy, benzyloxy, halo such as chloro, bromo or more preferably fluoro and trichloroacetimidato as exemplary. $R^8$ is preferably FMOC. A compound of Formula VIII is useful in preparing a chimer with a DNA-cleaving compound; i.e., aglycone, as is illustrated in FIGS. 11, 18 and 19, and discussed herein.

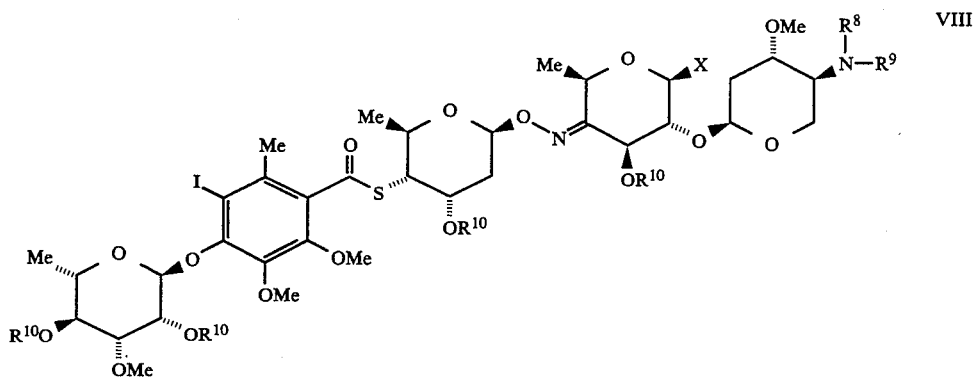

An exemplary chimer produced using a compound of Formula VIII and a DNA-cleaving aglycone (HZ) is illustrated by a compound of Formula IX, below, wherein $R^{8-10}$ are as discussed above and Z is a reacted DNA-cleaving aglycone. An exemplary compound of Formula IX is illustrated in FIG. 18.

The DNA-cleaving aglycone portion is preferably linked to the saccharide portion of the chimer via an ether linkage and can thus be referred to as O-linked. Other methods of linkage such as via ester and specialized linking groups as are well known for linking drugs to antibodies can also be used. See, for example, Muller et al., *Bioconjugate Chem.*, 2:325 (1990) and Reisfeld et al., *Immunol. Allergy Clin. N.Am.*, 11:341 (1991), and the citations therein.

Exemplary DNA-cleaving aglycones include those illustrated as $Z_1$, $Z_2$ and $Z_3$ in the figures, the dynemycin analog Compound 450 of FIG. 18, the dynemicin analog Compound 458, discussed hereinafter, as well as other DNA-cleaving aglycones such as daunorubicin and doxorubicin. As is illustrated in Table 1 hereinafter, a chimer corresponding to Formula IX, Compounds 455a and 455b, where Z is derived from Compound 450, $R^8$ and $R^{10}$ are each hydrogen exhibited considerable potency against several cancer cell lines.

More preferred is a chimer in which the oxime bond of a compound of Formula IX is reduced to the hydroxylamine. Such a chimer corresponds in structure to Formula X, below, where Z and $R^9$ are as defined above except that Z cannot be calicheamicinone when $R^9$ is ethyl, and the wavy line to the hydroxylamine indicates both the α- and β-epimers. The α-epimer at C-4 of the A ring, shown in the bracketed partial structure of Formula Xa, is preferred. The compound obtained when Z is a reacted calicheamicinone and $R^9$ is ethyl is calicheamicin $\gamma_1^I$, a previously known material.

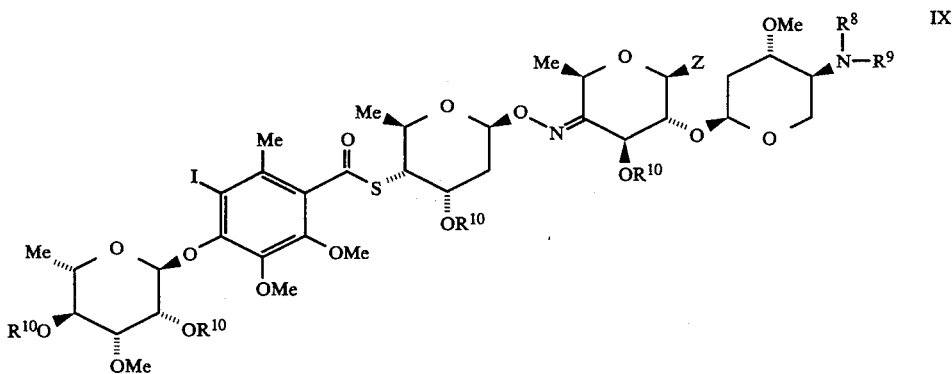

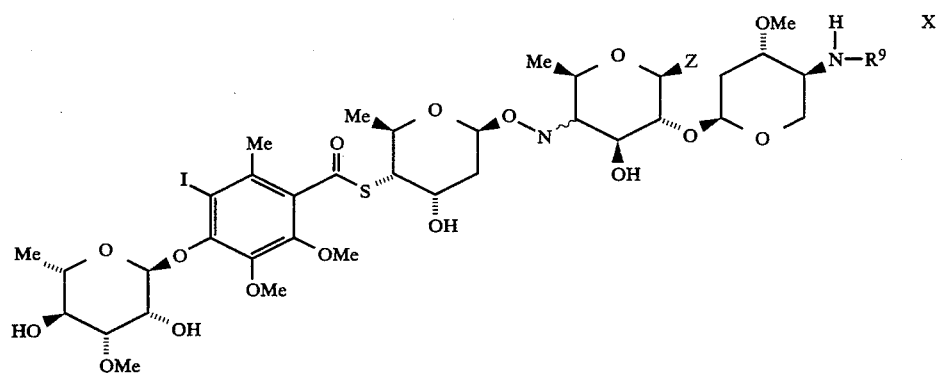

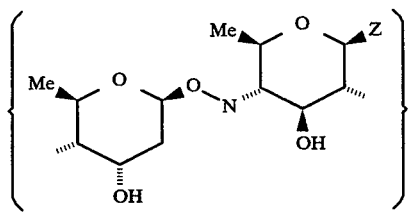

Xa

Exemplary chimers of Formula X are illustrated in FIGS. 11 and 19 and by Compounds 457a and 457b. The results of Table 1 illustrate potencies for chimer Compounds 456a and 456b that utilize the α- and β-epimers, respectively, of a compound of Formula X.

Yet another molecule useful in preparing chimers corresponds in structure to Formula XI, wherein $R^{12}$ is —$OR^2$, o-nitrobenzyloxy, benzyloxy, halo such as chloro, bromo or more preferably fluoro or trichloroacetimidato, wherein the wavy line to $R^{12}$ indicates both epimers.

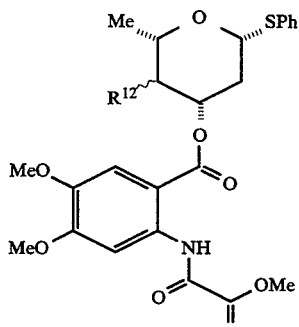

XI

A molecule of Formula XI corresponds to the smaller esperamicin saccharide and is useful in preparing chimers as discussed elsewhere herein.

An exemplary compound of Formula XI is Compound 328, whose structure is shown in FIG. 17, as is a scheme for its synthesis. The synthesis of Compound 328 is discussed in greater detail hereinafter.

The compounds, analogs and derivatives discussed herein are particularly useful in preparing oligosaccharide portions of a chimeric antibiotic or chimer by reaction with an aglycone, and preferably a DNA cleaving aglycone. The produced chimer has in vitro DNA cleaving activity as well as activity against microorganisms such as Escherichia coli, Klebsiella pneumoniae, Staphyloccus aureus, and Saccharomyces cerevisiae, and is also a useful agent in treating certain cancer cells such as P-388 leukemia, Molt-4 leukemia, and B16 melanoma cells. These chimers thus have biological activities similar to those exhibited by calicheamicin and esperamicin. Exemplary chimer syntheses are discussed hereinafter.

A chimeric antibiotic is utilized as an active agent in an aqueous pharmaceutical composition in which it is dissolved or dispersed. The chimer is thus dissolved or dispersed in a pharmaceutically tolerable diluent such as water, water/ethanol, normal saline or a buffered aqueous solution such as phosphate-buffered saline or within vesicles as are well known. Exemplary further diluents can be found in Remmington's Pharmaceutical Sciences, Mack Publishing Co., Easton, Pa. (1980).

The chimeric antibiotic is present in such a pharmaceutical composition in an amount effective to achieve a desired result. For example, where in vitro DNA cleavage is the desired result, a compound of the invention can be utilized in an amount sufficient to provide a concentration of about 1.0 to about 500 micromolar ($\mu$M) with a DNA concentration of about 0.02 $\mu$g/$\mu$l. As a cytotoxic (anti-tumor) agent, an effective amount of a chimer is about 0.2 to about 15 $\mu$g per kilogram of body weight. For use as an antimicrobial agent, a chimer is utilized at about 0.01 to about 50 $\mu$g/ml. The particular concentration or dosage can vary with the particular chimer (both as to oligosaccharide and aglycone) utilized as well as the particular target; i.e., DNA, tumor, microbe, as is well known.

Particular antimicrobial and anti-tumor assays can be carried out as described in U.S. Pat. No. 4,837,206, whose disclosures are incorporated by reference, and U.K. patent application G.B. 2,179,649A, and as discussed hereinafter. DNA cleavage can be assayed as discussed in Nicolaou et al., J. Am. Chem. Soc., 110:7247 j(1988) or Zein et al., Science, 240:1198 (1988).

Results

The highly unusual structures of the esperamicins and calicheamicins, of which calicheamicin $\gamma_1^I$ is the most prominent member [Lee et al., J. Am. Chem. Soc., 109:3464 (1987)], coupled with their phenomenal biological activity have spurred a flurry of investigations. Whereas most of the synthetic efforts in this area have focused on biological mimics [Nicolaou et al., J. Am. Chem. Soc., 110:4866 (1988)] and the bicyclic enediyne skeleton, [Haseltine et al. J. Am. Chem. Soc., 110:7638 (1989); Danishefsky et al., J. Am. Chem. Soc., 110:6890 (1988); Danishefsky et al., Tetrahedron Lett., 29:4681 (1988); Screiber et al., Tetrahedron Lett., 30:433 (1989); Screiber et al., J. Am. Chem. Soc., 110:631 (1988); Magnus et al., Tetrahedron Lett., 30:1905 (1989); Magnus et al., J. Chem. Soc. Commun., 916 (1989); Magnus et al., J. Am. Chem. Soc., 110:6921 (1988); Magnus et al., J. Am. Chem. Soc., 110:1626 (1988); Tomioka et al., Tetrahedron Lett., 30:851 (1989)] reports relating to the oligosaccharide fragment have been few [(a) for the synthesis of the aromatic system of calicheamicin $\gamma_1^I$ see: Nicolaou et al, Angew. Chem. Int. Ed. Engl., 27:1097 (1988); (b) for the synthesis of a methyl-a-glycoside of the thio sugar see: Van Laak et al, Tetrahedron Lett., 30:4505 (1988); (c) for a synthesis of the esperamicin isopropylamino sugar see: Golik et al., Tetrahedron Lett., 30:2497 (1989); for a synthesis of the calicheamicin $\gamma_1^I$ ethylamino sugar see: Kahne et al., Tetrahedron Lett., 31:21 (1990)].

A. The ABC Oligosaccharide

The results below describe the first synthetic study that provides solutions to the stereoselective construction of the crucial bonds a-ε shown in FIG. 2 that are present in the calicheamicin $\gamma_1^I$ oligosaccharide, and which synthesis delivers the ABC oligosaccharide skeleton in optically active form.

On close inspection of the oligosaccharide fragment of calicheamicin $\gamma_1^I$, one identifies the following challenging synthetic features (shown in FIG. 2): (a) the unusual alkoxylamine bond $\beta$, linking carbohydrate units A and B via bonds $\alpha$ and $\gamma$; (b) the $\beta$-stereochemistry of the glycoside bond $\gamma$, which taken in combination with the 2-deoxy nature of saccharide B, offers a unique challenge to synthetic construction; (c) the sulfur bridge, linking carbohydrate unit B with a heavily substituted aromatic system via bonds $\delta$ and $\epsilon$; and (d) the $\alpha$-stereochemistry of the N- and S-bearing stereogenic centers of saccharide units A and B respectively.

The results obtained provide clean, and rather novel solutions to all the above challenges. The synthetic design was based on the retrosynthetic disconnections indicated in FIG. 2 that led to thiocarbonyldiimidazole ($Im_2C=S$) as the sulfur source, N-hydroxyphthalimide (HO-NPhth) as the origin of the alkoxyamino group and precursors to rings A, B and C as potential starting points.

Scheme 1 (FIG. 3) outlines the synthetic strategy as designed from the above analysis, and which, in addition to solving the above mentioned problems, avoids a potentially difficult deoxygenation step to generate the methylene group of the B ring. Thus, intermediate I (Scheme 1 of FIG. 3) was designed with an ester group at position-2 to assure the desired stereochemical outcome of the glycosidation reaction (I→II, $\beta$-stereochemistry) as well as a means to stereoselectively deliver the sulfur atom at position-4 via a sigmatropic rearrangement (II→III→IV). Intermediate IV was then expected to serve as a precursor to V.

Scheme 2 (FIG. 4) outlines the reaction sequence leading to target Compound 1 shown in FIG. 2. Thus, following selective deprotection (DIBAL, 72 percent) of the diester Compound 2, expoxidation of Compound 3 with m-chloroperoxybenzoic acid (MCPBA) followed by regio- and stereoselective epoxide opening by m-chlorobenzoic acid afforded Compound 4 in 55 percent yield.

Selective silylation [-Si$^t$BuMe$_2$, 67 percent] of the 3-hydroxyl group of Compound 4 followed by exposure to Swern conditions resulted in the formation of enone Compound 6 via an oxidation-elimination sequence (88 percent). 1,2-Reduction of enone Compound 6 using ZnBH$_4$-NH$_4$Cl in ether [in the absence of NH$_4$Cl, silyl group migration from 0-3 to 0-2 was a competing process following initial 1,2-reduction of the enone] proceeded smoothly from the $\beta$-face, and was followed by the expected, in situ, ester migration to afford the desired $\alpha$-lactol Compound 7 in good yield (about 8:1, $\alpha$:$\beta$ ratio $^1$H NMR). [For an example of 1,2-ester migration in a cis-1-O-acyl-2-hydroxy sugar see: Pederson et al., *J. Am. Chem. Soc.*, 82:3215 (1960).]

Rapid work-up of Compound 7 followed by immediate addition of HO-NPhth, Ph$_3$P and diisopropyl azodicarboxylate [Grochowski et al., *J. Carbohydr. Res.*, 50:C15 (1976)] resulted in the formation of the $\beta$-glycoside Compound 9, presumably via intermediate Compound 8 (53 percent overall yield). Although the mechanism of this glycosidation is not fully understood, an $S_N2$ process may be occurring since the $\alpha/\beta$ ratio of the resulting glycoside Compound 9 is dependent upon the ratio of starting lactol anomers. [For a similar observation including glycosyl ester formation, see Smith et al., *Tetrahedron Lett.*, 27:5813 (1986).]

Liberation (using NH$_2$NH$_2$) of the amino group led to hydroxylamine derivative Compound 10, which was condensed with ketone A under acidic conditions to afford Compound 11 (92 percent overall yield from Compound 9; a single geometrical isomer being obtained whose stereochemistry has not been determined).

Silylation (—Si$^t$BuMe$_2$, 99 percent) of Compound 11 gave Compound 12, which on exposure to DIBAL led to the hydroxy Compound 13 (91 percent). Reaction of Compound 13 with thiocarbonyldiimidazole for 20 hours at 25° C. gave a mixture of the thioimidazolide Compounds 14 and 15, the latter resulting from a stereospecific [3,3]-sigmatropic rearrangement of Compound 14. [For a rearrangement of an allylic xanthate in (a) a carbohydrate derivative see: Ferrier et al., *Chem. Commun.*, 1385 (1970); (b) a 2-substituted cyclohexene derivative see: Trost et al., *J. Am. Chem. Soc.*, 194:886 (1982).]

Heating the reaction mixture at reflux for one hour in toluene completed the rearrangement to Compound 15 in 85 percent overall yield from Compound 13. Generation of the free thiol group in Compound 15 using NaSMe resulted in the formation of Compound 16, which was immediately reacted with 2,4,6-trimethylbenzoyl chloride under basic conditions to afford the desired thioester Compound 17. Selective desilylation was achieved with a stoichiometric amount of nBu$_4$NF leading to ketone Compound 18 in good yield.

Stereoselective reduction of the carbonyl group of ring B with a bulky reagent (K-Selectride) led to Compound 19 (74 percent overall yield from Compound 17). Desilylation of Compound 19 led to dihydroxy Compound 20 in quantitative yield. Finally, stereoselective reduction of the oxime in Compound 20 was secured with BH$_3$-NH$_3$/pyridinium p-toluene sulfonate (PPTS), furnishing the targeted ABC system Compound 1 in 85 percent yield. The stereochemistry of the stereogenic centers generated in this sequence (C-4, C-1', C-3' and C-4') was evident from NMR data.

The described chemistry provides stereocontrolled solutions to the crucial bond constructions of the calicheamicin $\gamma_1^I$ oligosaccharide fragment and makes available the interesting subfragment Compound 1 for DNA binding studies and other investigations in this area. Furthermore, the reported sequence facilitates the synthesis of the complete oligosaccharide fragment of these antibiotics, as is discussed hereinafter.

B. The CD Disaccharide and E Ring

The results discussed below describe the synthesis of the CD and E ring systems of calicheamicin $\gamma_1^I$, as Compounds 21 and 22 (FIG. 5; for CD) and 23 and 24 (FIG. 5; for E) in their naturally occurring forms.

Scheme 3 (FIG. 6) outlines the stereoselective construction of the CD systems Compounds 21 and 22 from the readily available fragments Compounds 25 and 29 [Nicolaou et al., *Angew. Chem. Inst. Ed. Engl.*, 27:1097 (1988)]. Thus, Compound 25 was selectively methylated at the 3-hydroxyl group with nBu$_2$SnO-CsF-MeI [Nogashima et al., *Chem. Lett.*, 141 (1987)] to afford Compound 26 (65 percent yield, plus 30 percent recovered starting material).

Acetylation of Compound 26 afforded Compound 27 (95 percent yield), a derivative designed to undergo selective $\beta$-glycosidation due to neighboring group participation, as desired in the present synthetic sequence. Fluoride Compound 28 was generated from Compound 27 upon exposure to N-bromosuccinimide (NBS) and diethylaminosulfur trifluoride (DAST)

[Nicoloau et al., *J. Am. Chem. Soc.*, 106:4159 (1984)] (85 percent yield). Coupling of Compound 28 with Compound 29 under the influence of AgClO$_4$-SnCl$_2$ [Nicolaou et al., *J. Am. Chem. Soc.*, 106:4159 (1984); Mukaiyama et al., *Chem. Lett.*, 431 (1981)] proceeded smoothly to afford, stereospecifically, glycoside Compound 30 in 80 percent yield. Deacetylation of Compound 30 under standard conditions furnished the requisite CD system as the dihydroxy methyl ester Compound 21 in quantitative yield.

Bis(silylation) of Compound 21 (92 percent) followed by DIBAL reduction (90 percent) gave alcohol Compound 32 via derivative Compound 31. Finally, ruthenium chloride/sodium periodate oxidation of Compound 32 at −20 degrees C. afforded carboxylic acid Compound 33 (75 percent), which was successfully coupled to thiophenol under the influence of phenyl dichlorophosphate [PhOP(O)Cl$_2$] [Liu et al., *Con. J. Chem.*, 58:2695 (1980)] to furnish the phenylthio ester Compound 34 in 90 percent yield. Finally, desilylation of Compound 34 gave the targeted CD ring system Compound 22 (90 percent yield).

The synthesis of the two isomers of the carbohydrate unit E, Compounds 23(1R) and 24(1S), proceeded from serine methylester hydrochloride, Compound 35, as shown in Scheme 4 of FIG. 7. Thus, Compound 35 was heated in acetonitrile at reflux with carbonyldiimidazole in the presence of 4-dimethylaminopyridine (DMAP) to give the oxazolidinone Compound 36 in 95 percent yield. N-alkylation of Compound 36 with excess ethyl iodide under basic conditions gave Compound 37 (75 percent yield) which was reduced with DIBAL to the aldehyde Compound 38 in good yield. It is to be understood that other $C_1$-$C_6$ alkyl analogs of Compound 37 are contemplated and can be similarly or prepared using the respective $C_1$-$C_6$ alkyl iodide or $C_1$-$C_6$ alkyl triflate in place of ethyl iodide. For example, use of iso-propyl iodide in place of ethyl iodide provides the N-iso-propyl analog of Compounds 23 and 24 as is present in the E ring of esperamicin.

Stereoselective addition of an allyl group to the aldehyde function of Compound 38 was achieved via the action of (−)-β-methoxydiisopinocampheylborane and allyl magnesium bromide leading to Compound 39 (43 percent overall from Compound 37). Methylation of Compound 39 (Ag$_2$O-MeI, 92 percent yield) followed by ozonolysis (91 percent yield) led to methoxy aldehyde Compound 41 via Compound 40.

Acetylization of Compound 41 proceeded smoothly in MeOH under acid catalysis leading to Compound 42 (85 percent yield). Compound 42 was then exposed to basic conditions to produce the amino alcohol Compound 43 in 96 percent yield. Finally, cyclization of Compound 43 methanol with anhydrous hydrogen chloride furnished a mixture of the methoxy isomers Compounds 23(1R) and 24(1S) which were separated by recrystallization from ethyl acetate to give pure Compounds 23 and 24.

The above-described chemistry demonstrates efficient technology for the construction of the crucial bonds α (glycosidic) and β (thioester) linking carbohydrate units D and B to the aromatic moiety ring C of the calicheamicin $γ_1^I$ oligosaccharide shown in FIG. 1. Furthermore, the reported sequences render readily available derivatives of the CD and E ring systems of the calicheamicins for DNA binding studies and further synthetic bioorganic investigations.

C. Total Synthesis of the Calicheamicin $γ_1^I$ Oligosaccharide

The results discussed below utilize the chemistry, compounds, derivatives and analogs thereof discussed previously for the preparation of the oligosaccharide portion of calicheamicin $γ_1^I$, Compound 100 (FIG. 9). Scheme 5 (FIG. 8) summarizes the construction of key intermediate Compound 54 from building blocks Compounds 44, 45a and 10 utilizing glycosidations [Nicolaou et al, *Angew. Chem. Int. Ed. Engl.*, 27:1097 (1988)] and the Mitsunobu process [Mitsunobu, O., *Synthesis*, 1 (1981)] as well as the before-discussed oxime-forming reaction for assembling the requisite fragments.

Thus, conversion of the methylglycoside Compound 45 to fluoride Compound 45b followed by coupling with Compound 44 led to disaccharide 46 in 51 percent yield together with its anomer (12 percent). Chromatographic separation followed by selective deprotection of Compound 46 led to Compound 47, which was selectively oxidized with nBu$_2$SnO-Br$_2$ [David et al., *J. Am. Chem. Soc. Perkin Trans. I*, 1568 (1979)] at C-4 furnishing ketone Compound 48.

Compound 48 was then coupled with the previously prepared hydroxylamine derivative Compound 10 via oxime formation giving trisaccharide Compound 49 (83 percent yield). [While a single geometrical isomer about the oxime bond was obtained in this reaction its stereochemistry was not assigned. This compound and all other FMOC derivatives described in this work exhibited double signals in the NMR spectra due to rotomers arising from restricted rotation around the C-N bond. Heating the NMR sample at 60 degrees C. (C$_6$D$_6$) often sharpens the spectra to single peaks.]

Elaboration of Compound 49 as described for Compound 11 led, via Compounds 49–51, to the key thionomidazolide Compound 52 in high overall yield (79 percent). Thermolysis of Compound 52 proceeded smoothly to afford the thioester Compound 53 (98 percent yield) via the expected 3,3-sigmatropic rearrangement of Scheme 1 (FIG. 3). Finally, NaSMe-induced cleavage of the CO-S bond of Compound 53 gave the requisite thiol Compound 54 in high yield.

Scheme 6 of FIG. 9 presents the final stages of the synthesis of the calicheamicin oligosaccharide Compound 100. Coupling of acid chloride Compound 55 prepared from Compound 33 with thiol Compound 54 in the presence of DMAP yielded product Compound 56 (88 percent based on thiol). Controlled desilylation of Compound 56 afforded selectively ketone Compound 57 which was reduced with K-Selectride, as previously discussed for Compound 19, to afford hydroxy Compound 58 in 75 percent overall yield from Compound 56.

Complete desilylation of Compound 58 gave tetraol Compound 59 which underwent stereoselective reduction at the oxime site with BH$_3$-NH$_3$/pyridinium p-toluene sulfonate (PPTS), furnishing Compound 60. Finally, removal of the FMOC group from Compound 60 gave the targeted calicheamicin $γ_1^I$ oligosaccharide Compound 100 having a methoxy rather than a calicheamicinone group at the anomeric carbon atom. The structure and stereochemical assignments of Compound 100 were based on its NMR data and of those of its hexacetate derivative Compound 61.

Preparation of the esperamicin trisaccharide generally followed the steps outlined in Schemes 5–7 (FIGS. 8–10) for the calicheamicin $γ_1^I$ ABE ring system. The O-methyl glycoside of the N-isopropylamine-containing ring of esperamicin, Compound 245, corresponding to the calicheamicin $\gamma^{1I}$ E ring, was prepared in a manner similar to that used to prepare Compound 45, but by replacing acetaldehyde of Scheme 4 with acetone. The 1-fluoro derivative, Compound 245b was prepared from O-methyl glycoside Compound 245 following the procedures used to prepare Compound 45b.

Condensation of Compounds 245b and 62 (1.35 equivalents of 245b, 1.0 equivalents of 62, 2.5 equivalents of $AgClO_4$, 2.5 equivalents of $SnCl_2$, 4 Å molecular sieves in THF at $-78° \rightarrow -20°$ C. over seven hours) led to Compound 246 (corresponding to Compound 46). The ratio of $\alpha$ to $\beta$ anomers was about 3:1. Removal of the carbonate group [0.04 equivalents of NaH, in THF-ethylene glycol (20:1) at 25° C. for 0.5 hours] provided the disaccharide, Compound 247, in a 60 percent overall yield. Oxidation of Compound 247, (1.0 equivalent of $^nBu_2SnO$, MeOH at reflux for 1.2 hours, followed by 1.0 equivalent of $^nBu_2SnOMe$, 1 equivalent of $Br_2$ in $CH_2Cl_2$ at 25° C.) provided keto Compound 248 (corresponding to Compound 48) in 76 percent yield.

Reaction of Compounds 10 and 248 (0.1 equivalent PPTS, 1.5 equivalents of 10 in benzene at 25° C. for three hours) gave the oxime, Compound 249 (corresponding to 49) in 70 percent yield. Protection of the free hydroxyl group resulted in Compound 259 in 100 percent yield (1.2 equivalents EtSiOTf, 1.5 equivalents of 2,6-lutidine in $CH_2Cl_2$ at zero→25° C. for 0.5 hours).

The m-chlorobenzoyl group was removed by reaction of Compound 250 with 3.0 equivalents if DIBAL in $CH_2Cl_2$ at $-78°$ C. for 0.5 hours to provide Compound 251 in 95 percent yield (corresponding to Compound 51). Reaction of Compound 251 with 3.0 equivalents of 1,1'-thiocarbonyldiimidazole in acetonitrile at 25° C. for 1.5 hours provided Compound 252, corresponding to Compound 52, in 86 percent yield.

Heating of Compound 252 in toluene at 100° C. for one hour provided the rearranged compound, Compound 253, corresponding to Compound 53, in 100 percent yield. Treatment of Compound 253 with 1.0 equivalent of NaSMe, and 40 equivalents of EtSH in $CH_2Cl_2$ at 25° C. for 1.5 hours provided Compound 254 in 95 percent yield, corresponding to Compound 54. Compound 254 was then methylated (50 equivalents of MeI and 2.5 equivalents of $^iPr_2EtN$ in $CH_2Cl_2$ at 25° C. for one hour) to provide Compound 256 in 90 percent yield.

Scheme 12 of FIG. 15 illustrates the remaining steps of this synthesis. Thus, the TBS group was removed from Compound 256 by reaction with 5.0 equivalents of acetic acid and one equivalent of $^nBu_4NF$ in THF at $-40°$→zero degrees C. to form the corresponding ketone, Compound 257, in step a. Ketone Compound 257 was then stereoselectively reduced in step b with 3.0 equivalents of K-Selectride® in DME-THF (7:1) at $-78°$ C. for 0.7 hours to provide Compound 258 in a two step yield of 67 percent. Compound 258 was converted to Compound 259 in 85 percent yield in step c by treatment with an excess of HF-pyridine in $CH_2Cl_2$-THF (7:1) at $-20°$→zero degrees C. for three hours.

The oxime linkage of Compound 259 was reduced in step d by reaction with 13 equivalents each of $NaBH_3CN$ and $BF_3.OEt_2$ in $CH_2Cl_2$-THF-$Et_2O$ (2:1:1) as solvent at $-60°$→$-40°$ C. for two hours to provide Compound 260 in 90 percent yield, with a ratio of C-4 epimers of about 2:1 in favor of the $\alpha$-anomer. The FMOC group was removed by reaction of Compound 260 in THF-$Et_2NH$ (1:1) at 25° C. for two hours to provide Compound 400 in 81 percent yield as step e.

D. The Esperamicin $A_1$ Small Saccharide Analog

The smaller of the two esperamicin $A_1$ saccharides was prepared following the reactions illustrated in Scheme 14 of FIG. 17.

Thus, methyl-$\alpha$-L-fucopyranoside Compound 320 [Zehavi et al., *J. Org. Chem.*, 37:2141 (1972)] was regioselectively converted into intermediate Compound 321 by sequential reaction with carbonyldiimidazole (2.5 equivalents of 1,1'-carbonyldiimidazole in acetonitrile at reflux for two hours; 76 percent yield) and thiocarbonyldiimidazole (1.3 equivalents of 1,1'-thiocarbonyldiimidazole in acetonitrile at 25° C. for two hours; 80 percent yield), steps a and b.

Compound 321 was deoxygenated [2.0 equivalents of $^nBu_3SnH$, AIBN catalytic amount) in toluene-DMF (1:1) at 110° C. for one hour; 80 percent yield), step c. The resulting compound was treated with 5.0 equivalents of $PhSSiMe_3$, 3.0 equivalents of $ZnI_2$ and 1.2 equivalents of $^nBu_4NI$ in 1,2-dichloroethane for 2.5 hours at 70° C., step d, and then with 0.05 equivalents of NaH in THF-ethylene glycol (20:1) at 25° C. for two hours, step e) to form Compound 322, in 63 percent yield for the last two steps.

The second ring compound required for this saccharide, Compound 324, was prepared from 4,5-dimethoxyanthranilic acid (Compound 323). Thus, Compound 323 was first reacted with 1.1 equivalents of phthaloyl chloride and 2 equivalents of $Et_3N$ in THF at 25° C. for two hours to form the phthalimido derivative (Phth) in 50 percent yield, step g. That compound was then reacted with 1.2 equivalents of oxalyl chloride in $CH_2Cl_2$-DMF (100:1) at 25° C. for 0.5 hours to provide Compound 324 step h, in about 50 percent yield overall.

Compound 322 was reacted with 1.2 equivalents of $^nBu_2SnO$ in methanol at 65° C. for 1.5 hours to form the cyclic tin dialkoxide, step f. The methanol was then exchanged for THF as solvent. The cyclic tin dialkoxide was then reacted with 1.5 equivalents of Compound 324 and 2 equivalents of $Et_3N$ in THF at 25° C. for 0.75 hours in step i to provide a 65 percent yield of the hydroxyl-containing precursor to Compound 325. Treatment of that precursor with 1.2 equivalents of $Et_3SiOTf$ and 1.5 equivalents of 2,6-lutidine in $CH_2Cl_2$ at zero degrees C. for 0.2 hours provided a 100 percent yield of Compound 325 in step j.

The phthaloyl group was removed from Compound 325 by reaction with 2.0 equivalents of hydrazine and 1.0 equivalent of acetic acid in methanol-$CH_2Cl_2$(5:1) at 25° C. for five hours to provide Compound 326 in 83 percent yield, in step k. Reaction of Compound 326 with 3.0 equivalents of Compound 327 [Wenkert et al., *J. Am. Chem. Soc.*, 105:2021 (1983)] and 5.0 equivalents of $Et_3N$ in THF at 25° C. provided the desired saccharide analog Compound 328 in 85 percent yield in step l.

E. Chimeric Biologically Active Agents

The before-discussed syntheses of intermediates and the calicheamicin oligosaccharide Compound 100 illustrate preparation of materials that can be utilized to prepare chimeric biologically active agents. Examples of such biological activities include antimicrobial, anticancer and DNA cleaving activities.

Exemplary preparation of three useful oligosaccharides for such chimers are illustrated in Schemes 7 and 8 shown in FIGS. 10 and 11, respectively. Scheme 7 of FIG. 10 illustrates the preparation of a disaccharide analog to the A and E ring disaccharide intermediate Compound 148 and also a trisaccharide analog of the ABE trisaccharide ring system of calicheamicin. This trisaccharide, Compound 154, can be reacted with an aromatic acid as illustrated in Scheme 5 to form a 4-ring analog of the calicheamicin oligosaccharide. Compound 154 also contains a photolabile blocking group, an o-nitrobenzyloxy group (ONBn), at the anomeric carbon atom of the A ring for linkage to an aglycone molecule.

Turning now more specifically to Scheme 7, Compounds 62 and 45b are reacted as illustrated in Scheme 5, step (c) to form Compound 146 and then Compound 147 by step (d). Compound 147 is reacted as in step (e) of Scheme 5 to form Compound 148. Compound 148 is reacted with Compound 10 as in step (f) of Scheme 5 to form Compound 149. That compound is then transformed to Compounds 150, 151 and 152 following steps (g), (h) and (j) of Scheme 5. Compound 152 is thereafter rearranged to Compound 153 following the procedures of step (i) of Scheme 5, and is thereafter transformed into mercaptan Compound 154 using the conditions of step (k) of Scheme 5.

Reaction of Compound 154 with the acid chloride prepared from Compound 33 forms a 5-ring oligosaccharide, whereas reaction with benzoyl chloride or 2,4,6-trimethylbenzoyl chloride produces a 4-ring oligosaccharide. Reduction of the oxime double bond with $NH_3$-$BH_3$ and PPTS in methylene chloride as shown in step (e) of Scheme 6 provides the substituted hydroxylamine.

An exemplary 5-ring oligosaccharide such as Compound 200 is illustrated in Scheme 8 of FIG. 11. Compound 200 is similar to Compound 60, except for the presence of the photo-labile ONBn group as $R^2$ and the presence of triethylsilyl ($SiEt_3$) groups, $R^1$, on the saccharide hydroxyl groups.

As is seen from the reaction in Scheme 8, Compound 200 is irradiated (hv) to remove the ONBn group and replace it with a 1-position hydroxyl group to form Compound 201. The 1-position hydroxyl is thereafter reacted with DAST as described in the preparation of Compound 45a to prepare the 1-fluoro derivative, Compound 202.

The fluoro derivative, Compound 202, is thereafter reacted with an aglycone, HZ, such as those depicted in FIG. 11 to form the complete chimeric antibiotic. Thus, Compound 202 is reacted with an aglycone, HZ, in the presence of silver perchlorate ($AgClO_4$) and stannus chloride ($SnCl_2$) to form the blocked chimer Compound 203.

The blocked chimer is thereafter deblocked as with morpholine in THF to remove the FMOC group and form the free ethylamino chimer, Compound 204. The trialkylsilyl groups are thereafter removed with TBAF to form the completely deblocked chimeric antibiotic, Compound 205.

The in vitro DNA cleaving ability of the enediyne, $HZ_1$, is reported in Nicolaou et al., *J. Am. Chem. Soc.*, 110:7247 (1988). The DNA cleaving properties of compounds such as $HZ_2$ are discussed in Nicolaou et al., *Angew. Chem. Int. Ed. Engl.*, 28:1272 (1989). The dynemicin A analog, Compound 300, reported by Nicolaou et al., *J. Am. Chem. Soc.*, 112:7416 (1990) can also be used. Additional enediyne analogs of dynemicin A such as Compounds 450 and 458 are discussed in Nicolaou et al., *Science*, 256:1172 (1992) and in the citations therein. Compounds 450 and 458 were repeated to exhibit $IC_{50}$ values against Molt-4 leukemia cells of about $10^{-6}$ and $10^{-14}$M, respectively, whereas Compound 300 was separately found to exhibit an $IC_{50}$ value if about $10^{-5}$M. The enediyne-diketo-diol, reported in Mantlo et al., *J. Org. Chem.*, 54:2781 (1989) as those authors' Compound 4, also is reported to cleave DNA in vitro and is useful herein. The golfomycin group of DNA-cleaving compounds disclosed in allowed U.S. patent application Ser. No. 07/561,964, filed May 7, 1990, now U.S. Pat. No. 5,136,089, can also be used. The aglycone portions of daunrobicin and doxorubicin are likewise useful, as is morpholinodoxorubicin.

Structures of exemplary reacted aglycone, Z, groups, disclosed in the text and figures herein are illustrated below.

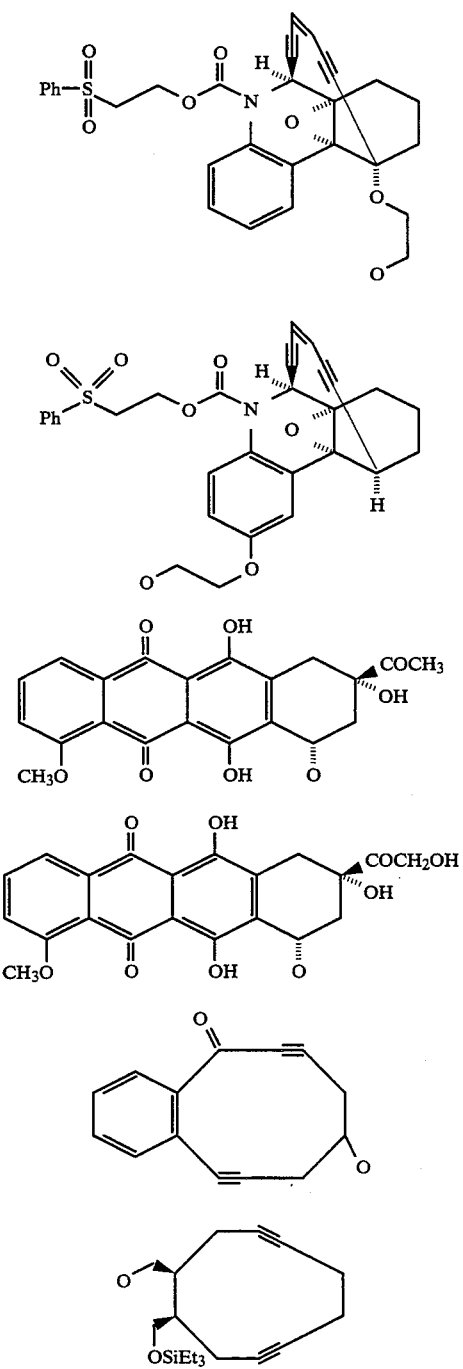

-continued

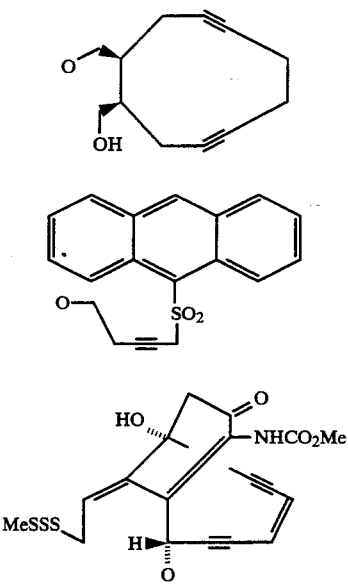

The synthesis of yet another biologically active chimer is illustrated in Scheme 9 shown in FIG. 12, in which Compounds 211–220 and 222 are analogs of Compounds 11–20 and 22, respectively, and Compound 221 is an analog of Compound 1. This chimer utilizes an oligosaccharide portion containing three rings that are analogous to the A, B and C rings of calicheamicin.

Here, Compound 10 and Compound 63 (an analog of Compounds A and 148) are reacted in step (a) in the presence of PPTS (pyridinium p-toluenesulfonate) to form Compound 211. Blocking the free hydroxyl with $^t$BuMe$_2$SiOTF forms Compound 212. Treatment of Compound 212 with DIBAL removes the aromatic ester, as was the case in step (j) of Scheme 2, to form Compound 213.

Compound 213 is reacted with thiocarbonyl diimidazole to form the thioimidazyl ester Compound 214, which is rearranged by heating in toluene at 110 degrees C. to form thioester Compound 215. Treatment of Compound 215 with NaSMe removes that ester group to form mercaptan Compound 216, which is quickly reacted with an aromatic carboxylic acid chloride such as 2,4,6-trimethylbenzoyl chloride to form aromatic ester Compound 217.

Compound 217 is then treated with one equivalent of TBAF to remove the enol ether blocking group and form ketone Compound 218, analogously to step (o) of Scheme 2. Again, following the precedents of Scheme 2, the keto group of Compound 218 is reduced with K-Selectride to form the corresponding hydroxyl group of Compound 219, and the remaining hydroxyl blocking trialkylsilyl groups are removed to form Compound 220.

The substituted oxime group of Compound 220 is reduced with NH$_3$-BH$_3$/PPTS, as discussed previously, to form the 0-N-disubstituted hydroxylamine Compound 221, an analog of Compound 1. The hydrogens of hydroxyl groups of Compound 221 are then replaced with SiEt$_3$ groups to form Compound 222.

Compound 222 is thereafter irradiated to remove the glycosyl ONBn group at the anomeric carbon atom to form Compound 223. That compound is then reacted with DAST to form the 1-fluoro derivative, Compound 224.

Compound 224 is then reacted with a DNA cleaving aglycone, HZ, as discussed previously to form the hydroxy-blocked chimer Compound 225. Removal of the tri-alkylsilyl groups with TBAF forms the biologically active agent, Compound 226.

Scheme 10 of FIG. 13 illustrates the synthesis of an A and E ring disaccharide derivative, Compound 167. Thus, starting with Compound 148, oxime formation with O-benzyl hydroxylamine under acid conditions led to Compound 160 (step a, 90 percent, single geometrical isomer of unassigned stereochemistry), which was silylated under standard conditions to furnish Compound 161 (step b, 90 percent). Photolytic cleavage [Zenhavi et al., *J. Org. Chem.*, 37:2281 (1972); Zenhavi et al., ibid 37:2285 (1972); Ohtsuka et al., *J. Am. Chem. Soc.*, 100:8210 (1978); Pillai, *Synthesis*, 1 (1980)] of the o-nitrobenzyl group from Compound 161 (THF-H$_2$O, 15 minutes, step c) produced lactol Compound 162 in 95 percent yield. Treatment of Compound 162 with NaH-Cl$_3$CC≡N [Grandler et al., Carbohydr. Res., 135:203 (1985); Schmidt, *Angew Chem. Int. Ed., Engl.*, 25:212 (1986)] in CH$_2$Cl$_2$ for two hours at 25° C. (step d) resulted in the formation of the α-trichloroacetimidate Compound 163 in 98 percent yield.

Reaction of benzyl alcohol (2.0 equivalents) with trichloroacetimidate Compound 163 under the Schmidt conditions [Grandler et al., *Carbohydr. Res.*, 135:203 (1985); Schmidt, *Angew Chem. Int. Ed., Engl.*, 25:212 (1986) (BF$_3$.Et$_2$O, CH$_2$Cl$_2$, −60→−30° C., step e)] resulted in stereoselective formation of the β-glycoside Compound 164 (79 percent yield) together with its anomer (16 percent, separated chromatographically [$^1$H NMR, 500 MHz, C$_6$D$_6$, Compound 164: J$_{1,2}$=6.5 Hz, epi-Compound 164; J$_{1,2}$=2.4 Hz]. On the other hand, treatment of lactol Compound 162, with DAST led to the glycosyl fluoride Compound 163a in 90 percent yield (about 1:1 anomeric mixture, step d). Reaction of Compound 163a with benzyl alcohol in the presence of silver silicate-SnCl$_2$ [Paulsen et al., *Chem. Ber.*, 114:3102 (1981)] resulted in the formation of the β-glycoside Compound 164 and its anomer in 85 percent (about 1:1 anomeric mixture). Generation of intermediate Compound 166 via Compound 165 proceeded smoothly under standard deprotection conditions, steps f and g. Finally, exposure of Compound 166 to Ph$_2$SiH$_2$ in the presence of Ti(O$^i$Pr)$_4$ resulted in the formation of the desired Compound 167 as the only detectable product (92 percent yield, step h). Interestingly, reduction of Compound 166 with NaCNBH$_3$-H led predominantly to the 4-epimer of Compound 167 (90 percent yield). The stereochemical assignments of Compound 167 and epi-167 at C-4 were based on $^1$H NMR coupling constants [$^1$H NMR, 500 MHz, C$_6$D$_6$, Compound 167: J$_{3,4}$=9.5, J$_{4,5}$=9.5 Hz; epi-Compound 167:J$_{3,4}$=1.9 Hz, J$_{4,5}$=1.5 Hz ].

As an application of this technology, the calicheamicin-dynemicin A analog hybrid Compounds 307a and 307b (Scheme 11 of FIG. 14) were targeted starting with the recently reported model Compound 300 [Nicolaou et al., *J. Am. Chem. Soc.*, 112:7416 (1990); for another approach to a dynemicin A model, see: Porco, Jr., et al., ibid 112:7410 (1990)]. Thus, coupling of Compound 300 with ethyl bromoacetate under basic conditions led to Compound 301 (60 percent yield, step a) which was converted to primary alcohol Compound 303 (80 percent overall yield) by: (i) ester hydrolysis; (ii)

2-pyridyl thiolester formation (step b), and (iii) reduction (step c). Coupling of Compound 303 (1.2 equivalent) with trichloroacetimidate Compound 163 in step d under the influence of $BF_3.Et_2O$ led to the formation of two major products (70 percent, about 1:1 ratio) and two minor products (14 percent, about 1:1 ratio) which were chromatographically separated.

The major isomers were proven to be the diastereomeric β-glycosides Compound 304a ($R_f$=0.12, silica, 20 percent ethyl acetate in petroleum ether) and Compound 304b ($R_f$=0.10, silica, 20 percent ethyl acetate in petroleum ether) [$^1$H NMR, 500 MHz, $C_6D_6$, Compound 304a: $J_{1,2}$=6.5 Hz; Compound 304b: $J_{1,2}$=6.5 Hz] whereas the minor isomers were shown to be the anomers of Compounds 304a and 304b at C-1 [$^1$H NMR, 500 MHz, $C_6D_6$, epi-Compound 304a, $J_{1,2}$=2.4 Hz: epi-Compound 304b, $J_{1,2}$=2.4 Hz]. Sequential deprotection of Compounds 304a and 304b as described above for Compound 164 led to oximes Compounds 306a and 306b via intermediate Compounds 305a and 305b, respectively, steps e and f.

Finally, reduction of Compounds 306a and 306b under the $Ph_2SiH_2$-$Ti(O^iPr)_4$ conditions (step g) led exclusively to the targeted Compounds 307a and 307b, respectively, (90 percent yield). The C-4 stereochemistry of Compounds 307a and 307b was again based on the coupling constants $J_{4,3}$=9.5 and $J_{4,5}$−9.5 Hz for the newly installed H-4. Structures of Compounds 304a–307a and 304b–307b are interchangeable, since the absolute stereochemistry of the aglycones has not been determined.

It is to be understood that a useful chimer can be made using an aglycone (HZ) shown in FIGS. 11 and 12 and the disaccharide (Compound 163) shown in FIG. 13. Conversely, a dynemicin A analog such as Compounds 300, 450 or 458 can be used in place of one of the HZ molecules of FIGS. 11 and 12 in the preparation of a chimer as shown in those figures, as can one of the other DNA-cleaving compounds discussed herein.

An exemplary synthesis of calicheamicin $\gamma_1^I$ that further illustrates the preparation of chimeric compounds is outlined in Scheme 13 of FIG. 16.

Here, Compound 401, the trichloroacetimidate, was prepared via the corresponding o-nitrobenzyl glycoside, Compound 451, that itself was prepared following the general syntheses described herein for Compounds 58 and 163. Compound 402 was prepared as described in Smith et al., *J. Am. Chem. Soc.*, 114: (1992). Compound 403 was prepared in 70 percent yield by selective benzoylation of Compound 402 (1.2 equivalents of benzoyl chloride-pyridine in $CH_2Cl_2$ at zero degrees C for one hour) in step a.

Compounds 401 (1.4 equivalents) and 403 (1.0 equivalent) were admixed with 1.4 equivlents of $BF_3.OEt_2$ in $CH_2Cl_2$ at −50° C. and reacted for one hour to provide Compound 404 in 70 percent yield; step b. Reaction of Compound 404 with 3 equivalents of DIBAL in $CH_2Cl_2$ at −90° C. for one hour provided Compound 405 in 92 percent yield as step c. Reaction of Compound 405 with 10 equivalents $PPh_3$, 8 equivalents of DEAD, and 8 equivalents of thioacetic acid at zero degrees C for 0.5 hours in step d provided Compound 406 in 92 percent yield. Reaction of Compound 406 with 10 equivalents of HF-pyridine in THF-$CH_2Cl_2$ (5:1) at zero degrees C for four hours provides Compound 407 as step e.

Reaction of Compound 407 with 10 equivalents of $NaCNBH_3$ and 2 equivalents of $BF_3$-$OEt_2$ in THF for 0.5 hours provides the reduced disubstituted hydroxylamine Compound 408 as a mixture of isomers in step f, with the desired α-epimer at the C-4 position of the A ring predominating. Reaction of Compound 408 with 10 equivalents of piperidine in THF at zero degrees C for 0.5 hours removes the FMOC group and provides Compound 409 as step g.

Reaction of Compound 409 with 10 equivalents of DIBAL in $CH_2Cl_2$ at −90° C. for 0.5 hours provides Compound 410 as step h. Compound 410 is then reacted with 5 equivalents of N-(methyldithio)phthalimide in $CH_2Cl_2$ at zero degrees C. for 16 hours in step j, and the ketal is deprotected to provide calicheamicin $\gamma_1^I$.

Still further chimeras have been prepared that contain a fused-ring enediyne glycosidically-linked to the complete calicheamicin oligosaccharide or an analog thereof. Exemplary synthetic steps are outlined in Schemes 15 and 16 of FIGS. 18 and 19, respectively.

Thus, a compound such as Compound 303 of Scheme 11 (FIG. 14-A) was reacted with phenylthioethanol in the presence of a base to exchange out the phenoxide moiety from the corresponding carbamate. The resulting compound was then oxidized with m-chloroperbenzoic acid to form the corresponding 2-(phenylsulfonyl)ethyl carbamate, Compound 450.

Compound 450 was reacted with Compound 401 shown in Scheme 15 of FIG. 18 to form Compound 453. Compound 401 was prepared from Compound 451 via the hydroxyl derivative Compound 452.

Thus, Compound 451 was irradiated in THF-$H_2O$ (9:1, v/v) at zero degrees C. in step a to provide a 95 percent yield of hydroxyl Compound 452. That compound was reacted with a catalytic amount of NaH and trichloroacetonitrile in methylene chloride (1:12, v/v) at 25° C. to provide a 98 percent yield of Compound 401 in step b. Compounds 450 and 401 were coupled in step c in benzyl alcohol, $BF_3.Et_2O$ in methylene chloride at −60°→−30° C. to provide Compound 453 as a mixture of diastereomeric anomers 453a and 453b present as a β- to α-anomer ratio of about 5:1, the β-anomer being shown as Compound 453a, and the α-anomer, Compound 453b, not being shown.

Reaction of Compounds 453a and 453b with ($^nBu)_4NF$ using standard conditions removed the triethylsilyl groups. The oxime- and FMOC-containing, hydroxyl deblocked compound that resulted, Compounds 454a and 454b, thus contained the oligosaccharide portion discussed previously for a chimer of Formula IX in which $R^8$ is FMOC and $R^9$ is ethyl. Subsequent reaction with diethylamine under usual conditions removed the FMOC group to form Compounds 455a and 455b to form a chimer of Formula IX in which $R^8$ is hydrogen and $R^9$ is ethyl.

Scheme 16 of FIG. 19 shows only the oxime-containing ring of Compound 455a, with the remaining portions indicated by the wavy lines. As is shown in Scheme 16, reduction of Compound 455a with sodium cyanoborohydride in $BF_3.Et_2O$ at −50° C. provided a 65 percent yield of epimeric Compounds 456a and 456b, that were present in about equal amounts. Those compounds were epimeric at the 4-position of the A ring as indicated by the number 4 and the arrow, only Compound 456a having the stereochemistry of the calicheamicin $\gamma_1^I$ saccharide is shown.

Chimeric Compounds 457a and 457b (shown below) can be prepared by following the chemistry outlined and discussed in relation to Schemes 15 and 16 by replacing Compound 450 of Scheme 15 with Compound 458 that is discussed in Nicolaou et al., *Science*, 256:1172 (1992), and whose structure is also shown below.
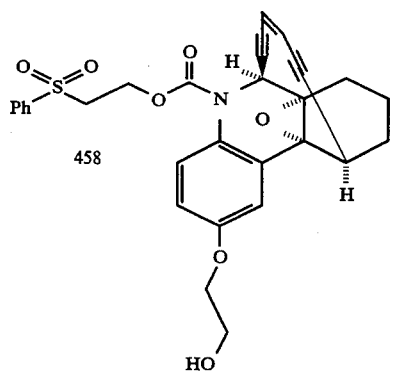
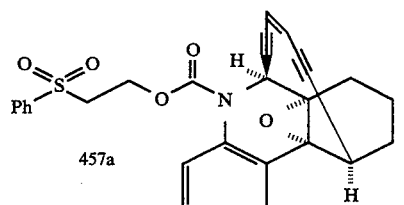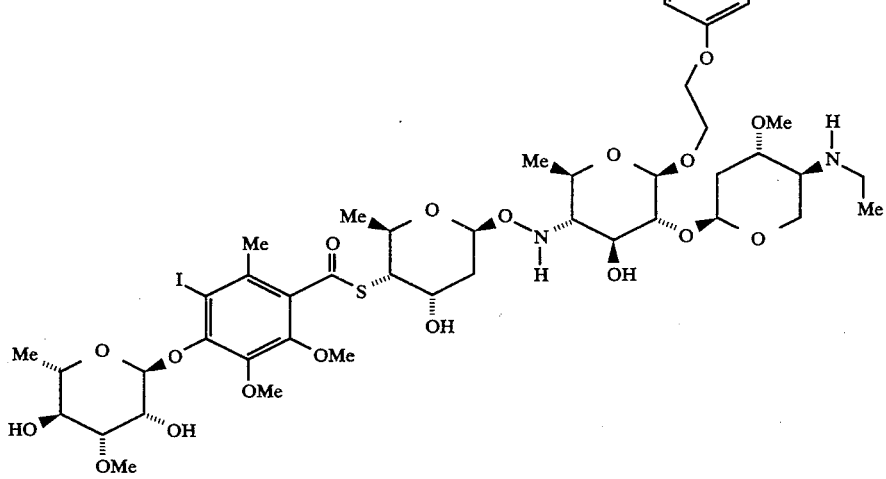

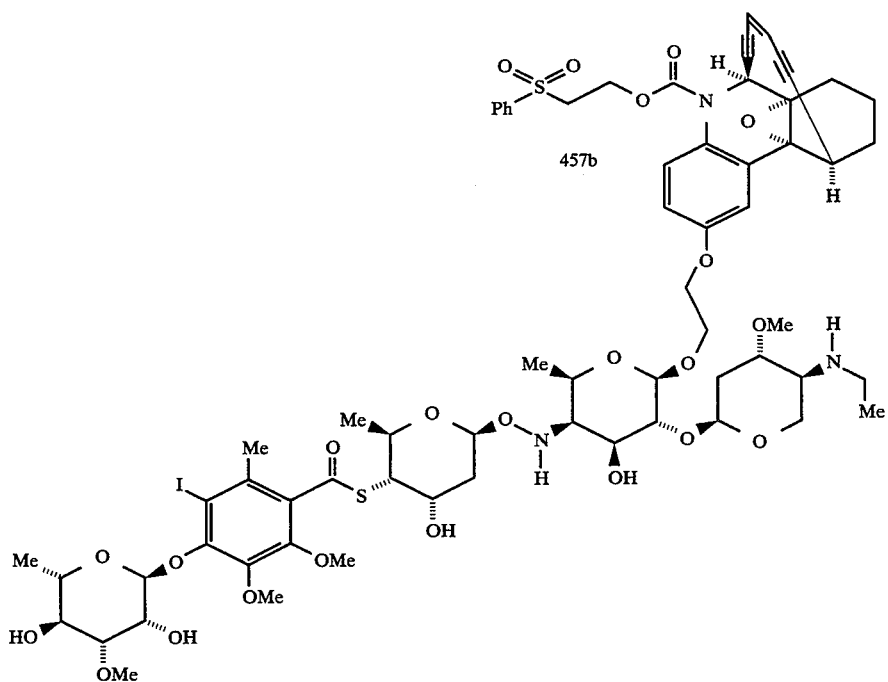

457b

The data in Table 1, hereinafter, illustrate the effects of several chimeric compounds containing oligosaccharides on the killing of cancer cells. Compounds 456a and 456b that contain the calicheamicin $\gamma_1^I$ oligosaccharide portion linked to an enediyne aglycone portion were found to be particularly effective. Compound 456a contained that oligosaccharide in the native configuration, whereas Compound 456b had the epimeric configuration.

Previous studies by the Ellestad [(a) Zein et al., *Science*, 240:1198 (1988); (b) Zein et al., *Science*, 244:697 (1989); (c) Ding et al., *J. Am. Chem. Soc.*, 113:6617 (1991)], Schreiber [Hawley et al., *Proc. Natl. Acad. Sci. U.S.A.*, 86:1105 (1989)]; Kahne [(a) Walker et al., *J. Am. Chem. Soc.*, 112:6428 (1990); and (b) Walker et al., *J. Am. Chem. Soc.*, 113:4716 (1991)]; and Danishefsky [Dark et al., *Proc. Natl. Acad. Soc.*, 88:7464 (1991)] groups suggested selective interactions of the calicheamicin $\gamma_1^I$ oligosaccharide with duplex DNA along specific sequences within the minor groove. In particular, Schreiber et al. [Hawley et al., *Proc. Natl. Acad. Sci. U.S.A.*, 86:1105 (1989)] proposed a binding model for this interaction based on both the stereochemistry of the oligosaccharide bonds and the potential of its iodine group to bind to the DNA's nitrogen atoms.

Footprinting studies the O-methyl glycosides of saccharide Compounds 167a, 100, its C-4 epimer (100a) and a similar compound lacking the iodo group in Ring C, 100b, shown below, were designed to probe these questions. Those studies demonstrated that although the calicheamicin oligosaccharide glycoside binds specifically to DNA, the preferred saccharide binding sites do not coincide precisely with those observed for intact calicheamicin.

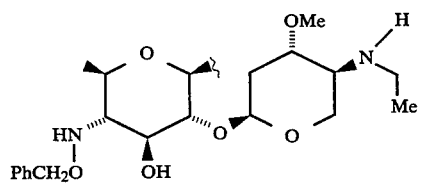

167a

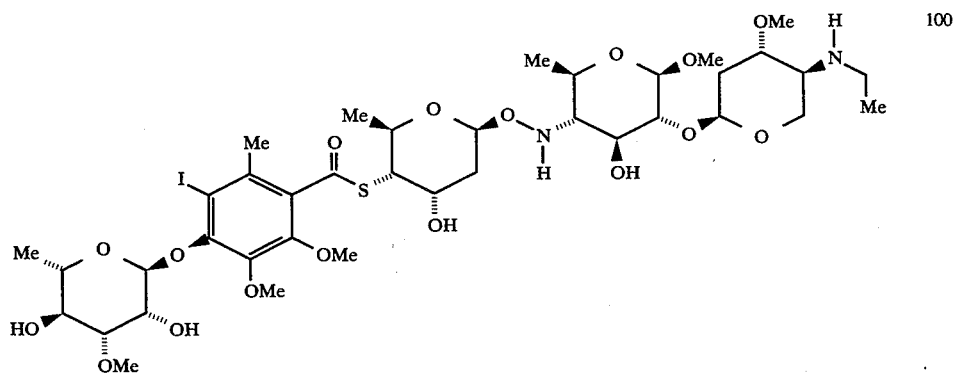

100

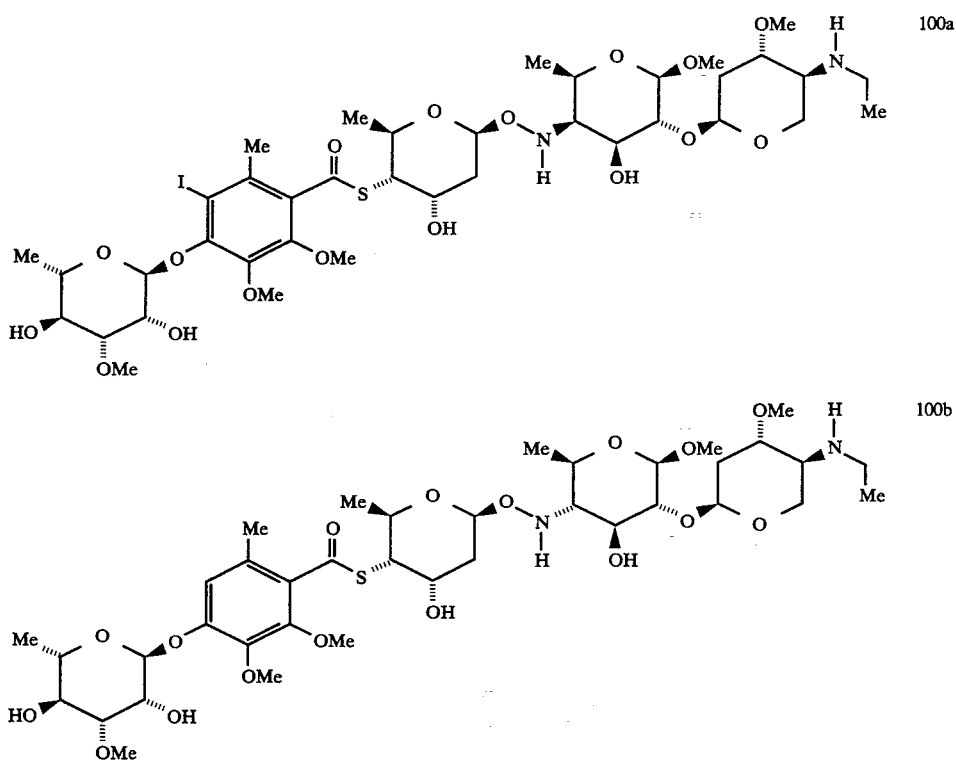

The oligosaccharides 167a, 100, 100a, and 100b were obtained by chemical synthesis following procedures similar to those discussed before. The 93 base-pair Sal I - Sph I double-stranded DNA fragment of pBR322 was obtained enzymatically and was [5'-$^{32}$P]-labeled on one strand. pBR322 DNA was cleaved at the unique Sal I site, dephosphorylated using calf intestine phosphatase, 5'-$^{32}$P]-phosphorylated using T4 polynucleotide kinase and [g-$^{32}$P ATP (4.5 $^m$Ci/pmol), and cleaved again at the unique Sph I site. These precursors generated a 93 base-pair double-stranded fragment, [5'-$^{32}$P]-labeled at the Sal I end, which was purified by gel electrophoresis in a nondenaturing 10 percent polyacrylamide gel and subsequent column chromatography on Sephadex G-25. The oligosaccharides were pre-incubated with the DNA fragment at 37° C. for 30 minutes and DNase I was added to cleave the DNA and generate footprinting patterns by autoradiography.

The autoradiograms showed that the natural oligosaccharide Compound 100 provided concentration-dependent protection, presumably due to binding, in the region of three calicheamicin $\gamma_1^I$ binding sites: CTCT, TCCT and AGGA (reading 5'→3' along the labeled strand). The oligosaccharide 100a with the unnatural stereochemistry at the hydroxylamine nitrogen-bearing C-4 position offered no protection at the same concentrations. A similar lack of protection under the same conditions was observed with the oligosaccharides 100b, in which the iodine atom was replaced by a hydrogen, and 167a.

That the protection pattern did not coincide precisely with the observed calicheamicin cleavage sites prompted the carrying out of replicate footprinting studies over a 48 base-pair segment of the DNA fragment. The degree of protection against DNase I digestion offered by both the natural and unnatural stereoisomers was determined by comparing the amount of radioactivity in adjacent lanes along the electrophoresis gel. The protected regions coincided only roughly with calicheamicin $\gamma_1^I$ recognition sequences [(a) Zein et al., Science, 240:1198 (1988); (b) Zein et al., Science, 244:697 (1989); (c) Ding et al., J. Am. Chem. Soc., 113:6617 (1991)], Schreiber [Hawley et al., Proc. Natl. Acad. Sci. U.S.A., 86:1105 (1989)] and observed calicheamicin $\gamma_1^I$ cleavage sites. The disparity may be due to: (1) imprecise DNA recognition by the carbohydrate moiety alone; (2) impaired access of DNase I at sites adjacent to bound carbohydrate; and (3) distortion of the DNA duplex adjacent to bound carbohydrate which prevents functional recognition by DNase I. Nonetheless, these data demonstrate selective binding of oligosaccharide Compound 100 with specific base sequences of DNA and illustrate as crucial the natural stereochemistry at C-4 for calicheamicin $\gamma_1^I$.

These results show that some, but not all, of the binding specificity of calicheamicin $\gamma_1^I$ resides in its carbohydrate domain. This is consistent with Schreiber's hypothesis concerning the importance of the iodine and carbohydrate stereochemistry to this binding. However, it appears that the enediyne moiety confers added specificity to the calicheamicin/DNA interactions.

Although the above binding studies help to illustrate the binding specificity for calicheamicin $\gamma_1^I$ and to corroborate Schreiber's hypothesis as to the importance of the iodide group and stereochemistry, they do not completely explain the binding specificity of that agent nor do they explain efficacies in cancer cell killing exhibited by Compounds 456a and 456b shown in Table 1, hereinafter. Thus, although some binding specificity can be obtained for chimeras bound to the calicheamicin saccharide $\gamma_1^I$ Compound 100, chimeras that utilize other saccharides are also useful. This type of activity with and without saccharide binding and DNA cleaving specificities is also shown for calicheamicin $\gamma_1^I$ and esperamicin, respectively, whose aglycone portions are substantially the same, but whose saccharide portions differ, and which exhibit double DNA strand cuts at specific sequences (calicheamicin $\gamma_1^I$) and no strong sequence specificity in DNA cleaving (esperamicin). Zein et al., *Science*, 244:697 (1989).

Preparation of other chimeras using other appropriate fused ring enediyne aglycones and oligosaccharide portions can be carried out similarly.

Large Scale Screening Against Cancerous Cell Lines

Several of the before-described chimeric compounds were screened against several or all of a panel of 5–10 cancerous cell lines as target cells and seven "normal" cell preparations. This screening utilized a sulforhodamine B cytotoxicity assay as discussed below.

SULFORHODAMINE B CYTOTOXICITY ASSAY

1. Preparation of target cells in 96-well plates
   a. Drain media from $T_{75}$ flask of target cell line(s) and carefully wash cell monolayer two times with sterile PBS (approximately 5 mL per wash)
   b. Add 5 mL trypsin/EDTA solution and wash monolayer for approximately 15 seconds
   c. Drain all but approximately 1 mL of trypsin/EDTA from flask, cap flask tightly, and incubate at 37° C. for approximately two to five minutes until cells come loose.
   d. Add 10–15 mL tissue culture (T.C.) medium (RPMI 1640 plus 10 percent fetal calf serum and 2 mM L-glutathione) to flask and pipet gently up and down to wash cells.
   e. Remove a ½ mL aliquot of the cell suspension and transfer to a glass 12×75 mm culture tube for counting.
   f. Count cells on a hemacytometer using trypan blue, and determine percent viability.
   g. Adjust volume of cell suspension with T.C. media to give a density of $1 \times 10^5$ cells/mL.
   h. Add 100 μL of T.C. medium to wells A1 and B1 of a 96-well plate for blanks.
   i. Add 100 μL of cell suspension to the remaining wells of the 96-well plates.
   j. Incubate plates for 24 hours at 37° C., 5–10 percent $CO_2$ in a humidified incubator.
2. Preparation of sample drugs and toxic control
   a. Stock drug solutions were prepared by dissolving drug in the appropriate solvent (determined during chemical characterization studies) and sterile filtering the drug-solvent solution through a sterile 0.2 μfilter unit. An aliquot was taken from each filtered drug solution and the O.D. was measured to determine the drug concentration.
   b. Dilute the stock drug solution prepared above with T.C. medium to the desired initial concentration ($10^{-2}$–$10^{-4}$M). A minimum volume of 220 μL of diluted drug is required per 96-well plate used in the assay.
   c. Prepare toxic control by diluting stock doxorubicin solution to $10^{-7}$ to $10^{-9}$M in T.C. medium. A minimum volume of 300 μL is required per 96-well plate.
3. Addition of Sample Drugs, Compounds, Chimeras and Controls to 96-well Plates
   a. Remove and discard 100 μL of T.C. medium from the wells in Column #2 of the 96-well plate using a multi-channel pipettor and sterile tips.
   b. Add 100 μL of the initial compound dilution to adjacent duplicate wells in Columns #2. (Four materials can be tested in duplicate per 96-well plate.)
   c. Remove 10 μL of diluted compound from the wells in Column #2 and transfer to the corresponding wells in Column #3. Mix by pipetting up and down gently approximately five times.
   d. Transfer 10 μL to the appropriate wells in Column #4 and continue to make 1:10 dilutions of compound across the plate through Column #12.
   e. Remove and discard 100 μL of medium from wells F1, G1, and H1. Add 100 μL of toxic control (Doxorubicin diluted in T.C. medium) to each of these wells.
   f. Incubate (37° C., 5–10 percent $CO_2$ in humidified incubator) plates for a total of 72 hours. Check plates at 24 hour intervals microscopically for signs of cytotoxicity.
4. Cell Fixation
   a. Adherent cell lines:
      1. Fix cells by gently layering 25 μL of cold (4° C.) 50 percent trichloroacetic acid (TCA) on top of the growth medium in each well to produce a final TCA concentration of 10 percent.
      2. Incubate plates at 4° C. for one hour.
   b. Suspension cell lines:
      1. Allow cells to settle out of solution.
      2. Fix cells by gently layering 25 μL of cold (4° C.) 80 percent TCA on top of the growth medium in each well.
      3. Allow cultures to sit undisturbed for five minutes.
      4. Place cultures in 4° C. refrigerator for one hour.
   c. Wash all plates five times with tap water.
   d. Air dry plates.
5. Staining Cells
   a. Add 100 μL of 0.4 percent (wt./vol.) Sulforhodamine B (SRB) dissolved in 1 percent acetic acid to each well of 96-well plates using multichannel pipettor.
   b. Incubate plates at room temperature for 30 minutes.
   c. After the 30 minute incubation, shake plates to remove SRB solution.
   d. Wash plates two times with tap water and 1 x with 1 percent acetic acid, shaking out the solution after each wash. Blot plates on clean dry absorbent towels after last wash.
   e. Air dry plates until no standing moisture is visible.
   f. Add 100 μL of 10 mM unbuffered Tris base (ph 10.5) to each well of 96-well plates and incubate for five minutes on an orbital shaker.
   g. Read plates on a microtiter plate reader at 540 nM. $IC_{50}$ values; i.e., the concentration of Compound required to kill one-half of the treated cells, were then calculated.

TABLE 1
Anticancer Activity ($IC_{50}$) Of Enediyne-Saccharide Chimeras
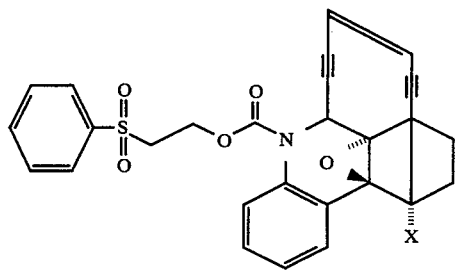
| Number of Compound | $IC_{50}$ (M)* |
|---|---|
| 450: X = $OCH_2CH_2OH$ | $4.0 \times 10^{-5}$ |
| 454a: X = $OCH_2CH_2OR_1$ | $<10^{-4}$ |
| 455a: X = $OCH_2CH_2OR_2$ | $4.4 \times 10^{-5}$ |
| 454b: X = $OCH_2CH_2OR_1$ | $<10^{-4}$ |
| 455b: X = $OCH_2CH_2OR_2$ | $8.7 \times 10^{-6}$ |
| 456a: X = $OCH_2CH_2OR_3$ | $1.4 \times 10^{-7}$** |
| 456b: X = $OCH_2CH_2OR_4$ | $7.6 \times 10^{-6}$** |

TABLE 1-continued

Anticancer Activity (IC$_{50}$) Of Enediyne-Saccharide Chimeras

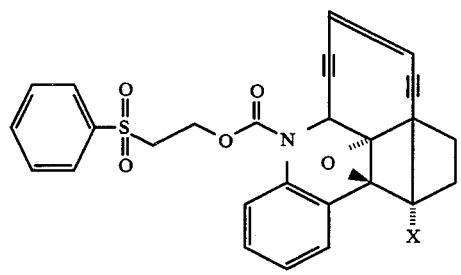

| Number of Compound | IC$_{50}$ (M)* |
|---|---|

*Average date obtained from 5~10 cell lines.
**IC$_{50}$ = 1.0 × 10$^{-9}$ for 456a and 1.0 × 10$^{-10}$ for 456b obtained from MOLT-4 (Leukemia) cell line.

Best Mode for Carrying Out the Invention

Preparation A: Compound 2

Compound 2 was prepared from the 1,2,3-triacetoxy-4,6-benzylidenegalactose derivative reported in *J. Org. Chem.*, 27:3647 (1964) by reaction of that compound with 1.2 equivalents of N-bromosuccinimide (NBS), 0.03 equivalents of azo-bis-iso-butyronitrile (AIBN) and 0.6 equivalents of BaCO$_3$ in benzene at 80 degrees C. for one hour to provide 1,2,3-triacetoxy-4-benzoyloxygalactose. That tri-acetoxy compound was then reacted with 1.2 equivalents of tributylstannane (Bu$_3$SnH) and 0.05 equivalents of AIBN in benzene at 80 degrees C. for 0.75 hours to form 1,2,3-triacetoxy-4-benzyloxyfucose in a yield of 76 percent overall.

That fucose derivative was then reacted in a mixture of 30 percent HBr in acetic acid (HOAc) that itself was mixed with CH$_2$Cl$_2$ (1:1; v:v) as a 1M solution at zero degrees for 20 minutes. Thereafter, the reaction product was reacted with 4 equivalents of Mg and 0.1 equivalent of 12 in THF at 67 degrees C. for five hours to provide fucal Compound 2 in 64 percent yield. R$_f$=0.29 (silica, 25 percent ether in petroleum ether); [α]$^{23}$$_D$+6.7° C. (c=2.2, CHCl$_3$); IR (CHCl$_3$); v$_{max}$, 3029 (m), 2991 (w), 1732 (s), 1650 (m), 1602 (w), 1402 (m), 1372 (m), 1277 (s), 1233 (s), cm$^{-1}$; $^1$H NMR (300 MHz, CDCl$_3$) δ 8.09 (d, J=7.3 Hz, 2 H, aromatic), 7.59 (t, J=7.4 Hz, 1 H, aromatic), 6.56 (dd, J=6.3, 1.8 Hz, 1 H, H-1), 5.67 (m, 1 H, CHO), 5.53 (bd, J=4.3 Hz, 1 H, CHO), 4.70 (ddd, J=6.3, 1.8, 1.8 Hz, 1 H, H-2), 4.33 (q, J=6.6 Hz, 1 H, H-5), 1.95 (s, 3 H, acetate), 1.33 (d, J=6.6 Hz, 3 H, H-6); HMRS (FAB) Calcd. for C$_{15}$H$_{17}$O$_5$ (M+H): 277.1076; found: 277.1079.

Example 1: Compound 3 (Step a, FIG. 4)

The known glycal Compound 2 was reacted with 1.0 equivalents of disobutylaluminum hydride (DIBAL) in CH$_2$Cl$_2$ at −78 degrees C. for 2.5 hours to provide a 72 percent yield of Compound 3, plus 15 percent recovered Compound 2.

Example 2: Compound 4 (Step b, FIG. 4)

Compound 3 was reacted with 2.5 equivalents of 55 percent m-chloroperbenzoic acid (MCPBA) in presence MgSO$_4$ at zero degrees C. for 0.5 hours to provide Compound 4 in 55 percent yield. Rf=0.26 (silica, 2 percent methanol in dichloromethane); [α]$^{23}$$_D$+63.4° C. (c=1.5, CHCl$_3$); IR (CHCl3) v$_{max}$, 3567 (m), 3029 (m), 1730 (s), 1601 (mw), 1577 (m), 1452 (m), 1426 (m), 1388 (m), 1332 (m), 1315 (m), 1273 (s), 1250 (s) cm$^{-1}$; $^1$H NMR (300 MHz, CDCl$_3$) δ 8.07- 7.92 (m, 4 H, aromatic), 7.65-7.41 (m, 5 H, aromatic), 6.52 (d, J=1.1 Hz, 1 H, H-1), 5.56 (d, J=3.4 Hz, 1 H, H-4), 4.35-4.26 (m, 2 H, H-5, CHO), 3.97 (ddd, J=9.7, 1.7, 1.7 Hz, 1 H, CHO), 2.98 (d, J=8.4 Hz, 1 H, OH), 2.76 (d, J=9.7 Hz, 1 H, OH), 1.26 (d, J=6.5 Hz, 3 H, H-6).

Example 3: Compound 5 (Step c, FIG. 4)

Compound 4 was reacted with 1.5 equivalents of t-butyldimethylsilyl chloride ($^t$BuMe$_2$SiCl) and 2.0 equivalents of imidazole in CH$_2$Cl$_2$ at 25 degrees C. for a time period of 30 hours to provide a 67 percent yield of Compound 5.

Example 4: Compound 6 (Step d, FIG. 4)

Oxalyl chloride (1.5 equivalents) and DMSO (2.0 equivalents) were stirred in CH$_2$Cl$_2$ at a temperature of −78 degrees C. for 20 minutes. To that solution was added a solution of Compound 5 (1.0 equivalent) in methylene chloride, and the resulting solution was stirred for one hour at −78 degrees C. Triethylamine (5.0 equivalents) was thereafter added and the resulting reaction mixture was warmed to room temperature over a time period of one hour to provide Compound 6 in 88 percent yield. $R_f=0.47$ (silica, 15 percent ether in petroleum ether); $[\alpha]^{23}_D$ −17.8° C. (c=0.54, CHCl$_3$); IR (CHCl$_3$) $v_{max}$, 2956 (s), 2932 (s), 2860 (s), 1739 (s), 1711 (s), 1633 (s), 1364 (s), 1250 (s) cm$^{-1}$; $^1$H NMR (300 MHz, CDCl$_3$) δ 7.95 (bs, 1 H, aromatic), 7.89 (dd, J=7.7, 0.8 Hz, 1 H, aromatic), 7.54 (dd, J=7.7, 0.9 Hz, 1 H, aromatic), 7.37 (dd, J=7.9, 7.9 Hz, 1 H, aromatic), 6.40 (s, 1 H, H-1), 6.17 (d, J=1.6, Hz, 1 H, H-4), 4.92 (dq, J=6.7, 1.7 Hz, 1 H, H-5), 1.38 (d, J=6.8 Hz, 3 H, H-6), 0.96 (s, 9 H, t-Bu), 0.19 (s, 3 H, CH$_3$); HMRS (FAB) Calcd for C$_{19}$H$_{26}$O$_5$ClSi (M+H): 397.1238; found: 397.1256.

Example 5: Compound 7 (Step e, FIG. 4)

Compound 6 was reacted with 1.2 equivalents of Zn(BH$_4$)$_2$ and 0.5 equivalents of NH$_4$Cl in ether at zero degrees for a time period of 20 minutes to provide Compound 7.

Example 6: β-Hydroxyphthalimide Glycose Compound 9 (Steps e and f, FIG. 4)

In another preparation, to a solution of enone Compound 6 (0.850 g. 2.13 mmol) in ether (5 ml) at zero degrees C. was added ammonium chloride (55 mg, 1.0 mmol) followed by zinc borohydride (16 ml, 2.6 mmol, 0.16 M in ether) and the resulting solution was allowed to stir 20 minutes. The solution was then diluted with cold ether (250 ml), washed with cold saturated NH$_4$Cl (2×100 ml) and cold saturated NaHCO$_3$ (1×100 ml). The solution was dried (MgSO$_4$) and concentrated to yield lactol Compound 7. The crude lactol was dissolved in THF (11 ml) and to this solution was added N-hydroxyphthalimide (0.38 g, 2.3 mmol) and triphenylphosphine (PPh$_3$; 0.67 g, 2.6 mmol). To that solution was added diisopropyl azodicarboxylate (0.51 ml, 2.6 mmol) dropwise and the orange solution was allowed to stir for 30 minutes. The solution was diluted with CH$_2$Cl$_2$ (300 ml) and washed with saturated NaHCO$_3$ (2×150 ml) and H$_2$O (2×150 ml). The solution was dried (MgSO$_4$) and the solvent removed under vacuum. The crude material was chromatographed (silica, CH$_2$Cl$_2$) to give pure β-glycoside Compound 9 (0.617 g, 53 percent).

$R_f=0.36$ (silica, 50 percent ether in petroleum ether); $[\alpha]^{23}_D$ −75.20° C. (c=1.0, CHCl$_3$); IR (CHCl$_3$) $v_{max}$, 3030 (mw), 2958 (m), 2933 (m), 2897 (row), 2887, (row), 2860 (m), 1795 (m), 1741 (vs), 1666 (m), 1577 (w), 1470 (m), 1427 (w), 1390 (m), 1371 (m), 1341 (m), 1316 (m), 1306 (m), 1284 (m), 1278 (m), 1251 (s) cm$^{-1}$; $^1$H NMR (300 MHz, CDCl$_3$) δ 8.09 (dd, J=1.7, 1.7 Hz, 1 H, aromatic), 8.00 (bd, J=7.7 Hz, 1 H, aromatic), 7.83-7.69 (m, 4 H, phthalimide), 7.54-7.50 (m, 1 H, aromatic), 7.39 (dd, J=7.9, 7.9 Hz, 1 H, aromatic), 5.87 (ddd, J=5.8, 2.2, 1.5 Hz, 1 H, H-2), 5.42 (d, J=6.0 Hz, 1 H, H-1), 5.01 (bs, 1 H, H-4), 4.50 (m, 1 H, H-5), 1.37 (d, J=6.7 Hz, 3 H, H-6), 0.79 (s, 9 H, t-Bu), 0.16 (s, 3 H, CH$_3$), 0.10 (s, 3 H, CH$_3$). HMRS (FAB) Calcd for C$_{27}$H$_{31}$O$_7$NClSi (M+H): 544.1558; found: 544.1530.

Example 7: Compound 10 (Step g, FIG. 4)

Compound 9 was reacted with a 1.0 equivalent of hydrazine (NH$_2$NH$_2$) in methanol (MeOH) at 25 degrees C. for a time period of 10 minutes to provide Compound 10.

Example 8: Compound A

D-Fucose was reacted as a 1.0M solution in benzyl alcohol also containing 0.1 equivalent of toluenesulfonic acid (TSA) at a temperature of 65 degrees C. for a time period of three hours. Volatiles were removed and the resulting α-benzyl glycoside was crystallized from ether. Concentration of the ether mother-liquors provided further material for a total yield of 83 percent.

The α-benzyl glycoside was reacted with three equivalents of (CH$_3$)$_2$C(OCH$_3$)$_2$ and 0.1 equivalent of TSA in acetone at 25 degrees C. for 1.5 hours to provide the corresponding 3,4-diacetonide in 92 percent yield.

The above product was reacted with 1.5 equivalents of NaH, 1.5 equivalents of benzylbromide, 0.1 equivalents of tetrabutylammonium iodide in Tetrahydrofuran (THF) at zero to 25 degrees C. over a time period of five hours. The reaction product was treated with 0.6M acetic acid/2N HCl (3:1 v:v) at 25 degrees C. for a time period of two hours to provide 1,2-di-O-benzyl-3,4-dihydroxy fucose in 85 percent yield.

That fucose derivative was reacted with 1.0 equivalents of dibutylstannic oxide (Bu$_2$SnO) in methanol (MeOH) at 80 degrees C. for a time period of one hour. That reaction product was treated with 1.0 equivalents of bromine (Br$_2$) in benzene at 25 degrees C. for a time period of 0.5 hours, to provide Compound A in 76 percent yield.

$R_f=0.27$ (silica, 70 percent ether in petroleum ether); $[\alpha]^{23}_D$ +127° C. (c=1.8, CHCl$_3$); IR (CHCl$_3$) $v_{max}$, 3510 (m), 3068 (m), 3066 (m), 3031 (s), 3013 (s), 2941 (m), 2877 (m), 1729 (s), 1497 (m), 1455 (s), 1368 (m), 1351 (m) cm$^{-1}$; $^1$H NMR (300 MHz, CDCl$_3$) δ 7.44-7.29 (m, 10 H, aromatic), 4.94 (d, J=3.5 Hz, 1 H, H-1), 4.86-4.61 (m, 5 H, H-3, 4 x benzylic), 4.31 (q, J=6.6 Hz, 1 H, H-5), 3.58 (dd, J=9.9, 3.6 Hz, 1 H, J=6.6 Hz, 1 H, H-5), 3.58 (dd, J=9.9, 3.6 Hz, 1 H, H-2), 3.44 (bs, 1 H, OH), 1.25 (d, J=6.5 Hz, 3 H, H-6).

Example 9: Compound 11 (Step h, FIG. 4)

To a thoroughly dried mixture of hydroxylamine Compound 10 (0.526 g, 1.27 mmol) and ketone A (0.521 g, 1.52 mmol) was added benzene (2.5 ml) followed by pyridinium p-toluenesulfonate (PPTS) (32 mg, 0.13 mmol). The solution was allowed to stir for three hours. The solution was then diluted with ethyl acetate (EtOAc) (100 ml), washed with saturated NaHCO$_3$ (2×75 ml) and dried (MgSO$_4$). Following concentration of the solution, chromatography (silica, 50 percent ether in petroleum ether) gave oxime Compound 11 (0.863 g, 92 percent from Compound 9.

$R_f=0.39$ (silica, 50 percent ether in petroleum ether); $[\alpha]^{23}_D$ −31.5° C. (c=1.1, CHCl$_3$); IR (CHCl$_3$) $v_{max}$, 3744 (w), 2935 (m), 2863 (m), 1729 (s), 1671 (m), 1461 (m), 1371 (m), 1310 (m) cm$^{-1}$; $^1$H NMR (300 MHz, CDCl$_3$) δ 8.01 (bs, 1 H, aromatic), 7.92 (d, J=7.8 Hz, 1 H, aromatic), 7.52 (d, J=7.5 Hz, 1 H, aromatic), 7.39-7.28 (m, 11 H, aromatic), 5.64 (dd, J=5.5, 1.7 Hz, 1 H, H-2'), 5.42 (d, J=5.5 Hz, 1 H, H-1'), 5.05 (d, J=1.4 Hz, 1 H, H-4'), 4.91 (d, J=3.2 Hz, 1 H, H-1), 4.76 (q, J=6.8 Hz, 1 H, H-5), 4.73 (d, J=12.3 Hz, 2 H, 2x benzylic), 4.62 (m, 2 H, H-3, benzylic), 4.57 (ddq, J=6.6, 2.0, 2.0 Hz, 1 H, H-5'), 4.52 (d, J=12.4 Hz, 1 H, benzylic), 3.67 (dd, J=6.2, 3.3 Hz, 1 H, H-2), 2.61 (bs, 1 H, OH), 1.39 (d, J=6.8 Hz, 3 H, H-6), 1.28 (d, J=6.5 Hz, 3 H, H-6'), 0.79 (s, 9 H, t-Bu), 0.17 (s, 3 H, CH$_3$-Si), 0.12 (s, 3 H, CH$_3$-Si). HMRS (FAB) calcd. for C$_{39}$H$_{49}$O$_9$NClSi (M+H): 738.2865; found: 738.2844.

Example 10: Compound 12 (Step i, FIG. 4)

Compound 11 was reacted with 1.5 equivalents of t-butyldimethylsilyl triflate ($^t$BuMe$_2$SiOTf) and 2.5 equivalents of 2,6-lutidine at −25 degrees C. for a time period of 0.5 hours to provide Compound 12 in 99 percent yield.

Example 11: Compound 13 (Step j, FIG. 4)

Compound 12 was reacted with 2.5 equivalents of DIBAL in CH$_2$Cl$_2$ at −78 degrees C. for one hour to provide Compound 13 in 91 percent yield.
R$_f$=0.26 (silica, 30 percent ether in petroleum ether); [α]$^{23}$$_D$ +12.6° C. (c=0.7, CHCl$_3$); IR (CHCl$_3$) ν$_{max}$, 3581 (w), 3033 (w), 3011 (m), 2957 (s), 2932 (m), 2897 (m), 2887 (m), 2859 (s), 1727, (w), 1672 (m), 1497 (w), 1471 (m), 1463 (m), 1455 (m), 1363 (m), 1259 (s) cm$^{-1}$; $^1$H NMR (300 MHz, CDCl$_3$) δ 7.35-7.25 (m, 10 H, aromatic), 5.24 (d, J=4.9 Hz, 1 H, H-1'), 5.12 (q, J=6.9 Hz, 1 H, H-5), 5.07 (d, J=2.0 Hz, 1 H, H-1), 4.86 (bs, 1 H, H-4'), 4.85 (d, J=11.8 Hz, 1 H, benzylic), 4.69 (d, J=12.4 Hz, benzylic), 4.63 (d, J=12.3 Hz, 1 H, benzylic), 4.54 (q, J=12.4 Hz, 1 H, benzylic), 4.45 (dq, J=6.7, 1.6 Hz, 1 H, H-5'), 4.41 (d, J=3.5 Hz, 1 H, H-3), 3.99 (bm, 1 H, H-2'), 3.57 (dd, J=3.1, 2.4 Hz, 1 H, H-2), 2.13 (d, J=4.8 Hz, 1 H, OH), 1.43 (d, J=7.0 Hz, 3 H, H-6), 1.21 (d, J=6.6 Hz, 3 H, H-6'), 0.94 (s, 9 H, t-Bu), 0.77 (s, 9 H, t-Bu), 0.19 (s, 6 H, 2×CH$_3$-Si), −0.01 (s, 6 H, 2 ×CH$_3$- Si); HMRS (FAB) Calcd for C$_{38}$H$_{60}$O$_8$NSi$_2$ (M+H): 714.3856; found: 714.3842.

Example 12: Compound 14 (Step k, FIG. 4)

Compound 13 was reacted with one equivalent of thiocarbonyldiimidazole in acetonitrile at 25 degrees C. for 20 hours to provide a mixture of Compounds 14 and 15.

Example 13: Compound 15 (Step 1, FIG. 4)

A solution of thioimidazolide Compound 14 (0.120 g, 0.146 mmol) in toluene (7 ml) was heated at reflux for 40 minutes. The solution was concentrated and chromatographed (silica, 50 percent ether in petroleum ether) to yield thionoimidazolide Compound 15 (0.118 g, 98 percent: and 85 percent overall from Compound 13).
R$_f$=0.30 (silica, 50 percent ether in petroleum ether); [α]$^{23}$$_D$ +87.7° C. (c=1.5, CHCl$_3$); IR (CHCl$_3$) ν$_{max}$, 2957 (s) 2932 (s), 2860 (s), 1697 (s), 1672 (s), 1472 (s), 1364 (s), ; cm$^{-1}$; $^1$H NMR (500 MHz, CDCl$_3$) δ]8.18 (d, J=0.9 Hz, 1 H, imidazole), 7.45 (dd, J=1.5, 1.4 Hz, 1 H, imizadole), 7.36-7.25 (m, 10 H, aromatic), 7.10 (dd, J=1.7, 0.6 Hz, 1 H, imizadole), 5.83 (d, J=2.8 Hz, 1 H, H- 1'), 5.10-5.07 (m, 3 H, H-1, H-5, H-2'), 4.87 (d, J=12.3 Hz, 1 H, benzylic), 4.70 (d, J=12.3 Hz, 1 H, benzylic), 4.67 (d, J=12.3 Hz, 1 H, benzylic), 4.56 (d, J=12.3 Hz, 1 H, benzylic), 4.42 (d, J=3.3 Hz, 1 H, H-3), 4.28 (dq, J=6.8, 1.9 Hz, 1 H, H-5'), 4.05 (d, J=1.8 Hz, 1 H, H-4'), 3.60 (dd, J=3.4, 2.3 Hz, 1 H, H-2), 1.46 (d, J-6.7 Hz, 3 H, H-6'), 1.42 (d, J=7.1 Hz, 3 H, H-6), 0.91, 0.79 (singlets, 9 H each, 2×tBu), 0.25, 0.21, 0.01, 0.00, (singlets, 3 H each, 4×CH$_3$-Si). HMRS (FAB) calcd. for C$_{42}$H$_{62}$O$_8$N$_3$SSi$_2$ (M+H): 824.3796; found: 824. 3836.

Example 14: Compound 16 (Step m, FIG. 4)

Compound 15 was treated with a catalytic amount of NaSMe in ethyl mercaptan at room temperature for a time period of six hours to provide the free mercaptan Compound 16.

Example 15: Compound 17 (Step n, FIG. 4)

Compound 16 was quickly reacted with 2.0 equivalents of 2,4,6-trimethylbenzoyl chloride, 10 equivalents of Et$_3$N and 0.35 equivalents of 4-(dimethylamine)pyridine (DMAP) in CH$_2$Cl$_2$ at 25° C. for 8 hours to provide thioester Compound 17 in 91 percent yield overall from Compound 15.
R$_f$=0.24 (silica, 15 percent ether in petroleum ether); [α]$^{23}$$_D$ +110° C. (C=1.1, CHCl$_3$); IR (CHCl$_3$) ν$_{max}$, 3011 (m), 2957 (s), 2931 (s), 2898 (m), 2886 (m), 2859 (s), 1669 (s), 1655 (w), 1472 (m), 1463 (m), 1455 (m), 1362 (m), 1305 (m), 1259 (s), 1239 (m) cm$^{-1}$; $^1$H NMR (500 MHz, CDCl$_3$) δ 7.35-7.24 (m, 10 H, aromatic), 6.82 (s, 2 H, aromatic), 5.79 (d, J=2.8 Hz, 1 H, H-1'), 5.12-5.08 (m, 2 H, H-5, H-1), 5.01 (d, J=2.8 Hz, 1 H, H-2'), 4.86 (d, J=12.4 Hz, 1 H, benzylic), 4.67 (s, 2 H, 2 x benzylic), 4.54 (d, J=12.4 Hz, 1 H, benzylic), 4.41 (d, J=3.3 Hz, 1 H, H-3), 4.23 (q, J=6.7 Hz, 1 H, H-5'), 4.01 (s, 1 H, H-4'), 3.56 (dd, J=3.1, 2.3 Hz, 1 H, H-2), 2.26 (s, 9 H, 3×CH$_3$-aromatic), 1.47 (d, J=6.81 Hz, 3 H, H-6'), 1.40 (d, J=6.8 Hz, 3 H, H-6), 0.93, 0.76 (singlets, 9 H each, 2×t-Bu), 0.23, 0.18, −0.03, −0.04 (singlets, 3 H each, 4×CH$_3$-Si). HMRS (FAB) calcd. for C$_{48}$H$_{70}$O$_8$NSSi$_2$ (M+H): 876. 4360; found: 876. 4396.

Example 16: Compound 18 (Step o, FIG. 4)

Compound 17 was reacted with 1.0 equivalent of tetrabutylammonium fluoride (TBAF) in THF/H$_2$O HOAc (100:25:1; v:v:v) at zero degrees C. for 20 minutes to provide keto-oxime Compound 18.

Example 17: Compound 19 (Step p, FIG. 4)

Compound 18 was reacted with 2.5 equivalents of K-Selectride® (potassium tri-sec-butylborohydride, 1M in THF) in dimethoxyethane at −78 degrees C. for 1.5 hours to provide α-hydroxy-oxime Compound 19 in 74 percent yield overall from Compound 17.
R$_f$=0.45 (silica, 50 percent ether in petroleum ether); [α]$^{23}$$_D$ +56.6° C. (c=0.8, CHCl$_3$); IR (CHCl$_3$) ν$_{max}$, 3610 (w), 3032 (w), 3012 (m), 2956 (m), 2931 (s), 2859 (m), 1674 (m), 1610 (w), 1471 (m), 1462 (m), 1455 (m), 1370 (m), 1259 (m) cm$^{-1}$; $^1$H NMR (500 MHz, CDCl$_3$) δ 7.35-7.25 (m, 10 H, aromatic), 6.83 (s, 2 H, aromatic), 5.48 (dd, J=9.2, 2.3 Hz, 1 H, H-1), 5.12 (q, J=7.0 Hz, H-5), 5.05 (d, J=2.2 Hz, 1 H, H-1), 4.84 (d, J=12.3 Hz, 1 H, benzylic), 4.69 (d, J=12.4 Hz, 1 H, benzylic), 4.63 (d, J- 12.3 Hz, 1 H, benzylic), 4.55 (d, J=12.3 Hz, 1 H, benzylic), 4.38 (d, J-3.4 Hz, 1 H, H-3), 4.34 (bs, 1 H, H-3'), 4.10 (dq, J=10.2, 6.3 Hz, 1 H, H-5'), 3.77 (dd, J=10.1, 2.6 Hz, 1 H, H-4'), 3.57 (dd, J=3.6, 2.3 Hz, 1 H, H-2), 2.26 (s, 9 H, CH$_3$-aromatic), 2.14 (ddd, J=13.3, 3.2, 3.2 Hz, 1 H, H-2'-eq.), 2.02 (m, 2 H, O-H, H-2'-ax.), 1.40 (d, J=6.8 Hz, 3 H, H-6), 1.38, (d, J=6.2 Hz, 3 H, H-6'), 0.77 (s, 9 H, t-Bu), −0.02 (s, 3 H, CH$_3$-Si). HMRS (FAB) calcd. for C$_{42}$H$_{58}$O$_8$NSSi (M+H): 764.3652; found: 764. 3637.

Example 18: Compound 20 (Step q, FIG. 4)

Compound 19 was reacted with 1.2 equivalents of TBAF in THF at zero to 25 degrees C. for 0.75 hour to provide the unprotected oxime Compound 20 in 100 percent yield.

$R_f$=0.40 (silica, 80 percent ether in petroleum ether); $[\alpha]^{23}_D$ +70° C. (c=0.6, CHCl$_3$); IR (CHCl$_3$) $v_{max}$, 3687 (w), 3601 (W), 3018 (m), 2928 (s), 2856 (m), 1674 (s), 1609 (m), 1455 (m), 1373 (m) cm$^{-1}$; $^1$H NMR (300 MHz, CDCl$_3$) δ 7.34-7.26 (m, 10 H, aromatic), 6.83 (s, 2 H, aromatic), 5.48 (dd, J=9.7, 2.3 Hz, 1 H, H-1'), 4.91 (d, J=3.3 Hz, 1 H, H-1), 4.77-4.69 (m, 2 H, H-5, benzylic), 4.65 (s, 2 H, 2 x benzylic), 4.61 (d, J=5.4 Hz, 1 H, H-3), 4.53 (d, J=12.3 Hz, 1 H, benzylic), 4.32 (bd, J=2.6 Hz, 1 H, H-3'), 4.10 (m, 1 H, H-5'), 3.76 (dd, J=10.5, 2.6 Hz, 1 H, H-4'), 3.66 (dd, J=9.9, 3.3 Hz, 1 H, H-2), 2.70 (bs, 1 H, OH), 2.26 (s, 9 H, 3x CH$_3$— aromatic), 2.13 (ddd, J=13.8, 2.9, 2.9 Hz, 1 H, H-2'-eq.), 2.05 (bs, 1 H, OH), 1.98, (ddd, J=11.8, 11.8, 2.8, Hz, 1 H, H-2'-ax.), 1.48 (d, J=6.8 Hz, 3 H, H-6), .1.40 (d, J=6.4 Hz, 1 H, H-6'). HMRS (FAB) calcd. for C$_{36}$H$_{44}$O$_8$NS (M+H): 650. 2787; found: 650. 2750.

Example 19: Compound 1 (Step r, FIG. 4)

Compound 20 was reacted with 6 equivalents of BH$_3$-NH$_3$ and 6 equivalents of PPTS at 25 degrees C. for a time period of four hours to provide Compound 1 in 85 percent yield.

$R_f$=0.30 (silica, 80 percent ether in petroleum ether); $[\alpha]^{23}_D$ +46.4° C. (c=0.4, CHCl$_3$); IR (CHCl$_3$) $v_{max}$, 3604 (w), 3494 (W), 3031 (m), 3011 (s), 2958 (s), 2928 (s), 2874 (m), 2858 (m), 1726 (w), 1675 (s), 1610 (m), 1497 (w), 1455 (s), 1434 (sh), 1380 (m), 1356 (w), 1335 (w), 1299 (w), 1282 (w), 1263 (w), 1231 (m) cm$^{-1}$; $^1$H NMR (500 MHz, CDCl$_3$) δ 7.39-7.21 (m, 10 H, aromatic), 6.82 (s, 2 H, aromatic), 6.53 (bs, 1 H, NH), 5.01 (dd, J=10.0, 1.8 Hz, 1 H, H-1'), 4.80 (d, J=3.5 Hz, 1 H, H-1), 4.70 (d, J=12.4 Hz, 1 H, benzylic), 4.64 (d, J=12.0 Hz, 1 H, benzylic), 4.56 (d, J=11.9 Hz, 1 H, benzylic), 4.50 (d, J=12.4 Hz, 1 H, benzylic), 4.38 (dd, J=9.7, 9.7 Hz, 1 H, H-3), 4.25 (bs, 1 H, H-3'), 4.05-3.96 (m, 2 H, H-5, H-5'), 3.69 (dd, J=10.7, 2.5 Hz, 1 H, H-4'), 3.38 (dd, J=9.6, 3.6 Hz, 1 H, H-2), 2.97 (bs, 1 H, OH), 2.35 (dd, J=9.9 Hz, 1 H, H-4), 2.26 (s, 3 H, CH$_3$-aromatic), 2.25 (s, 6 H, 2 x CH$_3$-aromatic), 1.97-1.94 (m, 2 H, OH, H-2'-eq.), 1.77 (m, 1 H, H-2'-ax.), 1.38, (d, J=6.2 Hz, 1 H, CH$_3$), 1.27 (d, J=6.2 Hz, CH$_3$). HMRS (FAB) calcd. for C$_{36}$H$_{46}$O$_8$NS (M+H): 652.2944; found: 652.2936.

Example 20: Compound 25 (FIG. 6)

L-Rhamnose was reacted with acetic anhydride [(Ac)$_2$O] a catalytic amount of DMAP in CH$_2$Cl$_2$ at 25 degrees C. to form the tetracetate. Reaction with thiophenol (PhSH) and SnCl$_4$ in CH$_2$Cl$_2$ at zero degrees C. provided the thiophenyl glycoside. Deacylation was accomplished using potassium carbonate in MeOH at 25 degrees C. to provide Compound 25 in about 60 percent overall yield.

Example 21: Compound 26 (Step a, FIG. 6)

Compound 25 was treated with 1.1 equivalents of Bu$_2$SnO in MeOH at 65 degrees C. for two hours, followed by 4 equivalents of MeI and 1.1 equivalents of CsF in dimethyl formamide (DMF) at 25 degrees C. for 12 hours to provide a 65 percent yield of Compound 26 plus 30 percent starting Compound 25.

Example 22: Compound 27 (Step b, FIG. 6)

Compound 26 was reacted with 3.0 equivalents of Ac$_2$O, 3.5 equivalents of Et$_3$N and a catalytic amount of DMAP in CH$_2$Cl$_2$ at zero to 25 degrees C. for a time period of two hours to provide Compound 27 in 95 percent yield.

Example 23: Compound 28 (Step c, FIG. 6)

Compound 27 was reacted with 2 equivalents of diethylaminosulfur trifluoride (DAST) and 1.4 equivalents of NBS in CH$_2$Cl$_2$ at −78 to zero degrees C. for 3 hours to provide Compound 28 in 85 percent yield.

Example 24: Compound 30 (Step d, FIG. 6)

One equivalent of Compound 29, 2.0 equivalents of Compound 28, 4.0 equivalents of SnCl$_2$ and 4.0 equivalents of AgClO$_4$ were reacted in CH$_2$Cl$_2$ in the presence of 4 Å molecular sieves at −20 to zero degrees C. over a 12 hour time period to provide Compound 30 in 80 percent yield.

An improved yield was obtained as follows:

In a round bottomed 500 ml flask wrapped with aluminum foil were added 6.7 g (3.4 eq) of AgClO$_4$ and 6.1 g (3.4 eq) of SnCl$_2$. This mixture of catalysts was azeotroped three times with freshly distilled benzene. 4 Grams of activated powdered 4 Å molecular sieves were added to the flask. This mixture of catalysts and molecular sieves was azeotroped with benzene once more.

3.34 Grams (9.5 mmol, 1.0 eq) of the phenol (Compound 29 were azeotroped three times with benzene in a 100 ml flask, and then dissolved in 47 ml of dry CH$_2$Cl$_2$ (0.2M).

The above amount of Compound 29 was transferred to the 500 ml round bottomed flask. The reaction mixture was cooled down to −20 degrees C. and 3.0 grams (1.2 eq) of azeotropically dried (three times with benzene) of the fluoride compound (Compound 28) dissolved in 57 ml CH$_2$Cl$_2$ (0.2M) was slowly added to the reaction mixture. The reaction mixture was allowed to slowly warm up to room temperature and was stirred at this temperature for two hours.

Then the reaction mixture was again cooled down to −20 degrees C. and another 1.25 g (4.7 mmol; 0.5 eq) of the fluoro Compound 28 dissolved in 24 ml CH$_2$Cl$_2$ (0.2M) were slowly added. The reaction mixture was allowed to reach room temperature and stirred at this temperature for two hours. The above procedure was repeated once more using 0.5 grams (0.1.9 mmol; 0.2 eq) at fluoride Compound 28.

When all the phenol was consumed, the reaction mixture was filtered through a pad of celite and diluted with EtOAc and ether (1:1; v:v, 500 ml total) crushed with 100 ml of saturated aqueous NaHCO$_3$, 100 ml of water and 20 ml of brine. The organic layer was then dried with MgSO$_4$, concentrated, and purified using silica gel with 10 percent benzene-ethyl acetate as eluent to obtain 5.0 grams (8.5 mmol) of coupled material Compound 30 (90 percent yield based on Compound 29).

Example 25: Compound 21 (Step e, FIG. 6)

Compound 30 was treated with 0.5 equivalents of K$_2$CO$_3$ in MeOH at 25 degrees C. over a two hour time period to provide a quantitative yield of Compound 21.

$R_f$=0.20 (silica, 70 percent EtOAc in petroleum ether); mp 137° C.; $[\alpha]^{23}_D$ −47.4° C. (c=0.5, CHCl$_3$); IR(CHCl$_3$) $v_{max}$, 3600 (m), 2950 (m), 1750 (s), 1450 (s), 1400 (s), 1380 (s), 1280 (s) cm$^{-1}$; $^1$H NMR (300 MHz, CDCl$_3$) δ 5.72 (s, 1 H, H-1), 4.45 (s, 1 H, H-2), 4.18-4.15 (m, 1 H, H-5), 3.90 (s, 3 H, H$_3$CO), 3.85 (s, 3 H, H$_3$CO), 3.82-3.80 (m, 4 H, H$_3$CO H-3), 3.61 (dd, J=9.5, 9.4 Hz, H-4), 3.54 (s, 3 H, H$_3$CO), 2.44 (s, 1 H, HO), 2.34 (s, 3 H, H$_3$C-aromatic), 1.27 (d, J=6.2 Hz, H-6).

Example 26: Compound 31 (Step f, FIG. 6)

Compound 21 was treated with 2.5 equivalents of Et$_3$SiOTf and 3.0 equivalents of 2,6-lutidine in CH$_2$Cl$_2$ at −20 to zero degrees C. for one hour to provide Compound 31 in 92 percent yield.

Example 27: Compound 32 (Step g, FIG. 6)

Compound 31 was treated with 2.5 equivalents of DIBAL in CH$_2$Cl$_2$ at −78 to zero degrees C. for two hours to provide Compound 32 in 90 percent yield.

Example 28: Compound 33 (Step h, FIG. 6)

Compound 32 was reacted with 0.02 equivalents of RuCl$_3$ hydrate and 4.0 equivalents of NaIO$_4$ in a solvent of CCl$_4$/CH$_3$CN/H$_2$O (2:2:3; v:v:v) at zero to 25 degrees C. for three hours to provide Compound 33 in 75 percent yield.

Example 29: Compound 34 (Step i, FIG. 6)

Compound 33 was reacted with 1.5 equivalents of phenyl dichlorophosphate [PhOP(O)Cl$_2$], 4.0 equivalents of pyridine and 2.0 equivalents of thiophenol (PhSH) in dimethoxyethane at zero to 25 degrees C. for one hour to provide compound 34 in 90 percent yield.

Example 30: Compound 22 (Step j, FIG. 6)

Compound 34 was reacted with 2.2 equivalents of TBAF in THF at zero degrees C. for 0.5 hours to provide Compound 22 in 90 percent yield. (c=0.35, CHCl$_3$); IR (CHCl$_3$) $v_{max}$, $R_f$=0.23 (silica, 70 percent EtOAc in petroleum ether); mp 140° C.; $[\alpha]^{23}_D$ −36.2° C. (c=0.35, CHCl$_3$); IR(CHCl$_3$) $v_{max}$, 3600 (m), 3026 (m), 3010 (m), 2939 (m), 1685 (s), 1478 (s), 1458 (m) cm$^{-1}$; $^1$H NMR (300 MHz, CDCl$_3$) δ]7.48-7.45 (m, 2 H, aromatic), 7.40-7.37 (m, 3 H, aromatic), 5.67 (d, J=1.4 Hz, 1 H, H-1), 4.41 (dd, J=2.8, 1.6 Hz, 1 H, H-2), 4.20-4.13 (m, 1 H, H-5), 3.89 (s, 3 H, H$_3$CO), 3.80-3.76 (m, 4 H, H$_3$CO, H-4), 3.58 (dd, J=9.4, 9.4 Hz, H-4), 3.51 (s, 3 H, H$_3$CO), 2.38 (s, 3 H, H$_3$C-aromatic), 1.24 (d, J=6.3 Hz, H-6).

Example 31: Compound 36 (Step a, FIG. 7)

Methyl serine hydrochloride (Compound 35) was treated with 1.1 equivalents of carbonyldiimidazole and 1.0 equivalents of DMAP in a CH$_3$CN at 80 degrees C. for two hours to provide Compound 36 in 95 percent yield.

Example 32: Compound 37 (Step b, FIG. 7)

Compound 36 was treated with 1.0 equivalents of NaH and 4 equivalents of ethyl iodide (EtI) in DMF at zero degrees C. for 0.5 hours to provide Compound 37 in 75 percent yield.

Example 33: Compound 38 (Step c, FIG. 7)

Compound 37 was treated with 1.5 equivalents of DIBAL in toluene at −78 degrees C. for 1.5 hours to provide Compound 38.

Example 34: Compound 39 (Step d, FIG. 7)

Compound 38 was treated with 1.2 equivalents of (−)-β-methoxydiisopinocampheylborane and 1.2 equivalents of allylmagnesium bromide in ether at −78 to 25 degrees C. over a four hour time period. Thereafter, 3N NaOH and 30 percent H$_2$O$_2$ were added and the reaction mixture was maintained at 40 degrees C. for one hour to provide Compound 39 in 43 percent overall yield from Compound 37.

Example 35: Compound 40 (Step e, FIG. 7)

Compound 39 was reacted with 1.2 equivalents of Ag$_2$O and 5 equivalents of MeI in DMF at 40 degrees C. for 12 hours to provide Compound 40 in 92 percent yield.

Example 36: Compound 41 (Step f, FIG. 7)

Compound 40 was treated with ozone in CH$_2$Cl$_2$/MeOH (1:1; v:v) at −78 degrees C., followed by 2.0 equivalents of trimethyl phosphite [P(OMe)$_3$] at −78 to 25 degrees C. for 14 hours to provide Compound 41 in 91 percent yield. Example 37: Compound 42 (Step q, FIG. 7)

Compound 41 was dissolved in MeOH in the presence of Amberlyst-15 resin at 25 degrees C. for 17 hours to provide the acetal Compound 42 in 85 percent yield.

Example 38: Compound 43 (Step h, FIG. 7)

Compound 42 was treated with 1.5 equivalents of NaOH in MeOH/H$_2$O (2:1; v:v) at 90 degrees C. for one hour to provide Compound 43 in 95 percent yield.

Example 39: Compounds 23 and 24 (Step i, FIG. 7)

Compound 43 was treated with 1.5 equivalents of HCl in MeOH at 25 degrees C. for three hours to provide Compounds 23 and 24 as a mixture in 88 percent yield. Compounds 23 and 24 were separately obtained by recrystalization from ethyl acetate (EtOAc).

Compound 23: $R_f$=0.27 (silica, 10 percent MeOH in EtOAc); $[\alpha]^{23}_D$ −56.7° C. (c=1.0, CHCl$_3$); IR (CHCl$_3$) $v_{max}$ 3012 (m), 2969 (s), 2937 (s), 2911 (s), 2834 (m), 1466 (m), 1446 (m), 1376 (m), 1358 (w), 1248 (m), 1202 (m), 1154 (m), 1127 (s) cm$^{-1}$; $^1$H NMR (300 MHz, C$_6$D$_6$) δ 4.66 (dd, J=3.5, 2.3 Hz, 1 H, H-1), 3.79 (dd, J=11.0, 4.7 Hz, 1 H, H-5 eq), 3.61-3.51 (m, 2 H, H-5 ax, H-3), 3.15 (s, 3 H, H$_3$CO), 3.03 (s, 3 H, H$_3$CO), 2.74 (ddd, J=9.7, 9.0, 4.6 Hz, 1 H, H-4), 2.52-2.38 (m, 2 H, H$_2$CN), 2.11 (ddd, J=12.7, 4.5, 2.2 Hz, 1 H, H-2 eq), 1.47 (ddd, J=12.7, 10.5, 3.6 Hz, 1 H, H-2 ax), 1.30 (bs, 1 H, HN), 0.91 (t, J=7.1 Hz, 3 H, H$_3$C).

Compound 24: $R_f$=0.18 (silica, 10 percent MeOH in EtOAc); $[\alpha]_D^{25}$ +99.7° C. (c=1.0, CHCl$_3$); IR (CHCl$_3$) $v_{max}$ 2971 (s), 2836 (s), 2700 (s), 2457 (m), 1584 (m), 449 (m), 1392 (m), 1239 (m), 1191 (m) cm$^{-1}$; $^1$H NMR (300 MHz, C$_6$D$_6$) δ 4.14-4.07 (m, 2 H, H-5 eq, H-1), 3.37 (s, 3 H, H$_3$CO), 3.07 (dd, J=9.6, 9.1 Hz, 1 H, H-5 ax), 3.07-300 (m, 2 H, H-3, H$_3$CO), 2.65 (ddd, J=9.0, 9.0, 4.5 Hz, 1 H, H-4), 2.46-2.33 (m, 2 H, H$_2$C-N), 2.13 (ddd, J=12.5, 4.5, 2.4 Hz, 1 H, H-2 eq), 1.96 (bs, 1 H, HN), 1.59 (ddd, J=12.4, 10.5, 8.9 Hz, 1 H, H-2 ax), 0.89 (t, J=7.1 Hz, 3 H, H$_3$C).

Example 40: Compound 44 (FIG. 8)

D-Fucose is reacted with excess $Ac_2O$ to form the tetracetate derivative. The fucose tetraacetate is then reacted with 30 percent HBr in HOAc to prepare the 1-bromo-2,3,4-triacetate derivative. That compound is reacted with MeOH in the presence of $Ag_2CO_3$ to form the methyl glycoside. The acetate groups are removed and the resulting triol is reacted with carbonyl diimidazole and then 2N HCl in THF to form the 3,4-carbonate derivative, Compound 44.

Example 41: Compound 45 (Step a of FIG. 8)

A mixture of Compounds 23 and 24, $K_2CO_3$ (1.5 equivalents) and 9-fluorenylmethyl chloroformate (1.5 equivalents) in $THF/H_2O$ (7:3, v:v) was stirred at zero degrees C. for 30 minutes to provide the corresponding FMOC derivatives in 93 percent yield. Those derivatives were stirred in a solution of $HOAc/H_2O$ (3:1, v:v) at 90 degrees C. to provide a mixture of the corresponding 1-hydroxy compounds, including Compound 45a in 95 percent yield.

Example 42: Compound 45b (Step b, FIG. 8)

Compound 45a was reacted with 5.0 equivalents of DAST in THF and in the presence of 4 Å molecular sieves at a temperature of −78 to zero degrees C. over a time period of one hour to provide the fluoride Compound 45b in 92 percent yield.

Example 43: Compound 46 (Step c, FIG. 8)

A suspension of anhydrous silver perchlorate (0.97 g. 4.7 mmol) and stannous chloride (0.88 g. 4.7 mmol), dried by azeotropic removal of benzene, and powdered activated 4 Å molecular sieves (1 g) and ether (20 ml) was allowed to stir at 25 degrees C. for 15 minutes and then cooled to −50 degrees C. To this mixture was added a solution of fluoride Compound 45a (0.936 g. 2.34 mmol) and alcohol Compound 44 (0.720 g. 3.53 mmol), twice dried by azeotropic removal of benzene, in acetonitrile (20 ml) slowly (five minutes) and allowed to gradually warm to zero degrees C. (two hours). The mixture was diluted with ether (150 ml) and filtered through celite, and the residue washed with ether (3×75 ml). The combined filtrates were again filtered to remove the insoluble alcohol Compound 44. The resulting solution was washed with saturated $NaHCO_3$ (7×200 ml) and brine (1×200 ml). The solution was then dried ($MgSO_4$) and concentrated. Gradient elution chromatography of the crude product (silica, 50 percent ethyl acetate in petroleum ether to ethyl acetate) gave the pure Compound 46 α-glycoside (0.701 g. 51 percent) and β-anomer (0.164 g, 12 percent).

Example 44: Compound 47 (Step d, FIG. 8)

Compound 46 was reacted with 0.5 equivalents of $K_2CO_3$ in ethylene glycol/THF (1:20, v:v) at 25 degrees C. for 0.25 hours to provide Compound 47 in 93 percent yield.

Example 45: Compound 48 (Step e, FIG. 8)

Compound 47 was reacted with 1.0 equivalents of $Bu_2SnO$ in MeOH at 65 degrees C. for 0.75 hours, and then with 1.0 equivalents of bromine ($Br_2$) in benzene in the presence of 4 Å molecular sieves for 0.5 hours to provide a 70 percent yield of Compound 48, plus 18 percent of Compound 47.

Example 46: Compound 49 (Step f, FIG. 8)

Compound 48 was reacted with 1.2 equivalents of Compound 10 and 0.05 equivalents of PPTS in benzene at 25 degrees C. for two hours to form Compound 49 in 83 percent yield.

Example 47: Compound 50 (Step g, FIG. 8)

Compound 49 was reacted with 1.3 equivalents of $^tBuMe_2SiOTf$ and 1.7 equivalents of 2,6-lutidine in $CH_2Cl_2$ at zero to 25 degrees over two hours to provide a quantitative yield of Compound 50.

Example 48: Compound 51 (Step h, FIG. 8)

Compound 50 was reacted with 3.0 equivalents of DIBAL in $CH_2Cl_2$ at −78 degrees C. for 0.5 hours to provide Compound 51 in 91 percent yield.

Example 49: Compound 52 (Step i, FIG. 8)

Compound 51 was reacted with 3.0 equivalents of thiocarbonyldiimidazole in acetonitrile at 25 degrees C. for four hours to provide Compound 52 in 87 percent yield.

Example 50: Compound 53 (Step j, FIG. 8)

Compound 52 was heated in toluene at 110 degrees C. for 0.5 hours to form the rearranged Compound 53 in 98 percent yield.

Example 51: Compound 54 (Step k, FIG. 8)

Compound 53 was reacted with a catalytic amount of NaSMe in ethyl mercaptan for six hours at room temperature to provide Compound 54 in 88 percent yield.

Example 52: Compound 55

Compound 55, the acid chloride of Compound 33, was prepared by reacting Compound 33 with $(COCl)_2$ at 25 degrees C. for one hour to provide Compound 55 in 95 percent yield.

Example 53: Compound 56 (Step a, FIG. 9)

To a solution of acid chloride Compound 55 (0.168 g, 0.217 mmol) in methylene chloride (1.0 ml) was added thiol Compound 54 (0.145 g, 0.154 mmol) followed by 3 equivalents of DMAP (56 mg, 0.56 mmol). The solution was stirred six hours, and then diluted with ethyl acetate (60 ml), washed with saturated $NH_4Cl$ (2×40 ml), saturated $NaHCO_3$ (2×40 ml) and dried ($MgSO_4$). The solution was concentrated and chromatographed (silica, 30 percent ether in petroleum ether) to yield thioester Compound 56 (0.132 g, 52 percent) and starting thiol Compound 54 (59 mg, 41 percent).

Example 54: Compound 57 (Step b, FIG. 9)

Compound 56 was reacted with 1.0 equivalent of TBAF and 3.5 equivalents of HOAc in THF at −23 degrees C. for 0.25 hour to form Compound 57.

Example 55: Compound 58 (Step c, FIG. 9)

Compound 57 was reacted with 3 equivalents of K-Selectride in dimethoxyethane/THF (9:1, v:v) at −78 degrees C. for 1.5 hours to provide Compound 58 in a 75 percent yield overall from Compound 56.

Example 56: Compound 59 (Step d, FIG. 9)

Compound 58 is reacted with 3 equivalents of TBAF in THF to provide Compound 59.

Example 57: Compound 60 (Step e, FIG. 9)

Compound 59 is reacted with NH$_3$-BH$_3$ and PPTS in CH$_2$Cl$_2$ as discussed before to provide Compound 60.

Example 58: Compound 100 (Step f, FIG. 9)

Compound 60 is reacted in morpholine/THF (1:1, v:v) to remove the FMOC group and provide the calicheamicin $\gamma_1^I$ oligosaccharide, Compound 100.

Example 59: Compound 61 (Step g, FIG. 9)

Compound 100 is acylated with Ac$_2$O in the presence of Et$_3$N and DMAP in CH$_2$Cl$_2$ as discussed previously to form the acetoxy Compound 61.

Example 60: Compound 62 (FIG. 10)

Compound 62 is the o-nitrobenzyl analog of Compound 44, and is prepared analogously. Thus, D-fucose is acylated with Ac$_2$O to form the tetraacetate, and thereafter reacted with HBr/HOAc to form 1-bromo-2,3,4-triacetoxyfucose. That material is then reacted with o-nitrobenzyl alcohol in the presence of Ag$_2$CO$_3$ to form the o-nitrobenzyl glycosyl triacetate. Deacylation, followed by reaction with carbonyl diimidazole and 2N HCl in THF affords Compound 62.

Example 61: Compound 63 (FIG. 12)

Compound 63 is prepared from Compound 62 in a manner similar to the preparation of keto portion of Compound 48. Thus, Compound 62 is reacted with $^t$BuMe$_2$SiCl to block the 2-position hydroxyl group. The 3,4-carbonate blocking group is removed with NaOMe in THF/MeOH (K$_2$CO$_3$ in ethylene glycol/THF can also be used). The 4-position hydroxyl is thereafter oxidized using 1.0 equivalent of Bu$_2$SnO in MeOH at 65 degrees C., followed by 1.0 equivalent of Br$_2$ in benzene in the presence of 4 Å molecular sieves at 25 degrees C.

Example 62: Compound 167 (FIG. 13)

This synthesis begins with Compound 148, which was prepared in a manner analogous to that of Compound 48. Thus, Compound 148 was reacted in step (a) with 1.1 equivalents of O-benzylhydroxylamine and a catalytic amount of PPTS in benzene at 25° C. for 0.5 hours to provide Compound 160 in 90 percent yield. Compound 160 was then reacted in step (b) with one equivalent of Et$_3$SiOTf and 1.2 equivalents of 2,6-lutidine in dichloromethane at zero degrees C. for 0.5 hours to provide Compound 161 in 98 percent yield. Ultraviolet irradiation of Compound 161 (step c) in THF-H$_2$O (9:1, v:v) at zero degrees C. for 15 minutes provided Compound 162 in 95 percent yield.

Reaction of Compound 162 with a catalytic amount of sodium hydride in trichloracetonitrilemethylene chloride (1:12, v:v) at 25° C. for two hours produced Compound 163 in 98 percent yield in step (d), whereas reaction with three equivalents of DAST in THF from −78° to zero degree C. for one hour in step d' produced Compound 163a in 90 percent yield. Reaction of Compound 163 with two equivalents of benzyl alcohol and one equivalent of BF$_3$-etherate in methylene chloride at −60° C. to −30° C. provided a 95 percent yield of Compound 164, in an $\alpha$:$\beta$ ratio of about 1:5 (step e). Reaction of Compound 163a with 1.2 equivalents of benzyl alcohol, 1.2 equivalents of silver silicate with a catalytic amount of SnCl$_2$ in methylene chloride at 25° C. for three hours also provided Compound 164, in 85 percent yield with about equal amounts of $\alpha$ and $\beta$ anomers (step e').

Reaction of Compound 164 with excess pyridinium hydrofluoride in CH$_2$Cl$_2$-THF (7:1, v:v) at zero degrees C. for 20 minutes provided Compound 165 in 98 percent yield (step f). Reaction of Compound 165 in diethyamine-THF (1:1, v:v) at 25° C. for two hours provided Compound 166 in 98 percent yield (step g). Finally, reaction of Compound 166 with excess titanium tetraisopropoxide and excess diphenylsilane in methylene chloride at 25° C. for one hour provided Compound 167 in 92 percent yield.

Compound 167 pale yellow oil; R$_f$=0.31 (silica, 10 percent methanol in dichloromethane), $[\alpha]_D^{23}$= −49.2° (c=0.66, CHCl$_3$); $^1$H NMR, (500 MHz, C$_6$D$_6$): $\delta$=7.56 (d, 2 H, J=7.6 Hz, Ar), 7.32-7.13 (m, 8H, Ar), 5.88 (bs, 2 H, O H), 5.86 (s, 1 H, E-1), 5.75 (bs, 1 H, O-N-H), 4.99 (d, 1 H, J=11.7 Hz, CH$_2$-Ph), 4.67 (d, 1 H, J=11.7 Hz, CH$_2$-Ph), 4.54-4.47 (m, 3 H, A-1, CH$_2$-Ph-hydroxylamine), 4.32 (dd, 1 H, J=10.8, 9.2 Hz, E-5ax), 4.04 (dd, 1 H, J=9.5, 9.5 Hz, A-3), 4.02-3.94 (m, 1 H, E-3), 3.90 (dd, 1 H, J=10.8, 4.7 Hz, E-5eq), 3.88 (dd, 1 H, J=9.5, 7.6 Hz, A-2), 3.57 (dq, 1 H, J=9.5, 6.0 Hz, A-5), 3.23 (s, 3 H, OCH$_3$), 2.82 (ddd, 1 H, J=9.2, 9.2, 4.7 Hz, E-4), 2.57-2.42 (m, 3 H, E-2 eq, N-CH$_2$), 2.34 (dd, 1 H, J=9.5, 9.5 Hz, A-4), 1.54 (dd, 1 H, J=10.2, 10.2 Hz, E-2ax), 1.36 (d, 3 H, J=6.0 Hz, A-6), 0.99 (t, 3 H, J=6.5 Hz, N-CH$_2$-CH$_3$); IR (CHCl$_3$): $\nu_{max}$=2964, 2932, 1456, 1095, 1071 (cm$^1$; HRMS calcd. for C$_{28}$H$_{40}$N$_2$O$_7$ (M+Cs) 649.1890; found 649.1900.

Example 63: Compounds 307a and 307b (FIG. 14)

Compound 300 (Nicolaou et al., *J. Am. Chem. Soc.*, 112:7416 (1990)] was reacted with 3.0 equivalents of ethyl bromoacetate, 2.0 equivalents of CsCO$_3$ with one equivalent of 18-crown-6 in acetonitrile at 50° C. for five hours to provide Compound 301 in 60 percent yield (step a). Reaction of Compound 301 with 2.0 equivalents of LiOH in THF-H$_2$O (1:1, v:v) for 0.5 hour, followed by 1.1 equivalents of dithiodipyridine, 1:1 equivalents of triphenylphosphine in dichloromethane at 25° C. for 0.5 hours provided Compound 302 in 92 percent yield (step b). Compound 302 was reacted with 5.0 equivalents NaBH$_4$ in CH$_2$Cl$_2$-$^i$PrOH (1:1, v:v) at 25° C. for 20 minutes to provide the primary alcohol Compound 303 in 92 percent yield.

One equivalent of each of Compounds 303 and 163 were reacted with a catalytic amount of BF$_3$-etherate in methylene chloride at −60° C. to −40° C. for one hour to provide an 84 percent yield of Compounds 304a and 304b with an $\alpha$:$\beta$ ratio of about 5:1 (step d). Protecting groups were removed from the disaccharide as in Example 62, again with two 98 percent yields to provide Compounds 306a and 306b (steps e and f). Mixed Compounds 306a and 306b were reduced with an excess of titanium tetraisopropoxide and diphenylsilane in methylene chloride at 25° C. for one hour to provide a 90 percent yield of diostereomeric Compounds 307a and 307b.

Compound 307a pale yellow oil; R$_f$=0.39 (silica, 10 percent methanol in dichloromethane), $[\alpha]_D^{25}$= −87.3° (c=0.48, CHCl$_3$), $^1$H NMR, (500 MHz, C$_6$D$_6$): $\delta$=8.97 (dd, 1 H, J=4.2, 0.7 Hz, Dyn-Ar), 7.52 (m, 1 H, Dyn-Ar), 7.41-6.98 (m, 12 H, 11 Ar, propargylic H), 6.98 (dd, 1 H, J=7.1, 7.1 Hz, Dyn-Ar), 5.89 (bs, 1 H, OH), 5.83 (bs, 1 H, O-N-H), 5.78 (s, 1 H, E-1), 5.28 (d, 1 H, J=10.0 Hz, Vinylic H), 5.10 (dd, 1 H, J=10.0, 1.7 Hz, Vinylic H), 4.58-4.51 (m, 2 H, CH$_2$-Ph), 4.50 (d, 1 H, J=7.4, A-1), 4.48-4.40 (m, 1 H, E-5ax), 4.25-4.17 (m, 1 H, E-5eq), 4.13-4.02 (m, 3 H, A-3, OCH$_2$CH$_2$O), 4.01-3.94 (m, 1 H, OCH$_2$CH$_2$O), 3.93-3.90 (m, 1 H, E-3), 3.77 (dd, 1 H, J=9.5, 7.3 Hz, A-2), 3.69-3.52 (m, 1 H, A-5), 3.26 (s, 3 H, OCH$_3$), 2.78-2.66 (m, 2 H, E-4, N-CH$_2$), 2.65-2.57 (m, H, N-CH$_2$), 2.47 (dd, 1 H, J=12.0, 2.2 Hz, E-2eq), 2.44 (dd, 1 H, J=9.5, 9.5 Hz, A-4), 2.31 (dd, 1 H, J=14.5, 6.5 Hz, Dyn-CH$_2$), 2.04 (d, 1 H, J=6.7 Hz, Dyn-CH$_2$), 1.95-1.83 (m, 4 H, CH$_2$), 1.43 (dd, 1 H, J=14.5, 9.3 Hz, E-2ax), 1.33 (d, 3H, J=6.1 Hz, A-6), 1.04 (t, 3 H, J=6.5 Hz, N-CH$_2$-CH$_3$); IR (CHCl$_3$) v$_{max}$=2965, 2931, 1733, 1380, 1323, 1146, 1098, 1071 cm$^{-1}$; HRMS calcd. for C$_{49}$H$_{55}$N$_3$O$_{11}$ (M+Cs*) 994.2891; found 994.2904.

Compound 307b: pale yellow oil; R$_f$=0.38 (silica, 10 percent methanol in dichloromethane), [α]$_D^{25}$=125.7° (c=0.68, CHCl$_3$), $^1$H NMR (500MHz, C$_6$D$_6$): δ=8.93 (dd, 1 H, J=4.2, 0.7 Hz, Dyn-Ar), 7.56 (dd, J=7.4, 1.4 Hz, Dyn-Ar), 7.32-7.02 (m, 12 H, 11 Ar, propagylic H), 6.90 (dd, 1 H, J=7.1, 7.1 Hz, Dyn-Ar), 5.90 (bs, 1 H, O-N-H), 5.88 (bs, 1 H, OH), 5.82 (s, 1 H, E-1), 5.29 (d, 1 H, J=10.2 Hz, vinylic H), 5.11 (dd, 1 H, J=10.2, 1.7 Hz, vinylic H), 4.56-4.51 (m, 2 H, CH$_2$Ph), 4.49 (dd, 1 H, J=11.1, 9.0 Hz, E-5ax), 4.48 (d, 1 H, J=7.4 Hz, A-1), 4.22-4.17 (m, 2 H, OCH$_2$CH$_2$O), 4.14 (dd, 1 H, J=11.1, 4.7 Hz, E-5eq), 4.09 (dd, 1 H, J=9.5, 9.5 Hz, A-3), 4.06-4.01 (m, 1 H, OCH$_2$CH$_2$O), 3.93-3.88 (m, 1 H, OCH$_2$CH$_2$O), 3.87-3.81 (m, 1 H, E-3), 3.78 (dd, 1 H, J=9.5, 7.1 Hz, A-2), 3.58 (dq, 1 H, J=9.5, 6.1 Hz, A-5), 3.27 (s, 3 H, OCH$_3$), 2.84 (ddd, 1 H, J=9.0, 9.0, 4.7 Hz, E-4), 2.77 (m, 2 H, N-CH$_2$), 2.54 (dd, 1 H, J=12.2, 2.5 Hz, E-2eq), 2.42 (dd, 1 H, J=9.5, 9.5 Hz, A-4), 2.30 (dd, 1 H, J=14.6, 10.5 Hz, Dyn-CH$_2$), 2.06 (dd, 1 H, J=14.6, 7.1 Hz, Dyn-CH$_2$), 1.97-1.83 (m, 4 H, Dyn-CH$_2$), 1.51 (dd, 1 H, J=12.2, 9.2 Hz, E-2ax), 1.33 (d, 3 H, J=6.1 Hz, A-6), 1.10 (t, 3 H, J=6.5 Hz, N-CH$_2$-CH$_3$); IR (CHCl$_3$): v$_{max}$=2962, 2957, 2929, 1733, 1386, 1323, 1146, 1097, 1070 cm$^{-1}$; HRMS calcd. for C$_{49}$H$_{55}$N$_3$O$_{11}$ (M+Cs*) 994.2891: found 994.2904.

Example 64: Biologically Active Agent

A suspension of anhydrous silver perchlorate (1.0 mmol) and stannous chloride (1.0 mmol), dried by azeotropic removal of benzene, and powdered activated 4 Å molecular sieves (0.3 g) and methylene chloride (2 ml) is stirred at 25 degrees C. for 15 minutes and then cooled to −78 degrees C. To this mixture is added a solution of fluoride Compound 202 or Compound 224 (0.5 mmol) and aglycone alcohol HZ (1.0 mmol), twice dried by azeotropic removal of benzene, in methylene chloride (3 ml) slowly (one minute), and the resulting solution is allowed to gradually warm to zero degrees C. (two hours). The mixture is diluted with ether (50 ml) and filtered through celite and the residue washed with ether (3×30 ml). The combined filtrates are washed with saturated NaCO$_3$ (7×200 ml) and brine (1×200 ml). The solution is then dried (MgSO$_4$) and concentrated. Chromatography of the crude product (silica) provides the pure α-glycoside and β-anomer, Compound 203 or Compound 225 and then deprotected to form Compounds 205 and 226.

Example 65: Compound 322 (Step e, FIG. 17)

R$_f$=0.27 (silica gel, 60 percent ethyl acetate in benzene); [α]$_D^{25}$ −330° (c=0.63, CHCl$_3$); $^1$H NMR (500 MHz, C$_6$D$_6$) δ 7.50-7.48 (m, 2 H, SPh), 7.06-7.02 (m, 2 H, SPh), 6.96-6.93 (m, 1 H, SPh), 5.52 (d, J=5.8 Hz, 1 H, C-1), 4.20 (q, J=6.5 Hz, 1 H, C-5), 3.90-3.83 (b, 1 H, C-3), 3.34 (b, 1 H, C-4), 2.70 (b, 1 H, OH), 2.62 (b, 1 H, OH), 2.16-2.03 (m, 1 H, C-2 ax), 1.92 (dd, J=13.3, 5.0 Hz, 1 H, C-2 eq) 1.18-1.16 (m, 3 H, C-6); $^{13}$C NMR (125 MNz, C$_6$D$_6$) δ 131.0, 129.1, 128.3, 126.9, 84.3, 71.4, 67.3, 66.7, 33.7, 16.8; IR (CHCl$_3$) v$_{max}$ 3330, 2977, 1478, 1439, 1217, 1162, 1093, 1050, 975, 820 cm$^{-1}$; HRMS Calcd. for C$_{12}$N$_{16}$O$_3$S (M+Na+): 263.0718. Found 263.0718. Anal. Calcd. for C$_{12}$H$_{16}$O$_3$S: C, 59.98; H, 6.72; 5, 13.32. Found: C, 59.92; H, 6.67; S, 13.33.

Example 66: Compound 328 Step 1, FIG. 17)

R$_f$=0.35 (silica gel, 5 percent ethyl acetate in benzene); [α]$_D^{26}$ −166° (C=0.42, CHCl$_3$); $^1$H NMR (500 MHz, C$_6$D$_6$) δ 11.96 (s, 1 H, NH), 8.63 (s, 1 H, aromatic), 7.50-7.48 (m, 2 H, SPh), 7.47 (s, 1 H, aromatic), δ 7.32-7.28 (m, 2 H, SPh), 7.26-7.22 (m, 1 H, SPh), 5.77 (d, J=5.4 Hz, 1 H, C-1), 5.49 (d, J=2.5 Hz, 1 H, vinyl), 5.40 (ddd, J=12.6, 4.5, 2.5 Hz, 1 H, C-3), 4.58 (d, J'22.5 Hz, 1 H, vinyl), 4.45 (q, J=6.5, Hz, 1 H, C-5) 4.11 (bin, 1 H, C-4), 3.99 (s, 3 H, OCH$_3$), 3.87 (5,3 H, OCH$_3$), 3.83 (s, 3 H, OCH$_3$), 2.81 (ddd, J=12.6, 12.6, 5.4 Hz, 1 H, C-2 ax), 2.03 (dd, J =12.6, 4.5 Hz, 1 H, C-2 eq), 1.24 (d, J=6.5 Hz, 3 H, C-6), 0.90 (t, J=7.9 Hz, 9 H, SiCH$_2$CH$_3$), 0.58-0.52 (m, 6 H, SiCH$_2$CH$_3$); $^{13}$C NMR (125 MHz, C$_6$D$_6$) δ 167.0, 161.0, 154.5, 154.0, 144.0, 137.2, 135.1, 128.9, 126.9, 112.3, 107.4, 103.8, 90.6, 83.9, 71.5, 70.5, 67.9, 56.1, 56.0, 30.2, 17.1, 6.9, 5.2; IR (CDCl$_3$) v$_{max}$ 3262, 2955, 2875, 1682, 1594, 1518, 1464, 1308, 1252, 1212, 1155, 1088, 1057, 1037, 1006, 734 cm$^{-1}$; HRMS Calcd. for C$_{31}$H$_{43}$O$_8$NSSi (M+Cs+): 750.1533. Found: 750.1536. Anal. Calcd. for C$_{31}$H$_{43}$O$_8$NSSi: C, 60.27; H, 7.02; N, 2.27; 5, 5.18; 5, 4.53. Found: C, 60.41; H, 6.96; N, 2.30; 5,5.16; Si, 4.75.

Example 67: Compound 247

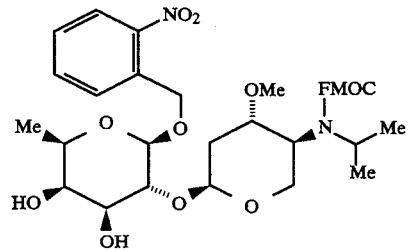

247

R$_f$=0.54 (silica gel, ethyl acetate); [α]$_D^{25}$ −34.3° (c=0.35, CHCl$_3$); $^1$H NMR (500 MHZ, DMSO-d$_6$, 335K) δ 8.05-7.96 (bd, 1 H, nitrobenzyl), 7.87 (d, J=7.6 Hz, 1 H, nitrobenzyl), 7.82 (d, J=7.5 Hz, 2 H, FMOC), 7.75-7.68 (b, 1 H, nitrobenzyl), 7.62-7.54 (bm, 2 H, FMOC), 7.54-7.46 (b, 1 H, nitrobenzyl), 7.39-7.35 (m, 2 H, FMOC), 7.30-7.25 (m, 2 H, FMOC), 5.35 (b, 1 H, E-1), 5.05 (d, J=15.4 Hz, 1 H, nitrobenzyl CH$_2$), 4.99 (d, J =15.4 Hz, 1 H, nitrobenzyl CH$_2$), 4.68 (d, J=6.3 Hz, 1 H, OH), 4.42 (d, J=7.3 Hz, 1 H, A-I), 4.41 (bs, 1 H, OH), 4.20-4.15 (b, 2 H, FMOC CH$_2$), 4.19 (dd, J=5.6, 5.6 Hz, 1 H, benzylic FMOC), 4.00-3.75 (b, 2 H, 2 of E-3, E-5 and E5'), 3.6-3.5 (m, 3 H, A-2, A-3 and A-5), 3.42 (b, 1 H, A-4), 3.35-3.20 (b, 1 H, E-3 or E-5 or E-5'), 3.15 (s, 1 H, E-4), 3.13 (s, 3 N, OCH$_3$), 3.07 (b, 1 H, NCHMe$_2$), 2.41-2.31 (b, 1 H, E-2 eq) 1.33 (ddd, J=13.0, 9.4, 3.6 Hz, 1 H, E-2 ax), 1.12 (d, J=6.4 Hz, 3 H, A-6), 0.9-0.4 (b, 6 H, $^i$Pr CH$_3$); $^{13}$C NMR (500 MHz, DMSO-d$_6$, 335K) δ 146.6, 143.8, 140.6, 133.9, 133.3, 128.3, 127.9, 127.1, 126.6, 124.3, 123.9, 119.6, 100.5, 97.4, 78.8, 74.6, 74.1, 71.3, 71.1, 69.9, 65.4, 59.3, 56.7, 46.6, 45.7, 34.9, 20.0, 19.6, 16.0; IR (CHCl$_3$) v$_{max}$ 3424, 2967, 2935, 1691, 1526, 1450, 1342, 1307, 1167, 1125, 1102, 1067, 996 cm$^{-1}$; HRMS Calcd. for C$_{37}$H$_{44}$O$_{11}$N$_2$ (M+Cs$^+$): 825.1999. Found: 825.2036.

Example 68: Compound 250

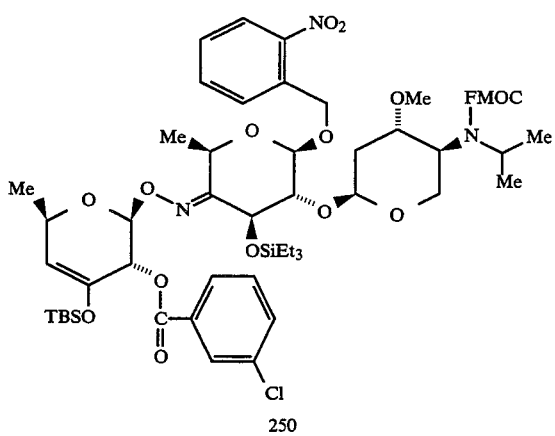

250

R$_f$=0.57 (silica gel, 40 percent ethyl ether in petroleum ether); [α]$_D^{26}$ −65.3° (c=0.37, CHCl$_3$); $^1$H NMR (500 MNz, DMSO-d$_6$, 335K) δ 7.97 (d, J=7.8 Hz, 1 H, nitrobenzyl), 7.89-7.86 (m, 2 H, mCBz), 7.82 (d, J=7.5 Hz, 2 H, FMOC), 7.77 (d, J=7.7 Nz, 1 H, nitrobenzyl), 7.73-7.70 (m, 1 H, mCBz), 7.69-7.64 (m, 1 H, nitrobenzyl), 7.58-7.53 (m, 3 H, FMOC+mCBz), 7.50-7.45 (m, 1 H, nitrobenzyl), 7.39-7.34 (m, 2 H, FMOC), 7.30-7.24 (m, 2 H, FMOC), 5.51 (dd, J=5.9, 1.5 Hz, 1 H, B-2) 5.39 (d, J=5.9 Hz, 1 H, B-1), 5.17 (dd, J=2.0, 1.5 Hz, 1 H, B-4), 5.07 (b, 1 H, E-1), 5.07 (d, J=14.8 Nz, 1 H, nitrobenzyl CH$_2$), 4.94 (d, J=14.8 Nz, 1 H, nitrobenzyl), 4.73 (q, J=6.7 Hz, 1 H, A-5), 4.55 (qdd, J=6.6, 2.0, 2.0 Hz, 1 H, B-5), 4.53 (d, J=5.9 Hz, 1 H, A-1), 4.45-4.35 (b, 1 H, FMOC CH$_2$), 4.30 (dd, J=0.4, 5.6 Hz, 1 H, FMOC CH$_2$), 4.22 (d, J=1.5 Nz, 1 H, A-3), 4.18 (dd, J - 5.6, 5.4 Hz, 1 H, benzylic FMOC), 4.05-3.82 (b, 2 H, 2 of E-3, E-5 and E5'), 3.84 (dd, J=5.9, 1.5 Hz, 1 H, A-2), 3.55-3.40 (b, 1 H, E-3 or E-5 or E-5'), 3.25-3.15 (b, 1 H, E-4), 3.13 (s, 3 H, OCH$_3$), 3.15-3.10 (b, 1 H, NCHMe$_2$), 2.28-2.20 (b, 1 H, E-2 eq) 1.44 (ddd, J=13.1, 10.5, 3.5 Hz, 1 H, E-2 ax), 1.27 (d, J=6.7 Hz, 3 H, A-6), 1.23 (d, J=6.6 Hz, 3 H, B-6), 1.0-0.5 (b, 6 H, $^i$Pr CH$_3$), 0.82 (t, J-7.9 Hz, 9 H, SiCH$_2$CH$_3$), 0.76 (s, 9 H, $^t$Bu), 0.54 (q, J=7.9 Hz, 6 H, SiCH$_2$CH$_3$), 0.16 (s, 3 H, Si$^t$Bu(CH$_3$)$_2$), 0.10 (s, 3 H, Si$^t$Bu(CH$_3$)); $^{13}$C NMR (500 MHz, DMSO-d$_6$, 335K) δ 163.6, 159.5, 146.8, 143.7, 142.9, 140.6, 133.3, 133.1, 131.0, 128.4, 128.2, 128.0, 127.4, 127.1, 126.6, 125.3, 123.9, 119.6, 110.7, 101.7, 101.5, 94.6, 78.0, 70.9, 70.4, 68.1, 68.0, 67.8, 66.3, 65.4, 59.5, 56.5, 54.1, 46.6, 24.9, 21.6, 20.1, 17.6, 5.9, 3.8, −5.2; IR (CDCl$_3$) v$_{max}$ 2958, 2934, 1734, 1694, 1528, 1343, 1308, 1252, 1125, 1086, 1060, 1006, 983, 839, 756 cm$^{-1}$; HRMS Calcd. for C$_{62}$N$_{82}$O$_{15}$N$_3$Si$_2$Cl (M+Cs$^+$): 1332.4027. Found: 1332.4000.

Example 69: Compound 253

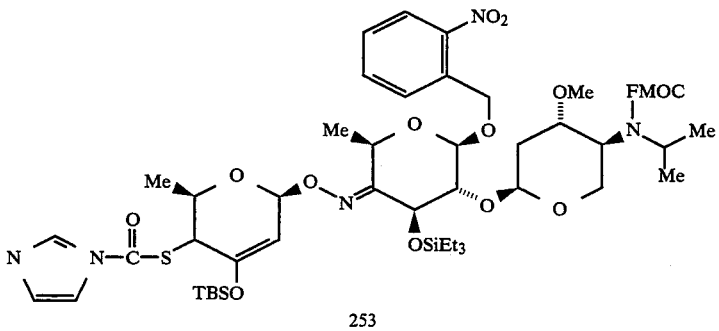

253

R$_f$=0.53 (silica gel, 70 percent ethyl ether in petroleum ether); [α]$_D^{26}$ +25.1° (c=0.55, CHCl$_3$); $^1$H NMR (500 MHz, DMSO-d$_6$, 335K) δ 8.36 (s, 1 H, Imid), 7.98 (d, J=7.9 Hz, 1 H, nitrobenzyl), 7.82 (d, J=7.6 Hz, 2 H, FMOC), 7.78 (d, J=7.7 Hz, 1 H, nitrobenzyl), 7.69 (dd, J=1.5, 1.5 Hz, 1 H, Imid), 7.69 (dd, J=8.1, 8.1 Nz, 1 H, nitrobenzyl), 7.58-7.53 (m, 2 H, FMOC), 7.52-7.47 (m, 1 H, nitrobenzyl), 7.39-7.34 (m, 2 H, FMOC), 7.30-7.24 (m, 2 H, FMOC), 7.12 (m, 1 H, Imid), 5.78 (dd, J=2.5, 0.8 Hz, 1 H, B-2), 5.15 (d, J=2.5 Hz, 1 H, B-1), 5.11 (d, J=14.8 Hz, 1 H, nitrobenzyl CH$_2$), 5.10 (b, 1 H, E-1), 4.96 (d, J=14.8 Hz, 1 H, nitrobenzyl CH$_2$), 4.71 (q, J=6.6 Hz, 1 H, A-5), 4.54 (d, J=5.8 Hz, 1 H, A-1), 4.44-4.34 (b, 1 H, FMOC CH$_2$), 4.30 (dd, J =10.6, 5.6 Hz, I H, FMOC CH$_2$), 4.25 (qd, J=6.5, 3.6 Hz, 1 H, B-5), 4.25 (d, J=2.0 Hz, I H, A-3), 4.19 (dd, J - 5.6, 5.6 Hz, 1 H, benzylic FMOC), 4.04 (d, J=3.6 Hz, 1 H, B-4), 4.03-3.82 (b, 2 H, 2 of E-3, E-5 and E5'), 3.87 (dd, J=5.8, 2.0 Hz, 1 H, A-2), 3.51-3.47 (b, 1 H, E-3 or E-5 or E-5'), 3.21-3.19 (b, 1 H,-E-4), 3.15-3.10 (b, 4 H, OCH$_3$+NCHMe$_2$), 2.22-2.19 (b, 1 H, E-2 eq), 1.45 (ddd, J=13.1, 10.5, 3.6 Hz, 1 cH, E-2 ax), 1.42 (d, J=6.6 Hz, 3 M, A-6), 1.41 (d, J=6.5 Hz, 3 H, B-6), 1.0-0.6 (b, 6 H, $^i$Pr CH$_3$), 0.93 (t, J= 7.9 HZ, 9 H, SiCH$_2$CH$_3$), 0.86 (s, 9 H, $^t$Bu) 0.63 (q, J=7.9 HZ, 6 H, SiCH$_2$CH$_3$), 0.22 (s, 3 H, Si$^t$BU(CH$_3$)$_2$), 0.19 (s, 3 H, Si$^t$Bu(CH$_3$)$_2$)); $^{13}$C NMR (125 MHZ, DMSO-d$_6$, 335K) δ 164.9, 158.3, 147.7, 146.8, 143.7, 140.6, 135.5, 133.2, 133.1, 130.7, 128.5, 128.1, 127.1, 126.5, 124.3, 123.9, 119.6, 116.1, 103.9, 101.5, 97.8, 94.7, 78.1, 72.5, 70.6, 68.3, 66.3, 65.4, 59.4, 56.3, 48.0, 46.6, 34.8, 24.9, 20.0, 19.7, 17.8, 17.3, 6.1, 3.9, −5.2, −5.3; IR (CHCl$_3$) v$_{max}$ 2957, 2935, 1695, 1528, 1471, 1451, 1366, 1307, 1227, 1152, 1098, 1060, 948, 914, 884, 842, 757 cm$^{-1}$; HRMS Calcd. for C$_{59}$H$_{81}$O$_{14}$N$_5$SSi$_2$ (M+Cs$^+$): 1304. 4094. Found: 1304.4071. Anal. Calcd. for C$_{59}$N$_{81}$O$_{14}$N$_5$SSi$_2$: C, 60.44; H, 6.97; N, 5.98; S, 2.73; Si, 4.78. Found: C, 60.52; H, 6.90; N, 5.72; 5,2.62; 5, 4.75.

Example 70: Compound 258 (Step b, FIG. 15)

R$_f$=0.76 (silica gel, 20 percent ethyl acetate in benzene); [α]$_D^{26}$ −26.9° (c=0.34, CHCl$_3$); $^1$H NMR (500 MHz, DMSO-d$_6$, 335K) δ 7.98 (d, J=7.4 Hz, 1 H, nitrobenzyl), 7.82 (d, J=7.6 Hz, 2 H, FMOC), 7.78 (d, J=7.6

Hz, 1 H, nitrobenzyl), 7.69 (dd, J=7.1, 7.1 Hz, 1 H, nitrobenzyl), 7.58-7.53 (m, 2 H, FMOC), 7.52-7.47 (m, 1 H, nitrobenzyl), 7.39-7.34 (m, 2 H, FMOC), 7.30-7.25 (m, 2 H, FMOC), 5.32 (dd, J=10.1, 2.2 Hz, 1 H, B-1), 5.09 (d, J=14.8 Hz, 1 H, nitrobenzyl CH$_2$), 5.10 (b, 1 H, E-1), 4.95 (d, J=14.8 Hz, 1 H, nitrobenzyl CH$_2$), 4.87 (d, J=4.2 Nz, 1 H, B-3 OH), 4.74 (q, J=6.7 Hz, 1 H, A-5), 4.57 (d, J=5.9 Hz, 1 H, A-1), 4.42-4.35 (b, 1 H, FMOC CH$_2$), 4.29 (dd, J=10.4, 5.6 Hz, 1 H, FMOC CH$_2$), 4.26 (d, J=1.9 Hz, 1 H, A-3), 4.19 (dd, J- 5.6, 5.4 Hz, 1 H, benzylic FMOC), 4.14 (m, 1 H, B-3), 4.0-3.8 (b, 2 H, 2 of E-3, E-5 and E5'), 3.88-3.83 (m, 2 H, A-2+B-5), 3.55-3.40 (b, 1 H, E-3 or E-5 or E-5'), 3.21-3.16 (b, 1 H, E-4), 3.15-3.10 (b, 4 H, OCH$_3$+NCHMe$_2$), 2.36 (dd, J=10.2, 2.6 Nz, 1 H, B-4), 2.25-2.20 (b, 1 H, E-2 eq), 2.10 (s, 3 H, SCH$_3$), 1.94 (ddd, J=12.9, 3.5, 2.2 HZ, 1 H, B-2 eq), 1.66 (ddd, J=12.9, 10.1, 2.8 HZ, 1 H, B-2 ax), 1.44 (ddd, J=12.8, 11.0, 3.7 Mz, 1 H, E-2 ax), 1.39 (d, J=6.7 HZ, 3 H, A-6), 1.25 (d, J=6.3 Hz, 3 H, B-6), 1.0-0.6 (b, 6 H, $^i$Pr CH$_3$), 0.92 (t, J=7.9 Hz, 9 H, SiCH$_2$CH$_3$), 0.62 (q, J=7.9 Hz, 6 H, SiCH$_2$CH$_3$); $^{13}$C NMR (125 MHz, C$_6$D$_6$, 293K) δ 160.2, 146.9, 144.9, 141.8, 133.1, 128.7, 128.5, 127.3, 127.2, 127.0, 125.2, 125.1, 124.2, 120.1, 112.7, 103.2, 100.3, 95.2, 78.8, 72.0, 71.5, 69.9, 69.8, 68.5, 66.3, 65.0, 60.7, 56.9, 56.1, 47.6, 36.1, 20.8, 20.7, 20.4, 18.9, 13.2, 7.0, 5.1; IR (CHCl$_3$) $v_{max}$ 3456, 2959, 2935, 1692, 1527, 1450, 1367, 1343, 1307, 1151, 1074, 1018, 757 cm$^{-1}$; HRMS Calcd. for C$_{50}$H$_{69}$O$_{13}$N$_3$SSi (M+Cs$^+$): 1112.3375. Found: 1112.3375. Anal. Calcd. for C$_{50}$N$_{69}$O$_{13}$N$_3$SSi: C, 61.26; H, 7.10; N, 4.29; Si, 2.86. Found: C, 61.97; H, 7.27; N, 3.91; Si, 2.20.

Example 71: Compound 400 Step e, FIG. 15)

R$_f$=0.20 (silica gel, 50 percent acetone in methylene chloride); [α]$_D^{26}$ −42.3° (c=0.104 CHCl$_3$); $^1$H NMR (500 MHz, C$_6$D$_6$) δ 8.12 (d, J=7.8 Nz, 1 H, nitrobenzyl), 7.71 (d, J=8.1 Hz, 1 H, nitrobenzyl), 7.20 (dd, J=7.8, 7.5 Nz, 1 H, nitrobenzyl), δ 6.70 (dd, J=8.1, 7.5 Hz, 1 H, nitrobenzyl), 6.01 (b, 1 H, E-1), 5.78 (b, 1 H, ONH), 5.36 (d, J=15.5 Hz, I H, nitrobenzyl CH$_2$), 5.08 (d, J=15.5 Hz, 1 H, nitrobenzyl CH$_2$), 5.03 (dd, J=10.1, 1.8 Hz, 1 H, B-1), 4.49 (d, J =7.8 Nz, 1 H, A-I), 4.26 (dd, J=9.7, 9.3 Nz, 1 H, A-3), 4.08 (dd, J=9.3, 7.8 Hz, 1 H, A-2), 4.04 (dd, J =11.2, 9.4 Mz, 1 H, E-5), 3.83 (dd, J=11.2, 4.7 Hz, 1 H, E5'), 3.70 (ddd, J=9.5, 9.3, 4.2 Hz, 1 H, E-3), 3.63 (q, J=6.3 Hz, 1 H, B-5), 3.61 (m, 1 H, B-3), 3.56 (dq, J=9.5, 6.2 Hz, 1 H, A-5), 3.14 (s, 3 H, OCH$_3$), 2.89 (ddd, J=9.4, 9.3, 4.7 Hz, 1 H, E-4), 2.65 (septet, J=6.3 Mz, 1 H, NCHMe$_2$), 2.49 (ddd, J=12.5, 4.2, 2.2 Nz, 1 H, E-2 eq), 2.20 (dd, J=9.7, 9.5 Hz, 1 H, A-4), 2.10 (ddd, J=13.1, 3.2, 1.8 Hz, 1 H, B-2 eq), 2.00 (dd, J=10.5, 2.4 Hz, 1 H, B-4), 1.70 (ddd, J=12.5, 9.5, 3.5 Hz, 1 H, E-2 ax), 1.44 (s, 3 H, SCH$_3$), 1.39 (ddd, J=13.1, 10.1, 3.2 Hz, 1 H, B-2 ax), 1.36 (d, J=6.2 Hz, 1 H, B-3 OH), 1.10 (d, J=6.3 Nz, 3 H, B-6), 1 07 (d, J=6.2 Hz, 3 H, A-6), 0.91 (d, J=6.3 Hz, 3 H, $^i$Pr CH$_3$), 0.85 (d, J=6.3 Hz, 3 H, $^i$Pr CH$_3$); $^{13}$C NMR (125 MNz, C$_6$D$_6$) 147.3, 135.5, 133.4, 129.4, 127.5, 124.6, 101.9, 100.0, 98.9, 78.1, 77.8, 72.1, 69.5, 68.9, 68.8, 67.5, 64.9, 63.8, 57.0, 55.9, 55.7, 46.8, 35.8, 34.5, 24.7, 23.0, 20.0, 17.6, 13.3; IR (CHCl$_3$) $v_{max}$ 3444, 2966, 2925, 1526, 1446, 1341, 1305, 1154, 1064, 1015, 990, 960 cm$^{-1}$; HRMS Calcd. for C$_{29}$H$_{47}$O$_{11}$N$_3$S (M+Cs$^+$): 778.1986. Found: 778.1986.

Example 72: Compound 406 (Step d, FIG. 16)

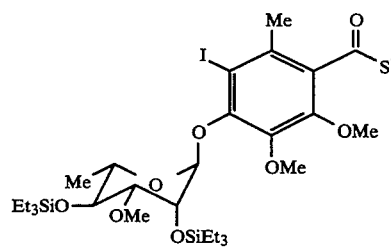
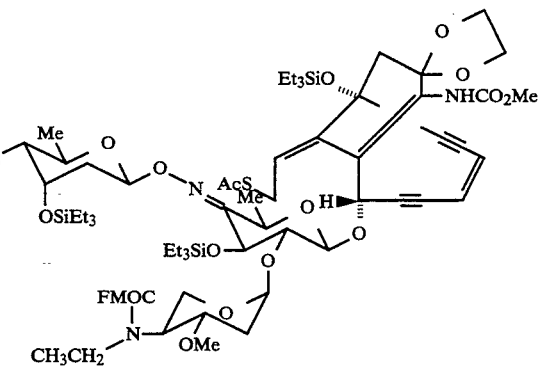

$^1$H NMR (500 MHz, benzene-d$_6$, 340° K.) δ 7.65-7.58 (m, 4 H), 7.24-7.10 (m), 6.53 (dd, J=8 Hz, 1 H, vinylic), 6.29 (bs, 1 H, propargylic), 6.04 (vbs, 1 H), 5.81 (dd, J=9.9, 2.1 Hz, 1 H, B-1), 5.76 (d, J=2.0 Hz, 1 H, D-1), 5.46-5.44 (m, 2 H, Enediyne), 5.30 (bs, 1 H, E-1), 5.13 (q, J=6.6 Hz, 1 H, A-5), 4.62 (d, J=2.7 Hz, 1 H, A-1), 4 59 ("t" J=2.3 Hz, 1 H), 4.49 (bs, 1 H), 4.44-4.25 (m, 8 H, D-1, B-3, CHO's), 4.16 (m, 1 H), 4.05 ("t", J=9.1 Hz, 1H), 4.02 ("dd", J=10.5, 2.5 Hz, 1 H), 3.95-3.90 (m), 3.87 (dd, J=9.1, 2.7 Hz, 1 H), 3.72 (s, 3 H, OCH$_3$), 3.55 (s, 3 H, OCH$_3$), 3.51 (bs, 2 H), 3.37 (m, 3 H), 3.36 (s, 3 H, OCH$_3$), 3.14 (s, 3 H, OCH$_3$), 2.46 (s, 3 H, CH$_3$-Arom), 2.38 (m, 2 H), 2.30 (s), 2.02 (m, 1 H), 1.95 (s, 3 H), 1.87 (d, J=6.8 Hz, 3 H, A-6), 1.57 (d, J=6.3 Hz, 3 H, B-6), 1.41 (d, J=6.2 Hz, 3 H, D-6), 1.38-1.28 (m), 1.13-0.55 (series of multiplets); FAB HRMS (NBA/CsI) M+CS$^+$+C$_{13}$ calcd for C$_{103}$H$_{156}$O$_{25}$N$_3$Si$_5$S$_2$I: 2299.744, found 2299.737.

The foregoing is intended as illustrative of the present invention but not limiting. Numerous variations and modifications may be effected without departing from the true spirit and scope of the novel concepts of the invention.

We claim:

1. A compound having the structural formula

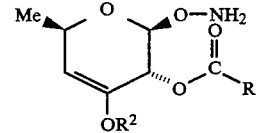

wherein R is a moiety selected from the group consisting of hydrogen, C$_1$–C$_5$ alkyl, phenyl and m-chlorophenyl; and $R^2$ is a moiety selected from the group consisting of tri-$C_1$-$C_6$ alkylsilyl, di-$C_1$-$C_6$ alkylphenylsilyl, and $C_1$-$C_6$ alkyldiphenylsilyl.

2. The compound of claim 1 wherein said R moiety is a m-chlorophenyl moiety.

3. The compound of claim 1 wherein $R^2$ is a tri-$C_1$-$C_6$ alkylsilyl moiety.

4. The compound of claim 3 wherein said tri-$C_1$-$C_6$ alkylsilyl moiety is a t-butyldimethylsilyl moiety.

5. A compound having the structural formula

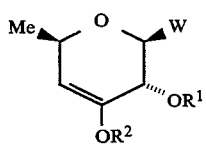

where $R^1$ is hydrogen or COR, and R is a moiety selected from the group consisting of hydrogen, $C_1$-$C_6$ alkyl, phenyl and m- chlorophenyl;

$R^2$ is a moiety selected from the group consisting of tri-$C_1$-$C_6$ alkylsilyl, di-$C_1$-$C_6$ alkylphenylsilyl, and $C_1$-$C_6$ alkyldiphenylsilyl; and —W is (i) an N-hydroxy cyclic imido group, —ON=$R^4$, in which $R^4$ has 4 to about 8 carbon atoms or (ii) an O,N-disubstituted oxime group, —ON=$R^5$, that is a reaction product of a hydroxylamine and a compound that is selected from the group consisting of a $C_1$-$C_6$ alkyl ketone or aldehyde and a tetrahydropyranone, with the proviso that $R^1$ is COR when —W is —ON=$R^4$.

6. The compound of claim 5 wherein R is a m-chlorophenyl moiety.

7. The compound of claim 6 wherein $R^2$ is a tri-$C_1$-$C_6$ alkylsilyl moiety.

8. The compound of claim 7 wherein —W is an N-hydroxy cyclic imido group having 4 to about 8 carbon atoms.

9. The compound of claim 8 wherein the N-hydroxy cyclic imido group is an N-hydroxy phthalimido or N-hydroxy succinimido group.

10. The compound of claim 7 wherein —W is said O,N-disubstituted oxime group.

11. The compound of claim 10 wherein $R^5$ is isopropylidene.

12. A compound having the structural formula

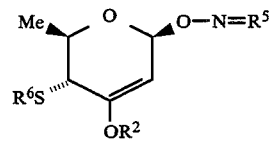

wherein $R^2$ is a moiety selected from the group consisting of tri-$C_1$-$C_6$ alkylsilyl, di-$C_1$-$C_6$ alkylphenylsilyl, and $C_1$-$C_6$ alkyldiphenylsilyl;

—ON=$R^5$ is an O,N-disubstituted oxime group that is a reaction product of a hydroxylamine and a compound that is selected from the group consisting of a $C_1$-$C_6$ alkyl ketone or aldehyde and a tetrahydropyranone; and $R^6$ is selected from the group consisting of hydrogen, $C_1$-$C_6$ alkyl, benzoyl, m-chlorobenzoyl, $C_1$-$C_6$ alkyl oxycarbonyl and N-carbonyl imidazyl.

13. The compound of claim 12 wherein $R^6$ is hydrogen.

14. The compound of claim 12 wherein $R^6$ is m-chlorobenzoyl.

15. The compound of claim 12 wherein $R^5$ is a tetrahydropyranone reaction product.

16. The compound of claim 15 wherein said tetrahydropyranone reaction product is a tetrahydropyran-4-one reaction product.

* * * * *